United States Patent
Sadhasivam

(10) Patent No.: US 10,878,939 B2
(45) Date of Patent: Dec. 29, 2020

(54) METHODS AND COMPOSITIONS FOR PERSONALIZED PAIN MANAGEMENT

(71) Applicant: Children's Hospital Medical Center, Cincinnati, OH (US)

(72) Inventor: Senthilkumar Sadhasivam, Mason, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 326 days.

(21) Appl. No.: 15/120,087

(22) PCT Filed: Feb. 23, 2015

(86) PCT No.: PCT/US2015/017134
§ 371 (c)(1),
(2) Date: Aug. 18, 2016

(87) PCT Pub. No.: WO2015/127379
PCT Pub. Date: Aug. 27, 2015

(65) Prior Publication Data
US 2017/0061073 A1    Mar. 2, 2017

Related U.S. Application Data

(60) Provisional application No. 61/943,944, filed on Feb. 24, 2014.

(51) Int. Cl.
| | |
|---|---|
| *G01N 33/48* | (2006.01) |
| *G16B 40/00* | (2019.01) |
| *C12Q 1/6883* | (2018.01) |
| *A61K 31/485* | (2006.01) |
| *C12Q 1/68* | (2018.01) |
| *G06G 7/58* | (2006.01) |

(52) U.S. Cl.
CPC ............ *G16B 40/00* (2019.02); *A61K 31/485* (2013.01); *C12Q 1/68* (2013.01); *C12Q 1/6883* (2013.01); *C12Q 2600/106* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,675,904 A | 6/1987 | Silverman |
| 5,148,483 A | 9/1992 | Silverman |
| 5,288,644 A | 2/1994 | Beavis et al. |
| 5,445,934 A | 8/1995 | Fodor et al. |
| 5,700,637 A | 12/1997 | Southern |
| 5,744,305 A | 4/1998 | Fodor et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,429,027 B1 | 8/2002 | Chee et al. |
| 6,733,977 B2 | 5/2004 | Besemer et al. |
| 6,858,394 B1 | 2/2005 | Chee et al. |
| 7,364,858 B2 | 4/2008 | Barany et al. |
| 7,754,428 B2 | 7/2010 | Lo et al. |
| 7,858,313 B2 | 12/2010 | Ikeda et al. |
| 9,691,411 B2 | 6/2017 | Scherer |
| 9,944,985 B2 | 4/2018 | Sadhasivam et al. |
| 10,662,476 B2 | 5/2020 | Sadhasivam et al. |
| 2002/0077825 A1 | 6/2002 | Silverman |
| 2002/0110823 A1 | 8/2002 | Hogan |
| 2003/0078768 A1 | 4/2003 | Silverman |
| 2003/0092019 A1 | 5/2003 | Meyer et al. |
| 2003/0167189 A1 | 9/2003 | Lutgen |
| 2007/0233468 A1 | 10/2007 | Ozdas et al. |
| 2007/0233498 A1 | 10/2007 | Silverman et al. |
| 2008/0201280 A1 | 8/2008 | Huber et al. |
| 2009/0253585 A1* | 10/2009 | Diatchenko .......... C12O 1/6883 506/9 |
| 2010/0143929 A1 | 7/2010 | Levenson et al. |
| 2010/0240552 A1 | 9/2010 | Ikeda et al. |
| 2010/0262603 A1 | 10/2010 | Odom et al. |
| 2011/0257098 A1 | 10/2011 | Tuefferd et al. |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2013/0310549 A1 | 11/2013 | Shuber |
| 2014/0371256 A1 | 12/2014 | Sadhasivam et al. |
| 2016/0180041 A1 | 6/2016 | Pestian et al. |
| 2017/0233813 A1 | 8/2017 | Rothenberg et al. |

(Continued)

FOREIGN PATENT DOCUMENTS

| | | |
|---|---|---|
| EP | 0 619 321 A1 | 10/1994 |
| EP | 0 619 321 B1 | 10/1994 |
| EP | 2785874 B1 | 9/2018 |

(Continued)

OTHER PUBLICATIONS

Campa, D. et al. (Apr. 2008, e-published Sep. 26, 2007). "Association of ABCB1/MDR1 and OPRM1 gene polymorphisms with morphine pain relief," Clin Pharmacol Ther 83(4):559-566.

Choi, E.M. et al. (Oct. 2010). "Association of ABCB1 polymorphisms with the efficacy of ondansetron for postoperative nausea and vomiting," Anaesthesia 65(10):996-1000.

Coulbault, L. et al. "Environmental and genetic factors associated with morphine response in the postoperative period." Clinical Pharmacology and Therapeutics, 79(4):316-324 (2006).

De Gregori M. et al. "Individualizing pain therapy with opioids: The rational approach based on pharmacogenetics and pharmacokinetics." European Journal of Pain Supplements, 4(4):245-250 (2010).

Laugsand, E.A. et al. "Clinical and genetic factors associated with nausea and vomiting in cancer patients receiving opioids." European Journal of Cancer, 47(11):1682-1691 (2011).

(Continued)

*Primary Examiner* — Eric S Dejong
(74) *Attorney, Agent, or Firm* — Muriel Liberto, Esq.; Mintz Levin Cohn Ferris Glovsky and Popeo, P.C.

(57) ABSTRACT

The invention provides methods, kits and systems related to personalized pain management.

22 Claims, 24 Drawing Sheets

(56) References Cited

U.S. PATENT DOCUMENTS

| | | |
|---|---|---|
| 2018/0334717 A1 | 11/2018 | Sadhasivam et al. |
| 2019/0367988 A1 | 12/2019 | Chidambaran et al. |

FOREIGN PATENT DOCUMENTS

| | | |
|---|---|---|
| JP | 2012-070732 A | 4/2012 |
| WO | WO-89/10977 A1 | 11/1989 |
| WO | WO-03/054166 A2 | 7/2003 |
| WO | WO-03/054166 A3 | 7/2003 |
| WO | 2005095601 A1 | 10/2005 |
| WO | WO-2005/105093 A2 | 11/2005 |
| WO | WO-2005/105093 A3 | 11/2005 |
| WO | WO-2009/067473 A2 | 5/2009 |
| WO | WO-2010/126867 A1 | 11/2010 |
| WO | WO-2012/025765 A1 | 3/2012 |
| WO | WO-2012/177945 A2 | 12/2012 |
| WO | WO-2012/177945 A3 | 12/2012 |
| WO | WO-2013/082308 A1 | 6/2013 |
| WO | WO-2013/126834 A1 | 8/2013 |
| WO | WO-2013/155010 A1 | 10/2013 |
| WO | WO-2014/059178 A1 | 4/2014 |
| WO | WO-2014/190269 A1 | 11/2014 |
| WO | WO-2015/017731 A1 | 2/2015 |
| WO | 2015127379 A1 | 8/2015 |
| WO | WO-2016/023026 A1 | 2/2016 |
| WO | 2018136728 A1 | 7/2018 |
| WO | 2020006175 A1 | 1/2020 |

OTHER PUBLICATIONS

Gasche, Y. et al. (Dec. 30, 2004). "Codeine intoxication associated with ultrarapid CYP2D6 metabolism," *N Engl J Med* 351(27):2827-2831.

Hirschhorn, J.N. et al. (Mar.-Apr. 2002). "A comprehensive review of genetic association studies," *Genet Med* 4(2):45-61.

Ioannidis, J.P. et al. (Nov. 2001). "Replication validity of genetic association studies," *Nat Genet* 29(3):306-309.

Jannetto, P.J. et al. (2011, e-published May 18, 2011). "Pain management in the 21$^{st}$ century:utilization of pharmacogenomics and therapeutic drug monitoring," *Expert Opin Drug Metab Toxicol* 7(6):745-752.

Kleine-Brueggeney, M et al. "Pharmacogenetics in palliative care." Forensic Science International, 203:63-70 (2010).

Pattinson, K. "Opioids and the control of respiration." British Journal of Anaesthesia, 100(6):747-758 (2008).

Lucentini, J (Dec. 20, 2004). "Gene Association Studies Typically Wrong," *The Scientist* 24:20.

Park, H.J .et al. (Apr. 2007, e-published Dec. 27, 2006). "Genetic polymorphisms in the ABCB1 gene and the effects of fentanyl in Koreans," *Clin Pharmacol Ther* 81(4):539-546.

Pennisi, E. (Sep. 18, 1998). "A closer look at SNPs suggests difficulties," *Science* 281(5384):1787-1789.

Ross, J.R. et al. "Genetic variation and response to morphine in cancer patients—Catechol-O-methyltransferase and multidrug resistance-1 gene polymorphisms are associated with central side effects." Cancer, 112(6):1390-1403 (2008).

Sadhasivam S. et al. "Pharmacogenetics and personalizing perioperative analgesia in children." Journal of Pain, 11(4):550.

Shi, Q. et al. (Dec. 2010, e-published Sep. 15, 2010). "Biological pathways and genetic variables involved in pain," *Qual Life Res* 19(10):1407-1417.

Stamer, U.M. et al. (Sep. 2008). "Respiratory Depression with Tramadol in a Patient with Renal Impairment and CYP2D6 Gene Duplication," International Anesthesia Research Society 107(3):926-929.

Zwisler Stine T et al. "The antinociceptive effect and adverse drug reactions of oxycodone in human experimental pain in relation to genetic variations in the OPRM1 and ABCB1 genes." Fundamental & Clinical Pharmacology, 24(4): 517-524 (2010).

International Search Report dated Mar. 20, 2013, for PCT Application No. PCT/US2012/067111, filed on Nov. 29, 2012, 4 pages.

Written Opinion dated Mar. 20, 2013, for PCT Application No. PCT/US2012/067111, filed on Nov. 29, 2012, 5 pages.

Snpdev: "Reference SNP (refSNP) Cluster Report: r5967935", XP055471695, Retrieved from the Internet: URL:https://www.ncbi.nlm.nih.gov/projects/SNP/snp_ref.cgi?rs=967935 [retrieved on May 2, 2018].

Chang Hsueh-Wei et al: "SNP-RFLPing 2: an updated and integrated PCR-RFLP tool for SNP genotyping", BMC Bioinformatics, Biomed Central, London, GB, vol. 11, No. 1, Apr. 8, 2010 (Apr. 8, 2010), p. 173, XP021071516, ISSN: 1471-2105, DOI: 10.1186/1471-2105-11-173.

Anonym: "Illumina_top_bot_strand", Apr. 24, 2018 (Apr. 24, 2018), XP055471699, [retrieved on May 2, 2018].

Anderson, B. et al. (Sep. 2011). "Evaluation of a morphine maturation model for the prediction of morphine clearance in children," *Br J Clin Pharmcol* 72(3):518-520; author reply 521-523.

Barratt, D.T. et al. (2012, e-published Apr. 18, 2012). "ABCB1 haplotype and OPRM1 118A > G genotype interaction in methadone maintenance treatment pharmacogenetics," *Pharmgenomics Pers Med* 5:53-62.

Biesiada, J. et al. (Nov. 2014). "Genetic risk signatures of opioid-induced respiratory depression following pediatric tonsillectomy," *Pharmacogenomics* 15(14):1749-1762.

Branford, R. et al. (Oct. 2012, e-published Jul. 27, 2012). "Opioid genetics: the key to personalized pain control?" *Clin Genet* 82(4):301-310.

Clavijo, C.F. et al. (May 2011, e-published Mar. 12, 2011). "A sensitive assay for the quantification of morphine and its active metabolites in human plasma and dried blood spots using high-performance liquid chromatography-tandem mass spectrometry," *Anal Bioanal Chem* 400(3):715-728.

Collins, R.T. et al. (Oct. 2005). "Online selection of discriminative tracking features," IEEE Trans Patter Anal Mach Intell 27(10):1631-1643.

Cohen, M. et al. (Aug. 2012). "Pharmacogenetics in perioperative medicine," *Curr Opin Anaesthesiol* 25(4):419-427.

Dellon, E.S. et al. (Dec. 2013, e-published Oct. 22, 2013). "Clinical and endoscopic characteristics do not reliably differentiate PPI-responsive esophageal eosinophilia and eosinophilic esophagitis in patients undergoing upper endoscopy: a prospective cohort study," Am J Gastroenterol 108(12):1854-1860.

Dellon, E.S. et al. (May 1, 2014). "Immunohistochemical Evidence of Inflammation is Similar in Patients with Eosinophilic Esophagitis and PPI-Responsive Esophageal Eosinophilia: A Prospective Cohort Study," Gastroenterology 146(5), Supplement 1, p. S-17.

Eissing, T. et al. (Feb. 1, 2012). "Pharmacogenomics of codeine, morphine, and morphine-6-glucuronide: model-based analysis of the influence of CYP2D6 activity, UGT2B7 activity, renal impairment, and CYP3A4 inhibition," *Mol Diagn Ther* 16(1):43-53.

Extended European Search Report dated Nov. 16, 2017, for EP Application No. 15828951.2, filed Aug. 10, 2015, 8 pages.

Fukada, T. et al. (Jul. 2013). "OCT1 genetic variants influence the pharmacokinetics of morphine in children," *Pharmacogenomics* 14(10):1141-1151.

Fukuda, T. et al. (Feb. 2013). *Clinical Pharmacology & Therapeutics* 93:S49.

Guyon, I. et al. (2002). "Gene Selection for Cancer Classification using Support Vector Machines," Machine Learning 46:389-422.

Himes, B.E. et al. (May-Jun 2009, e-published Mar. 4, 2009). "Prediction of chronic obstructive pulmonary disease (COPD) in asthma patients using electronic medical records," J Am Med Inform Assoc 16(3):371-379.

International Search Report issued in PCT/US2014/039357 dated Sep. 24, 2014.

International Search Report and Written Opinion issued in PCT/US2014/049301 dated Dec. 8, 2014.

International Search Report dated Nov. 9, 2015 for International Application No. PCT/US2015/044461, filed Aug. 10, 2015, 3 pages.

Juffali, W et al. The Winam Project: Neural Data Analysis with Applications to Epilepsyy Biomedical Circuits and Systems Conference (BioCAS), 2010, pp. 45-48.

(56) References Cited

OTHER PUBLICATIONS

Kelly, L.E. et al. (May 2012, e-published Apr. 9, 2012). "More codeine fatalities after tonsillectomy in North American children," *Pediatrics* 129(5):e1343-1347.
Leschziner, G.D. et al. (Jun. 2007, e-published Sep. 12, 2006). "ABCB1 genotype and Pgp expression, function and therapeutic drug response: a critical review and recommendations for future research," *Pharmacogenomics J.* 7(3):154-179.
Meineke, I. et al. (Dec. 2002). "Pharmacokinetic modelling of morphine, morphine-3-glucuronide and morphine-6-glucuronide in plasma and cerebrospinal fluid of neurosurgical patients after short-term infusion of morphine," *Br J Clin Pharmacol* 54(6):592-603.
Mizuno, T. et al. (2013). Clinical Pharmacology & Therapeutics, 93:S63.
Mogil, J.S. (Jul. 6, 1999). "The genetic mediation of individual differences in sensitivity to pain and its inhibition," *PNAS USA* 96(14):7744-7751.
Ozdas, Asli, et al. "Investigation of vocal jitter and glottal flow spectrum as possible cues for depression and near-term suicidal risk." IEEE Transactions on Biomedical Engineering 51.9(2004): 1530-1540.
Prows, C.A. et al. (May 2014, e-published Nov. 13, 2013). "Codeine-related adverse drug reactions in children following tonsillectomy: a prospective study," *Laryngoscope* 124(5):1242-1250.
Ray, R. et al. (May 31, 2011, e-published May 16, 2011). Human Mu Opioid Receptor (OPRM1 A118G) polymorphism is associated with brain mu-opioid receptor binding potential in smokers, *PNAS USA* 108(22):9268-9273.
Sadhasivam, S. et al. (May 2012, e-published Apr. 23, 2012). "Race and unequal burden of perioperative pain and opioid related adverse effects in children," *Pediatrics* 129(5):832-838.
Sadhasivam, S. et al. (Jul. 2012, e-published Jun. 13, 2012). "Preventing opioid-related deaths in children undergoing surgery," Pain Med 13(7):982-983, author reply 984.
Sadhasivam, S. et al. (Jul.-Aug. 2012). "Morphine clearance in children: does race or genetics matter?" *J Opioid Manag* 8(4):217-226.
Sadhasivam S. et al. (2014). "Genetics of pain perception, COMT and postoperative pain management in children," *The Pharmacogenomics Journal* 15(3):277-284.
Sadhasivam S. et al. (2015). Novel Associations between FAAH Genetic Varients an Postoperative Central Opioid Related Adverse Effects, *The Pharmacogenomics Journal* 15(5):436-442.
Scherer, Stefan, John Pestian, and Louis-Philippe Morency. "Investigating the speech characteristics of suicidal adolescents." 2013 IEEE International Conference on Acoustics, Speech and Signal Processing. IEEE, 2013.
Tzvetkov, M.V. et al. (Sep. 2013, e-published Jul. 5, 2013). "Morphine is a substrate of the organic cation transporter OCT1 and polymorphisms in OCT1 gene affect morphine pharmacokinetics after codeine administration," *Biochem Pharmacol* 86(5):666-678.
Venek, Verena, et al. "Adolescent suicidal risk assessment in clinician-patient interaction: A study of verbal and acoustic behaviors." Spoken Language Technology Workshop (SLT), 2014 IEEE. IEEE, 2014.
Venkatasubramanian, R. et al. (Jul. 2014). "ABCC3 and OCT1 genotypes influence pharmacokinetics of morphine in children," *Pharmacogenomics* 15(10):1297-1309.
Verspoor, K. et al. (Jun. 15, 2009). "The textual characteristics of traditional and Open Access scientific journals are similar," BMC Bioinformatics 10:183.
Wen, T. et al. (Dec. 2013, e-published Aug. 23, 2013). "Molecular diagnosis of eosinophilic esophagitis by gene expression profiling," Gastroenterology 145(6):1289-1299.
Wen, T. et al. (Jan. 2015, Oct. 19, 2014). "Transcriptome analysis of proton pump inhibitor-responsive esophageal eosinophilia reveals proton pump inhibitor-reversible allergic inflammation," J Allergy Clin Immunol 135(1):187-197.
Zeng, Q.T. et al. (Jul. 26, 2006). "Extracting principal diagnosis, co-morbidity and smoking status for asthma research: evaluation of a natural language processing system," BMC Med Inform Decis Mark 6:30.
Buchheit, et al. (2012). "Epigenetics and the Transition from Acute to Chronic Pain." Pain Medicine 13(11):1474-1490.
Chidambaran, et al. (2017). "ABCC3 Genetic Variants Are Associated With Postoperative Morphine-Induced Respiratorydepression and Morphine Pharmacokinetics in Children." Pharmacogenomics Journal 17(2):162-169.
Chorbov, et al. (2011). "Elevated Levels of DNA Methylation at the OPRM1 Promoter in Blood and Sperm from Male Opioid Addicts." Journal of Opioid Management 7(4):258:264.
Extended European Search Report dated Jul. 21, 2015 issued in European Application No. 12854522.5, filed Oct. 8, 2014. 8 pages.
Extended European Search Report dated May 8, 2019 issued in European Application No. 18196397.6, filed Sep. 24, 2018. 12 pages.
Federal Register (Feb. 9, 2011). 76(27):7166. 14 pages.
Hacker, et al. (1997). "Lack of association between an interleukin-1 receptor antagonist gene polymorphism and ulcerative colitis." Gut 40:623-627.
International Preliminary Report on Patentability dated Jun. 12, 2014 for International Application No. PCT/US2012/067111, filed Nov. 29, 2012. 7 pages.
International Preliminary Report on Patentability dated Sep. 9, 2016 for International Application No. PCT/US2015/017134, filed Feb. 15, 2015. 9 pages.
International Preliminary Report on Patentability dated Aug. 1, 2019 for International Application No. PCT/US2018/014405, filed Jan. 19, 2018. 10 pages.
International Search Report and Written Opinion dated May 10, 2018 for International Application No. PCT/US2018/014405, filed Jan. 19, 2018. 15 pages.
International Search Report and Written Opinion dated Oct. 24, 2019 for International Application No. PCT/US2019/039411, filed Jun. 27, 2019. 10 pages.
Kim, et al. (2006). "Genetic Predictors for Acute Experimental Cold and Heat Pain Sensitivity in Humans." Journal of Medical Genetics, e40, 43(8):8 pages.
Larkin, et al. (2010). "A candidate gene study of obstructive sleep apnea in European Americans and African Americans." American Journal of Respiratory and Critical Care Medicine 182:947-953.
Muller, et al. (Jan. 1, 2010). "Mutation Screen and Association Studies for the Fatty Acid Amide Hydrolase (Faah) Gene and Early Onset and Adult Obesity." BMC Medical Genetics 11:2.
Nies, et al. (2009). "Expression of organic cation transporters OCT1 (SLC22A 1) and OCT3 (SLC22A3) is affected by genetic factors and cholestasis in human liver." Hepatology 50(4):1227-1240.
Partial European Search Report dated Feb. 2, 2019 issued in European Application No. 18196397.6, filed Sep. 24, 2018.12 pages.
Shrestha, et al. (Feb. 10, 2016). "Epigenetic Regulations of GABAergic Neurotransmission: Relevance for Neurological Disorders and Epigenetic Therapy." Medical Epigenetics 4(1):1-19.
Shu, et al. (2007). "Effect of Genetic Variation in the Organic Cation Transporter 1 (OCT1) on Metformin Action." Journal of Clinical Investigation 117(5):1422-1431.
Sloan, et al. (May 10, 2012). "Genetic Variations and Patient-Reported Quality of Life Among Patients With Lung Cancer." Journal of Clinical Oncology 30(14):1699-1704.
Stamer, et al. (Jun. 1, 2010). "Personalized therapy in pain management: where do we stand?" Pharmacogenomics 11(6):843-864.
International Search Report issued in PCT/US2015/017134 dated May 6, 2016.
K R Crews et al: "Clinical Pharmacogenetics Implementation Consortium Guedelines for Cytochrome P450 2D6 Genotype and Codeine Therapy: 2014 Update", Clinical Pharmacology & Therapeutics, vol. 95, No. 4, Jan. 29, 2014 (Jan. 29, 2014), pp. 376-382, XP055185334, ISSN: 0009-9236, DOI: 10.1038/clpt.2013.254 "Therapeutic recommendation" bridging pp. 379 and 380 table 2 "Potential Benefits and Risks for the Patient" on p. 380.

(56) References Cited

OTHER PUBLICATIONS

Xiao-Di Gong et al: "Gene Polymorphisms of OPRM1 A118G and ABCB1 C3435T May Influence Opioid Requirements in Chinese Patients with Cancer Pain", Asian Pacific Journal of Cancer Prevention, vol. 14, No. 5, May 30, 2013 (May 30, 2013), pp. 2937-2943.

* cited by examiner

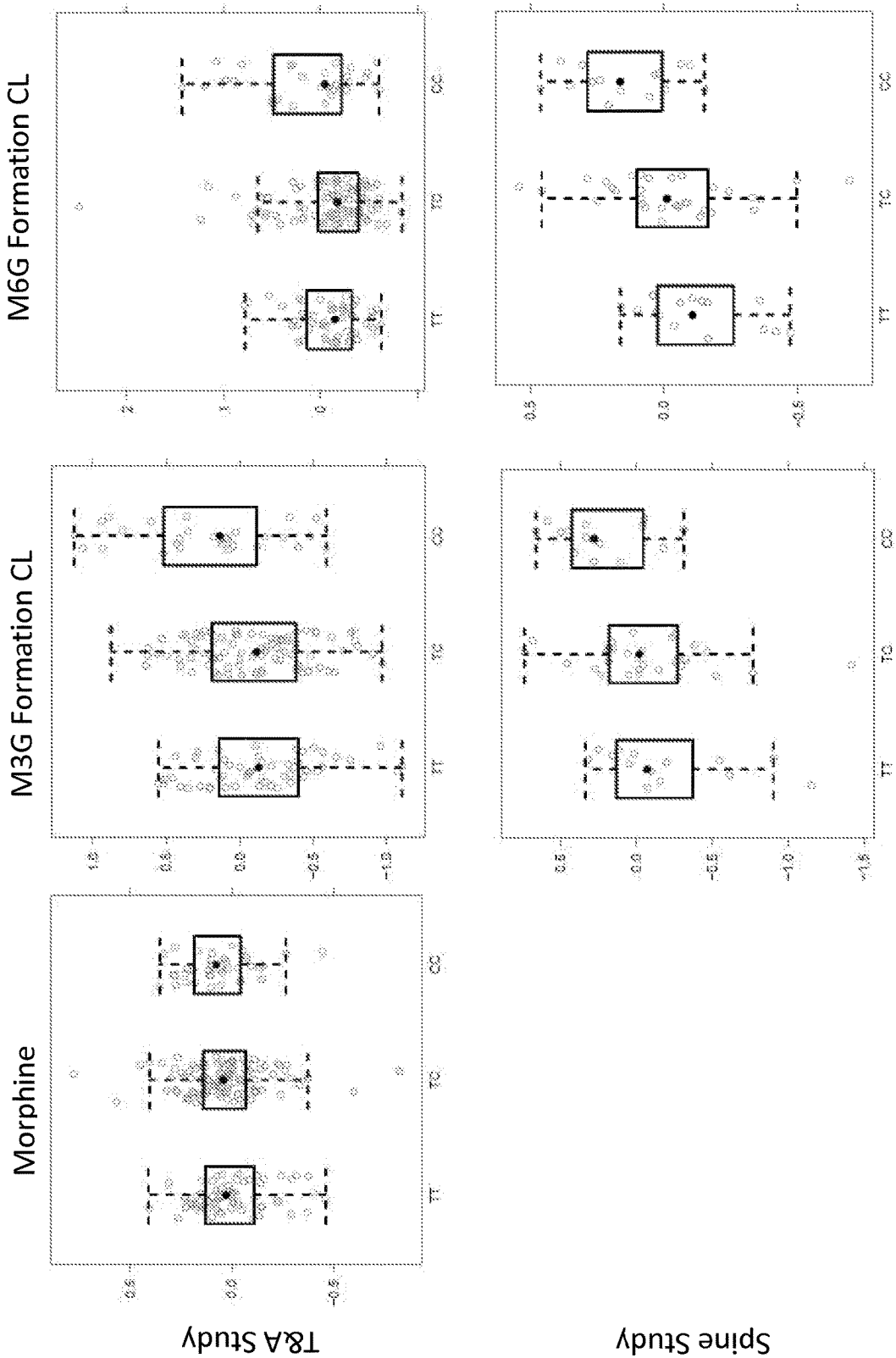

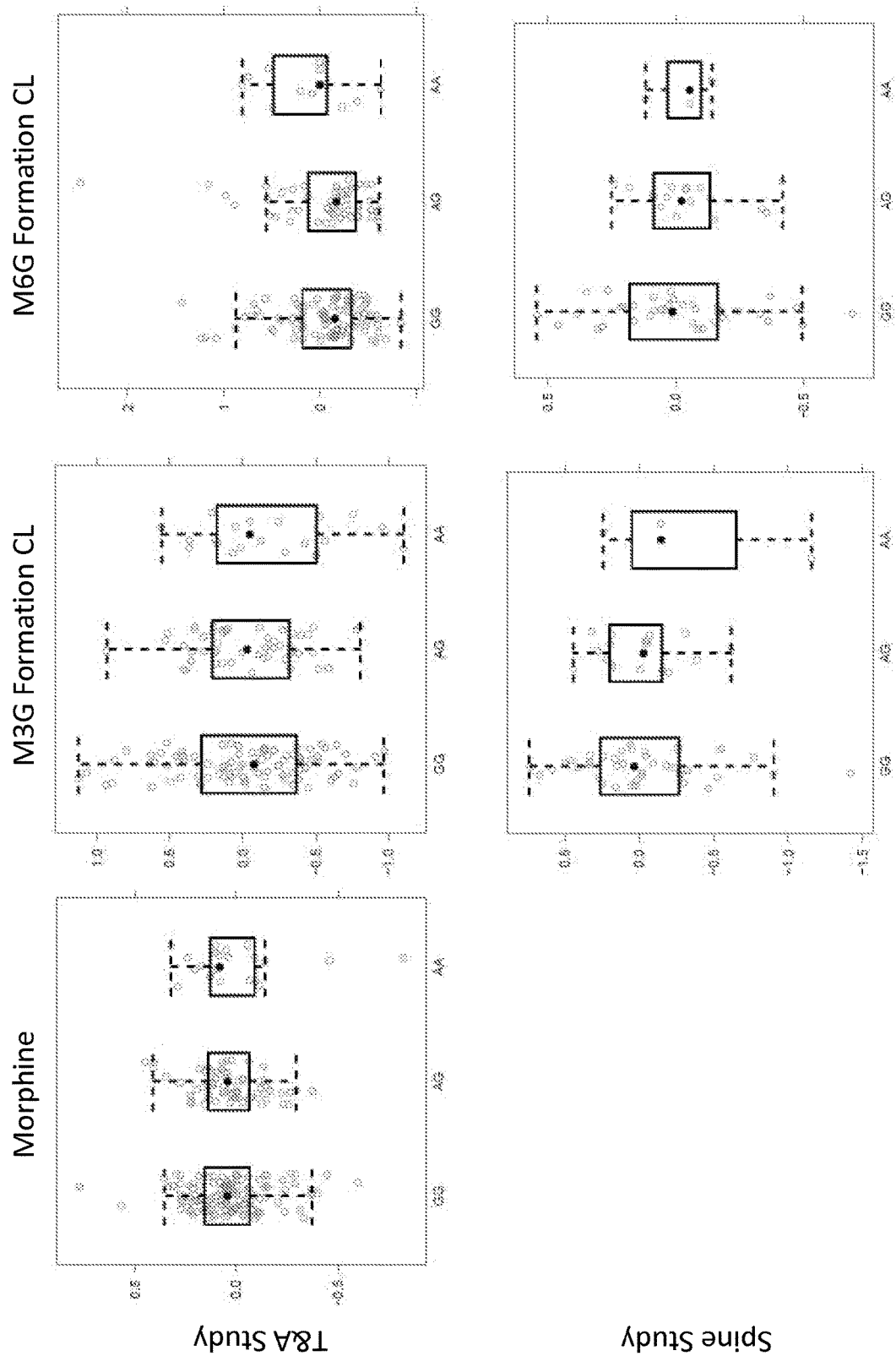

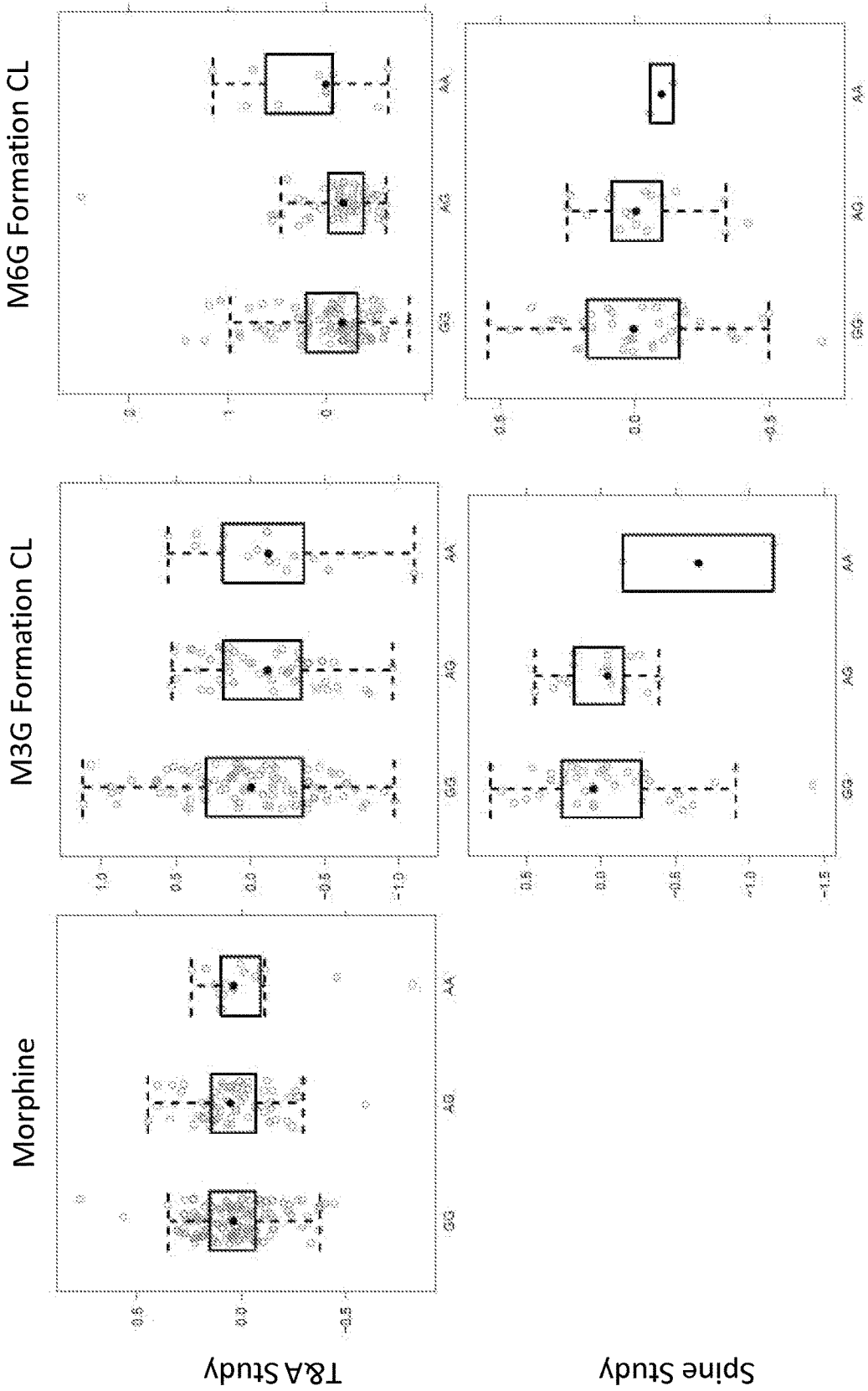

METHODS AND COMPOSITIONS FOR PERSONALIZED PAIN MANAGEMENT

CROSS-REFERENCES TO RELATED APPLICATIONS

This application is a national stage entry, filed under 35 U.S.C. § 371, of International Application No. PCT/US2015/017134, filed on Feb. 23, 2015, and claims the benefit of and priority to U.S. Provisional Patent Application No. 61/943,944, filed Feb. 24, 2014, the entire contents of which is hereby incorporated herein by reference in its entirety and for all purposes.

STATEMENT REGARDING FEDERALLY-SPONSORED RESEARCH

This invention was made with government support under RR026314 and HG006828 awarded by the National Institutes of Health. The government has certain rights in the invention.

FIELD OF THE INVENTION

The invention disclosed herein generally relates to methods and compositions for pain management.

BACKGROUND

Safe and effective analgesia is an important unmet medical need. See e.g., Sadhasivam and Chidambaran, *Pharmacogenomics* (2012) 13(15):1719-1740; Caldas, J. et al., *Paediatr. Anaesth.*, 14:910-5 (2004); Duedahl, T. and Hansen, E., *Paediatr. Anaesth.*, 17:756-74 (2007)). Opioids are commonly used analgesics for managing postoperative pain. Although they have significant analgesic strength, opioids also have a narrow therapeutic index and a number of associated adverse effects including, for example, respiratory depression, miosis, drowsiness, nausea, vomiting, and constipation. Morphine is the most commonly used opioid during the perioperative period. Unpredictable inter-patient variations in opioid responses and narrow therapeutic index of morphine result in a high incidence of morphine-induced respiratory depression. Opioid-induced respiratory depression is the most serious adverse effect of opioids, responsible for up to 50% of postoperative respiratory failure events (Fecho K. et al., *Therapeut. and Clin. Risk Mgmt.* 5:961-8 (2009)). Twin studies have revealed significant heritability (30%) for respiratory depression from opioids (Angst M. et al., *Anesthesiology* 117:22-37 (2012)). Approximately 50% of the inter-individual variability in clinical response to morphine may be explained by SNPs in the genes involved in pain mechanisms and opioid metabolism, transport, and receptor signaling. Contributing non-genetic risk factors such as female sex, race, medical comorbidities and other genetic risk factors like CYP2D6 variants have also been described (Ramachandran S. et al., *J. Clin. Anesth.* 23:207-13 (2011); Niesters M. et al., *British Journal of Anaesthesia* 110:175-82 (2013)). Efforts to predict patient response to opioids can have a great impact in enabling clinicians to personalize analgesia to maximize pain relief while minimizing its adverse effects.

Tonsillectomy is one of the most common and significantly painful surgical procedures children undergo. Each year, about 530,000 tonsillectomies are performed in the United States alone (Erickson B. et al., *Otolaryngol. Head Neck Surg.*, 140:894-901 (2009)). Approximately one in eight American children will undergo tonsillectomy (Marcus, C. et al., *The New England Journal of Medicine*, 368:2366-76 (2013); Brouillette, R. *The New England Journal of Medicine*, 368:2428-9 (2013)). Morphine is one of the top 10 medications given to children in the inpatient setting (Lasky, T. et al., *Clin. Ther.*, 34:720-727 (2012)) and it is frequently used to manage pain during and after tonsillectomy in children. Obstructive sleep apnea, which is an indication for tonsillectomy, makes children especially sensitive to central depressive effects of opioids including respiratory depression (Brown, K. et al., *Anesthesiology*, 105:665-669 (2006)). A recent study of the largest original reports of post-tonsillectomy mortality demonstrated that the use of opioid pain medications accounted for a preponderance of deaths and anoxic brain injury (Goldman, J. et al., *The Laryngoscope* 123:2544-53 (2013)). In February 2013, the Food and Drug Administration warned against use of codeine (morphine pro-drug) in children undergoing tonsillectomy based on multiple reports of deaths and serious adverse effects irrespective of the CYP2D6 genotype and metabolizing status (Food and Drug Administration, "Safety review update of codeine use in children; new boxed warning and contraindication on use after tonsillectomy and/or adenoidectomy," in FDA Drug Safety Communication 2013.

SUMMARY OF THE INVENTION

The invention provides methods for selecting an analgesic medication for a patient in need of analgesia and methods for identifying a patient at risk of a serious opioid-induced adverse event, the methods comprising determining or receiving the patient's genotype for at least one genetic variant and assigning the patient into one of two risk groups, i.e., a low and high risk group, for a serious opioid-induced adverse event, based at least in part upon the patient's genotype for the at least one genetic variant. In one embodiment, the medication is selected from a non-morphine opioid analgesic or a non-opioid analgesic if the patient is assigned to the high risk group and the medication is selected from morphine or another opioid analgesic if the patient is assigned to the low risk group. In one embodiment, the non-opioid analgesic is selected from the group consisting of paracetamol (also referred to as acetaminophen) and a non-steroidal anti-inflammatory drug (NSAIDs). In one embodiment, the opioid analgesic other than morphine is selected from the group consisting of fentanyl, hydromorphone, codeine, oxycodone, hydrocodone, tramadol, ondansetron, dexamethasone, methadone, alfentanil, and remifentanil. In one embodiment, the patient assigned to the high risk group is identified as a patient at risk for a serious opioid-induced adverse event.

In one embodiment, the at least one genetic variant comprises at least one variant selected from the group consisting of ABCB1 rs9282564, ABCC3 rs4148412, and ABCC3 kgp8560677. In one embodiment, the variants are assigned into one of two risk groups as follows and the serious opioid-induced adverse event is selected from respiratory depression [RD], prolonged stay in recovery due to RD [prolongRD], and post-operative nausea and vomiting [PONV] which may also be refractory PONV:

ABCB1 rs9282564 GG high, AG high, AA low [RD];
ABCC3 rs4148412 AA high, AG high, GG low [prolongRD]; and
ABCC3 kgp8560677 AA high, AG high, GG low [PONV].

In one embodiment, the at least one genetic variant comprises or further comprises at least one variant selected from the group consisting of OPRM1 rs1799971, ABCC3 rs739923, FAAH rs 324420, and ABCB1 rs1045642. In one embodiment, the variants are assigned into one of two risk groups as follows and the serious opioid-induced adverse event is selected from respiratory depression [RD], prolonged stay in recovery due to RD [prolongRD], and post-operative nausea and vomiting [PONV] which may also be refractory PONV:

OPRM1 rs1799971 GG high, AG high, AA low [RD];
ABCC3 rs739923 GG null, AG low, AA low [prolongRD];
FAAH rs324420 AA high, AC high, CC low [PONV]; and
ABCB1 rs1045642 TT high, TC high, CC low [RD].

In one embodiment, the at least one genetic variant comprises at least three variants consisting of FAAH rs2295632, ABCB1 rs1045642, and ADRB2 rs1042713. In one embodiment, the variants are assigned into one of two risk groups as follows and the serious opioid-induced adverse event is respiratory depression [RD]:

FAAH rs2295632 AA high, CA high, CC low;
ABCB1 rs1045642 TT high, TC high, CC low; and
ADRB2 rs1042713 GG high, GA high, AA low.

In accordance with any of the methods described above, the assigning may be performed, and preferably is performed, by a computer implemented method. In one embodiment, the computer implemented method comprises a decision rule. In one embodiment, the computer implemented method comprises encoding the genotypes such that each SNP gives rise to two coupled binary variables. In one embodiment, the assigning is performed by a computer implemented method comprising a decision rule and the decision rule comprises IF [(rs9282564=AA) OR (rs4148412=GG) OR (k 8560677=GG)] THEN RISK=NO (low)
ELSE RISK=YES (high).

In another embodiment, the assigning is performed by a computer implemented method comprising a decision rule and the decision rule comprises IF [(rs2295632=CC) OR (rs1045642=CC) OR (rs1042713=AA)] THEN RISK=NO (low)
ELSE RISK=YES (high).

In one embodiment of the methods described herein, at least one additional non-genetic factor is utilized to refine the assignment of the patient into one of the two risk groups and/or to select a dose of the medication that is other than the standard dose for a subject of the same age, weight, gender, and ethnicity as the patient. In one embodiment, the at least one additional non-genetic factor is selected from gender, race, age, and diagnosis.

In accordance with any of the methods described herein, in one embodiment the patient is a pediatric patient. In one embodiment, the patient is of Caucasian ancestry.

In a particular embodiment, the patient is a female pediatric patient of Caucasian ancestry assigned to the low risk group, and the opioid medication is administered such that the total dose does not exceed 0.15 mg/kg, 0.2 mg/kg, or 0.275 mg/kg.

In one embodiment, the method of selecting an analgesic medication further comprises adjusting the dose of an opiate analgesic for a patient assigned to the low risk group, the method comprising determining or receiving the patient's genotype for at least one additional genetic variant associated with opioid sensitivity. In one embodiment, the at least one additional genetic variant associated with opioid sensitivity is ABCB1 rs2229109. In accordance with this embodiment, the dose of the opiate analgesic is adjusted upward from the standard dose for patients having the ABCB1 rs2229109 CC genotype and the dose is adjusted down for patients having the ABCB1 rs2229109 AA genotype. In one embodiment, the dose is adjusted by 0.04 mg/kg. The standard dose as used herein refers to the dose indicated on the FDA-approved product label for a subject of the patient's age, weight, gender, ethnicity, and/or diagnosis.

In accordance with any of the methods described herein, in one embodiment the patient's genotype is received directly from equipment used in determining the patient's genotype. In one embodiment, the patient's genotype is determined by a method comprising obtaining or receiving a biological sample from the patient, extracting DNA from the sample, and analyzing the DNA to determine the patient's genotype at each genetic variant in the panel. In one embodiment, the DNA is analyzed using a polymerase chain reaction based genotyping platform. In one embodiment, the genotyping platform utilizes a 5' nuclease assay for amplifying and detecting specific genetic variants. In one embodiment, the biological sample is selected from a blood sample and a buccal swab.

The invention also provides diagnostic kits or "bioassay kits". In one embodiment, the bioassay kit comprises the following components (i) a set of sequence-specific forward and reverse primers effective to amplify each of the following SNPs OPRMI rs1799971, ABCB1 rs9282564, ABCB1 rs1045642, and ADRB2 rs1042713; (ii) two labelled DNA probes, each effective to hybridize to a different allele of the SNP; and (iii) a DNA polymerase having 5' nuclease activity. In one embodiment, the bioassay kit comprises the following components (i) a set of sequence-specific forward and reverse primers effective to amplify one or more genetic variants selected from ABCB1 rs9282564, ABCC3 rs4148412, and ABCC3 k 8560677; (ii) two labelled DNA probes, each effective to hybridize to a different allele of the SNP; and (iii) a DNA polymerase having 5' nuclease activity. In one embodiment, the bioassay kit comprises, a bioassay kit of the invention further comprises a set of sequence-specific forward and reverse primers effective to amplify one or more additional genetic variants selected from OPRM1 rs1799971, ABCC3 rs739923, FAAH rs 324420, and ABCB1 rs1045642. In one embodiment, the bioassay kit comprises the following components (i) a set of sequence-specific forward and reverse primers effective to amplify at least three variants consisting of FAAH rs2295632, ABCB1 rs1045642, and ADRB2 rs1042713; (ii) two labelled DNA probes, each effective to hybridize to a different allele of the SNP; and (iii) a DNA polymerase having 5' nuclease activity.

BRIEF DESCRIPTION OF THE DRAWINGS

FIG. 3A. Inter-individual variation in morphine CL and metabolites (M3G/M6G) formation clearances (FCLM3G & FCLM6G) with ABCC3 rs4793665 genotype observed in our studies. The top panel summarized results from the study undergoing adenotonsillectomy while bottom panel summarizes results from the spine surgery. ABCC3 rs4793665 genotype is varied across the x-axis. Empirical Bayesian estimates of individual morphine CL (ηMor,CL), M3G formation CL (ηM3G,FCL) and M6G formation CL (ηM6G,FCL) from the Nonmem analysis are plotted on the y-axis for the left, middle and right panels respectively.

FIG. 4A. Inter-individual variation in morphine CL and metabolites (M3G/M6G) formation clearances (FCLM3G & FCLM6G) with ABCC3 rs739923 genotype observed in our studies. The top panel summarized results from the study undergoing adenotonsillectomy while bottom panel summarizes results from the spine surgery. ABCC3 rs739923 genotype is varied across the x-axis. Empirical Bayesian estimates of individual morphine CL (ηMor,CL), M3G formation CL (ηM3G,FCL) and M6G formation CL (ηM6G,FCL) from the Nonmem analysis are plotted on the y-axis for the left, middle and right panels respectively.

FIG. 5. Inter-individual variation in morphine CL and metabolites (M3G/M6G) formation clearances (FCLM3G & FCLM6G) with ABCC3 rs4148412 genotype observed in our studies. The top panel summarized results from the study undergoing adenotonsillectomy while bottom panel summarizes results from the spine surgery. ABCC3 rs4148412 genotype is varied across the x-axis. Empirical Bayesian estimates of individual morphine CL (ηMor,CL), M3G formation CL (ηM3G,FCL) and M6G formation CL (ηM6G,FCL) from the Nonmem analysis are plotted on the y-axis for the left, middle and right panels respectively.

DETAILED DESCRIPTION OF THE INVENTION

Figure 1:
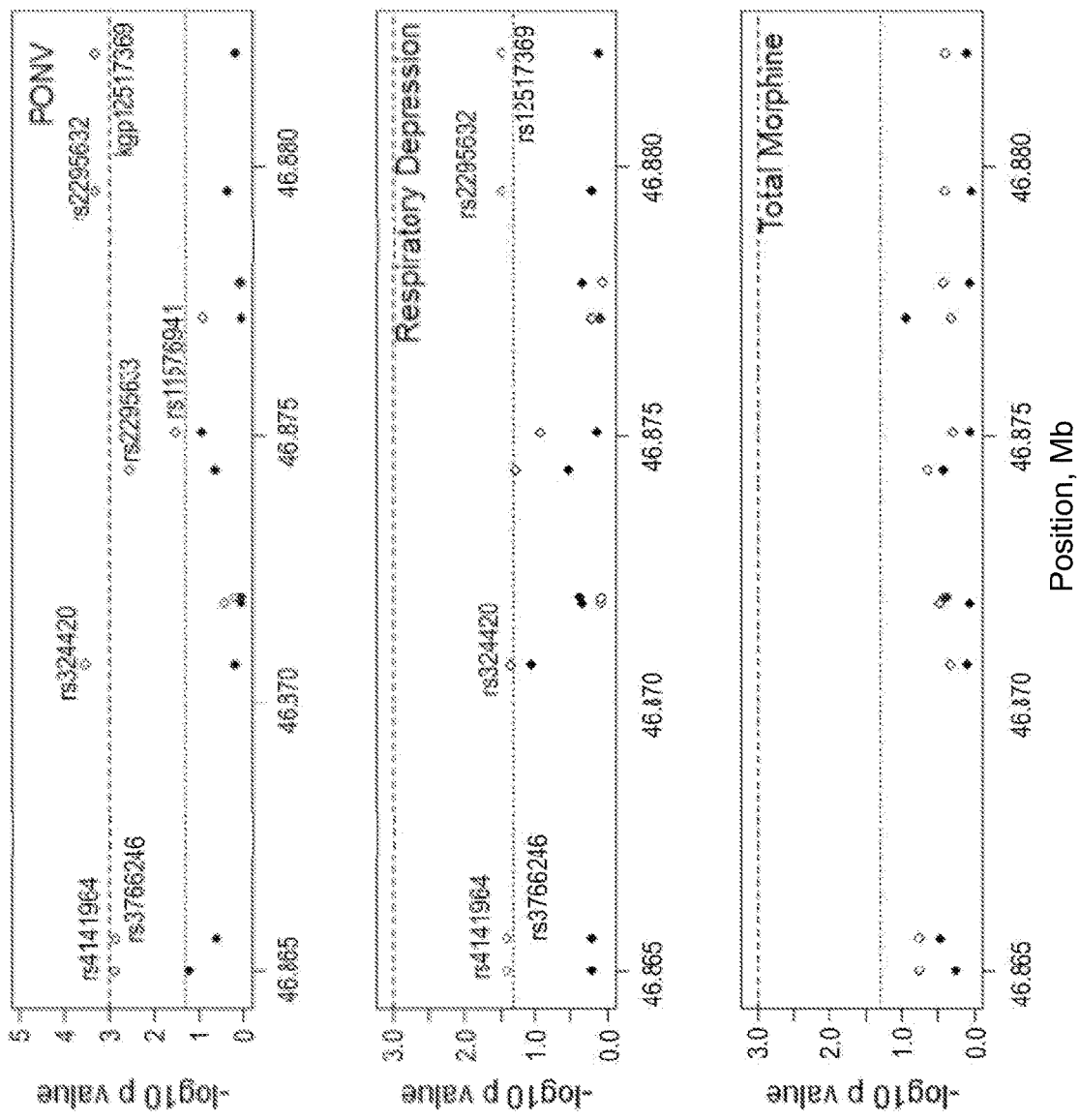
FIG. 1. Expanded region of FAAH from 46.86 Mb to 46.89 Mb where the significantly associated region was identified. There were 11 SNPs tested. The −log 10 (p value) is shown for the single SNP association with PONV (top panel), respiratory depression (middle panel), and total morphine (mg/kg) (bottom panel).

The invention provides methods for selecting an analgesic medication for a patient in need of analgesia and methods for identifying a patient at risk of a serious opioid-induced adverse event, the methods comprising determining or receiving the patient's genotype for at least one genetic variant and assigning the patient into one of two risk groups, i.e., a low and high risk group, for a serious opioid-induced adverse event, based at least in part upon the patient's genotype for the at least one genetic variant. The invention also provides methods for adjusting the dosage of an analgesic medication for a patient in need thereof, the method comprising determining or receiving the patient's genotype for at least one genetic variant and adjusting the dosage of the medication accordingly as described herein. In one embodiment, the analgesic medication is an opioid analgesic. In one embodiment, the opioid analgesic is morphine. In one aspect, the invention provides genetic variants which, either alone or in combination with other genetic variants or non-genetic factors, indicate a higher risk of one or more opioid-related adverse events, or poor pain control, or both, for patients having a particular genotype. In one embodiment, the genetic variant is a single nucleotide polymorphism, or SNP.

The invention also provides decision trees and algorithms incorporating the genetic associations described herein to form predictive models of clinical outcomes useful in providing personalized interventions to both reduce the risk of adverse events and increase analgesic efficacy. These decision trees and algorithms can also be used to evaluate the efficacy and safety of administering opioids and/or analgesics. The use of the decision trees and algorithms described herein can improve perioperative clinical outcomes by providing better analgesia with minimal adverse effects, as well as economic outcomes, by reducing prolonged PACU stays, emergency room visits for inadequate pain control, dehydration following opioid-induced vomiting, and respiratory depression requiring oxygen and intense respiratory support measures. These clinical decision algorithms can enable tailored opioid selection and dosing to maximize pain relief while minimizing the risk of serious adverse events. These findings can be extrapolated to adults and children with surgical or non-surgical pain requiring opioids. Unless otherwise noted, terms are to be understood according to conventional usage by those of ordinary skill in the relevant art.

A "single nucleotide polymorphism," or "SNP," is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI) or identifies the residue change associated with the identified polymorphism.

As used herein, the term "look-up table" is a table that correlates one form of data to another form, or one or more forms of data to a predicted outcome to which the data is relevant, such as a phenotype or trait. For example, a look-up table can comprise a correlation between a genetic variant as described herein and a particular trait or phenotype, e.g., risk of a drug-related adverse event or insufficient drug activity at the standard dose, that an individual who carries the variant is likely to display, or is more likely to display than individuals who do not carry the variant. Look-up tables can be multidimensional, i.e. they can contain information about multiple genetic variants, e.g., alleles, SNPs, gene deletions or insertions, or they can contain information about multiple variants; they can also comprise other non-genetic factors, including patient-specific clinical data such as diagnosis, gender, ethnicity, comorbidity, etc., as well as information about therapeutic options including, for example, therapeutic methods and medications.

As used herein, the term "decision tree" refers to a standard machine learning technique for multivariate data analysis and classification (Hastie, T., et al. *The Elements of Statistical Learning*, Second Edition, Springer (2009); Witten, I. and Frank, E. *Data Mining: Practical Machine Learning Tools and Techniques*, Second Edition, Morgan Kaufmann, San Francisco (2005); Hothorn, T. *Journal of Computational and Graphical Statistics*, 15:651-74 (2010)). Decision trees can be used to derive easily interpretable and intuitive rules for decision support systems.

Embodiments of the invention include use of each genetic variant separately as a diagnostic or prognostic marker, or the use of two or more variants combined into a panel where the panel is a better predictor of the phenotype (e.g., drug-induced or drug-related adverse event or ineffectiveness of drug at a standard dose).

Genetic Variants and Non-Genetic Factors

The invention provides methods for clinical decision support, e.g., methods for selecting an appropriate analgesic medication for a patient in need thereof, as well as methods for identifying a patient who is at risk of a serious drug-induced (or drug-related) adverse event. The methods utilize information about the patient's genotype at particular genetic variants, either alone or in combination with other, genetic or non-genetic factors such as age, gender, ethnicity, comorbidity, diagnosis, etc., to inform the appropriate selection of medications for the patient and to identify patients who are at risk, especially those at high risk, of a serious drug-induced (or drug-related) adverse event.

ATP Binding Cassette B1 (ABCB1) (Also Known as MCR1)

The concentration of morphine in brain is influenced by a P-glycoprotein transporter, ABCB1 at the blood brain barrier. A polymorphism of ABCB1, 3435C>T, has been linked with morphine's blood brain barrier transport activity in adults and the homozygous TT genotype was associated with higher maximum CSF concentrations of morphine than other genotypes (Meineke, I. et al., *British Journal of Clinical Pharmacology*, 54:592-603 (2002)). Previously, the same ABCB1 polymorphism, 3435C>T, has been associated with increased respiratory depression in Korean adults receiving another opioid, fentanyl (Park, H. et al., *Clin. Pharmacol. Ther.*, 81:539-546 (2007)), but whether ABCB1 variants are associated with morphine-induced respiratory depression in children was not known prior to the study described in detail in Example 7. As described in that example, ABCB1 rs9282564 was strongly associated with prolonged PACU stay due to respiratory depression in both Caucasian and African American children (no race specific effect was detected). Thus, ABCB1 rs9282564 GG homozygotes had an increased risk of respiratory depression resulting in prolonged hospital stays. Another clinically relevant association observed in this study was between the ABCB1 rs2229109 and post-operative morphine doses in children who needed rescue dose of morphine in PACU. Each additional copy of the minor allele (A) of ABCB1 rs2229109 decreased post-operative morphine dose by 0.04 mg/kg (95% CI: 0.01-0.07). Thus, ABCB1 rs2229109 CC homozygotes required more morphine when postoperative analgesic interventions were needed while children with the AA genotype are more sensitive to morphine and require less.

ABCC3

Canalicular multispecific organic anion transporter 2 is encoded by the ABCC3 gene which is expressed primarily in the basolateral surface of the hepatocytes (Scheffer, G., et al., *Lab Invest.*, 82:193-201 (2002)) and has been reported to have high affinities for glucuronides including the active metabolites of morphine, M3G and M6G (Zelcer, N. et al., *Proc. Natl. Acad. Sci. U.S.A.*, 102:7274-9 (2005)). Subjects with the −211C>T TT genotype have been reported to have decreased mRNA expression in the liver tissue than CC genotype hypothesized due to the reduced binding of nuclear proteins to the promoter region of the gene (Lang, T. et al., *Pharmacogenetics*, 14:155-64 (2004); Gradhand, U. et al., *Life Sci.*, 80:1490-4 (2007)). As described in detail in Example 2, children with the C/C genotype at ABCC3 rs4793665 had 41 to 46% higher formation of two active metabolites of morphine, indicating that this genotype has a significant effect on the pharmacokinetics of morphine and offering a possible explanation for the lower morphine clearance and higher incidences of adverse effects with morphine in Caucasians compared to African Americans, since this genotype is more frequent in Caucasians. As discussed in Example 3, the pharmacokinetic effects of ABCC3 rs4793665 were confirmed and another ABCC3 variant having significant pharmacokinetic effects was identified. The ABCC3 rs4148412 AA genotype was also found to be associated with higher formation of active metabolites of morphine compared to other genotypes. In addition, a number of ABCC3 variants were identified as significantly associated with clinical outcomes including adverse events (e.g., post-operative nausea and vomiting and prolonged stay in recovery due to respiratory depression) and total morphine requirement. These include, for example, ABCC3 rs4148412, rs739923, and kgp8560677. Others are described in Example 3.

Fatty Acid Amide Hydrolase (FAAH)

Fatty acid amide hydrolase (FAAH) is part of the endocannabinoid system, responsible for anandamide catabolism. Anandamide is a neuromodulator of vomiting. FAAH degrades anandamide, as an endogenous agonist for CB1 receptors. Canniboid agonists are effective antiemetics against opioids through CB1 receptors. As described in detail in Example 1, significant association was detected between PONV and three SNPs (rs324420, rs2295632 and kgp12517369), and between total morphine dose and rs647325 in Caucasian patients. However, in African American patients, only nominal associations were detected for any of the outcomes. In Caucasians, addition of one copy of the minor allele of FAAH rs4141964, FAAH rs3766246, FAAH rs324420, FAAH rs2295632 and FAAH kgp12517369 increased the odds of PONV by 2.42-, 2.42-, 2.73-, 2.61- and 2.61-fold, respectively (P<0.0018). FAAH rs324420 was significantly associated with PONV (P=0.0053) with addition of one copy of minor allele (A) increasing the odds ratio by 2.0-fold; and it was also associated with PONV leading to prolonged PACU stay (P=0.0209) with addition of one copy of minor allele (A) increasing the odds ratio by 2.2-fold. The strong association of FAAH rs324420 with PONV was further validated with larger samples, as discussed in Example 3.

Opioid Receptor µ1 (OPRM1)

The opioid receptor mu 1 (OPRM1) gene which encodes the receptor can be a candidate gene for variation in pain perception and response to opioids (Mogil, J. *Proc. Natl. Adac. Sci. U.S.A.*, 96:7744-51 (1999)). OPRM1 rs1799971 (A118G) results in decreased µ-receptor binding potential in the brain (Ray, R. et al., *Proc. Natl. Acad. Sci. U.S.A.*, 108:9268-73 (2011)). Adult carriers of the GG homozygous genotype can require up to a 2-4 fold higher dose of morphine than AA variants. Example 4 describes the first prospective clinical trial showing that the risk of respiratory depression is higher in carriers of the OPRM1 AA genotype despite their requirement for less morphine compared to carriers of the AG/GG genotypes, and further that the presence of the G allele has a protective effect. This association is useful in identifying children at higher risk of respiratory depression and personalizing the use of morphine in children to maximize pain relief while minimizing the likelihood of serious adverse events.

OCT1

While morphine being a substrate of OCT1 is well characterized, the role of OCT1 in the uptake of its active metabolites described in Example 2 was not previously known. The results presented in Example 2 indicate that the effect of OCT1 on morphine clearance may be much higher than the currently estimated 16%, meaning that homozygous subjects would experience better analgesia but worse adverse reactions in response to morphine dosing.

Obstructive Sleep Apnea (OSA)

Obstructive sleep apnea (OSA) is over-represented among African-American patients, who in turn are more likely to be at a higher risk of inadequate pain relief. OSA and race therefore represent important covariates; this is further highlighted by the finding that ADRB2 and FAAH gene polymorphisms can be used to relatively accurately predict race (with ~80% prediction accuracy). OSA itself also seems to have a relatively strong, although poorly understood, genetic component (Larkin, E. et al. *Resp. Crit. Care Med.* 182:947-53 (2010)). OSA is also an indication for tonsillectomy.

Gender

Although a number of preclinical and experimental studies indicate differences in pain modulation between rodent males and females and also in adult humans in terms of increased pain and opioid sensitivity in females, clinical trials investigating postoperative pain and sex differences are inconsistent. Moreover, the data with sex differences related to opioid analgesics from adult human trials are not sufficient to reliably guide pediatric clinical practice (Hurley R. and Adams M. *Anesth. Analg.*, 107:309-17 (2008)). As discussed in detail in Example 6, a significant sex-specific effect was detected in post-operative nausea and vomiting (PONV, p=0.001) and prolonged PACU stay due to PONV (p=0.010). In girls, probabilities of having these adverse effects increased with the total morphine dose.

Assessment for Markers and Haplotypes

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g. Chen, X. et al., *Genome Res.* 9(5): 492-98 (1999); Kutyavin et al., *Nucleic Acid Res.* 34:e128 (2006)), utilizing PCR, LCR, Nested PCR, and other techniques for nucleic acid amplification. Specific commercial methodologies available for SNP genotyping include, but are not limited to, TaqMan genotyping assays and SNPlex platforms (Applied Biosystems), gel electrophoresis (Applied Biosystems), mass spectrometry (e.g. MassARRAY system from Sequenom), minisequencing methods, real-time PCR, Bio-Plex system (BioRad), CEQ and SNPstream systems (Beckman), array hybridization technology (e.g. Affymetrix GeneChip; Perlegen), BeadArray Technologies (e.g. Illumina GoldenGate and Infinium assays), array tag technology (e.g. Parallele), and endonuclease-based fluorescence hybridization technology (Invader; Third Wave). Thus, by use of these or other methods available to the person skilled in the art, one or more alleles at polymorphic markers, including microsatellites, SNPs, or other types of polymorphic markers, can be identified.

An individual who is at an increased susceptibility (i.e. increased risk) for a disease or trait is an individual in whom at least one specific allele at one or more polymorphic marker or haplotype conferring increased susceptibility (increased risk) for the disease or trait is identified (i.e. at-risk marker alleles or haplotypes). The at-risk marker or haplotype is one that confers an increased risk (increased susceptibility) of the disease. In some embodiments, significance associated with a marker or haplotype is measured by a relative risk (RR). In some embodiments, significance associated with a marker or haplotype is measured by an odds ratio (OR). In a further embodiment, the significance is measured by a percentage.

An at-risk polymorphic marker or haplotype as described herein is one where at least one allele of at least one marker or haplotype is more frequently present in an individual at risk for a trait, for example, at risk for inadequate pain relief or adverse effects (e.g., post-operative nausea and vomiting, which may be refractory, respiratory depression, and prolonged stay in recovery due to respiratory depression) from analgesics, especially opioids, particularly during treatment for perioperative pain, compared to the frequency of its presence in a comparison group (control), such that the presence of the marker or haplotype is indicative of susceptibility to the trait. In some embodiments, the control group can be a population sample, i.e. a random sample from the general population. In some embodiments, the control group is characterized by the absence of one or more additional non-genetic risk factors, for example gender, age, and race. In some embodiments, the risk factors comprise at least one additional genetic risk factor.

In some embodiments of the invention, an individual who is at a decreased susceptibility (i.e. at a decreased risk) for a trait is an individual in whom at least one specific allele at one or more polymorphic marker or haplotype conferring decreased susceptibility is identified. The marker alleles and/or haplotypes conferring decreased risk are also said to be protective. In some embodiments, the protective marker or haplotype is one that confers a significant decreased risk (or susceptibility) a trait.

The person skilled in the art will appreciate that for markers with two alleles present in the population being studied (such as SNPs), and wherein one allele is found in increased frequency in a group of individuals with a trait in the population, compared with controls, the other allele of the marker will be found in decreased frequency in the group of individuals with the trait, compared with controls. In such a case, one allele of the marker (the one found in increased frequency in individuals with the trait) will be the at-risk allele, while the other allele will be a protective allele.

A genetic variant associated with a trait can be used alone to predict the risk of the disease for a given genotype. For a biallelic marker, such as an SNP, there are three possible genotypes: homozygote for the at-risk variant, heterozygote, and non-carrier of the at-risk variant. Risk associated with variants at multiple loci can be used to estimate overall risk. For multiple SNP variants, there are k possible genotypes, with $k=3^n \times 2^p$; where n is the number autosomal loci, and p the number of gonosomal (sex chromosomal) loci. Overall risk assessment calculations for a plurality of risk variants typically assume that the relative risks of different genetic variants multiply, i.e. the overall risk (e.g. RR or OR) associated with a particular genotype combination is the product of the risk values for the genotype at each locus. If the risk presented is the relative risk for a person or a specific genotype for a person, compared to a reference population with matched gender and ethnicity, then the combined risk is the product of the locus-specific risk values and which also corresponds to an overall risk estimate compared with the population. If the risk for a person is based on a comparison to non-carriers of the at-risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e. non-carriers) of 1.0 but has an overall risk, compared with the population, of less than 1.0. It should be noted that the group of non-carriers can potentially be very small, especially for a large number of loci, and, in that case, its relevance is correspondingly small.

The multiplicative model is a parsimonious model that usually fits the data of complex traits reasonably well. Deviations from multiplicity have been rarely described in the context of common variants for common diseases and if reported are usually only suggestive, since very large sample sizes are typically required to be able to demonstrate statistical interactions between loci.

By way of example, consider a total of eight variants that have been described to associate with prostate cancer (Gudmundsson, et al., *Nat Genet* 39:631-7 (2007); Gudmundsson, et al., *Nat Genet* 39:977-83 (2007); Yeager, et al., *Nat Genet* 39:645-49 (2007); Amundadottir, et al., *Nat Genet* 38:652-8 (2006); Haiman, et al., *Nat Genet* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare but are still possible, and these can be considered for overall risk assessment. The multiplicative model applied in the case of multiple genetic variants can also be valid in conjugation with non-genetic risk variants, assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with adverse anesthetic effects can be assessed, including combinations of any one of the markers and/or polymorphisms as disclosed herein or markers in linkage disequilibrium therewith.

Risk Calculations

The creation of a model to calculate the overall genetic risk involves two steps: i) conversion of odds-ratios for a single genetic variant into relative risk, and ii) combination of risk from multiple variants in different genetic loci into a single relative risk value.

Deriving Risk from Odds-Ratios

Most gene discovery studies for complex diseases or traits that have been published to date in authoritative journals have employed a case-control design due to their retrospective setup. These studies sample and genotype a selected set of cases (people who have the specified disease condition) and control individuals. The interest is in genetic variants (alleles) whose frequency in cases and controls differ significantly.

The results are typically reported in odds ratios, which describe the ratio between the fraction (probability) with the risk variant (carriers) versus the non-risk variant (non-carriers) in the groups of affected versus the controls, i.e. expressed in terms of probabilities conditional on the affection status:

$$OR=(Pr(c|A)/Pr(nc|A))/(Pr(c|C)/Pr(nc|C))$$

In some embodiments, the absolute risk for the disease or trait is what is determined, i.e. the fraction of those individuals carrying the risk variant who get the disease or, in other words, the probability of getting the disease. This number cannot be directly measured in case-control studies, in part because the ratio of cases versus controls is typically not the same as that in the general population. However, under certain assumptions, the risk can be calculated from the odds ratio value.

Combining the Risk from Multiple Markers

When genotypes of many SNP variants are used to estimate the risk for an individual, unless otherwise stated, a multiplicative model for risk can be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A) \text{ and } Pr(g|,g2)=Pr(g1)Pr(g2)$$

In embodiments where markers are closely spaced on the genome, i.e. are in linkage disequilibrium such that the concurrence of two or more risk alleles is correlated, a haplotype modeling where the odds-ratios are defined for all allele combinations of the correlated SNPs can be employed.

As an example, consider an individual who has the following genotypes at four markers associated with risk of type-2 diabetes along with the risk relative to the population at each marker:

Chromo 3 PPARG CC Calculated risk: RR(CC)=1.03
Chromo 6 CDKAL1 GG Calculated risk: RR(GG)=1.30
Chromo 9 CDKN2A AG Calculated risk: RR(AG)=0.88
Chromo 11 TCF7L2 TT Calculated risk: RR(TT)=1.54

Combined, the overall risk relative to the population for this individual is: 1.03×1.30×0.88×1.54=1.81.

Risk Assessment

Embodiments of the invention can be directed to methods of assessing a sample comprising genomic DNA from an individual for the presence of variants described herein to be associated with adverse drug reactions, specifically opioids and morphine in particular. Such methods typically comprise steps that detect the presence or absence of at least one allele of at least one polymorphic marker, using methods well-known to the skilled person and further described herein, and, based on the outcome of such assessment, determine whether the individual from whom the sample is derived is at increased or decreased risk (increased or decreased susceptibility) of adverse anesthetic effects. In some embodiments, detecting particular alleles of polymorphic markers can be carried out by obtaining nucleic acid sequence data about a particular human individual that identifies at least one allele of at least one polymorphic marker. Different alleles of the at least one marker are associated with different susceptibility to such effects in humans. Obtaining nucleic acid sequence data can comprise identifying the nucleic acid sequence at a single nucleotide position, which is sufficient to identify alleles at SNPs. The nucleic acid sequence data can also comprise sequence information at any other number of nucleotide positions, in particular for genetic markers that comprise multiple nucleotide positions, and can be anywhere from two to hundreds of thousands, possibly even millions, of nucleotides (in particular, in the case of CNVs).

In some embodiments, the methods comprise utilization of a dataset comprising information about the genotype status of at least one polymorphic marker associated with a disease or trait (or markers in linkage disequilibrium with at least one marker associated with the disease or trait). In other words, a dataset containing information about such genetic status, for example in the form of sequence data, genotype counts at a certain polymorphic marker, or a plurality of markers (e.g. an indication of the presence or absence of certain at-risk alleles), or actual genotypes for one or more markers, can be queried for the presence or absence of certain at-risk alleles at certain polymorphic markers as disclosed herein to be associated with the disease or trait. A positive result for a variant (e.g. marker allele) associated with the disease or trait is indicative of the individual from whom the dataset is derived is at increased susceptibility (increased risk) of the disease.

In some embodiments, a polymorphic marker is correlated to a disease or trait by referencing genotype data for the polymorphic marker to a look-up table that comprises correlations between at least one allele of the polymorphism and the disease. In some embodiments, the table comprises a correlation for one polymorphism. In some embodiments, the table comprises a correlation for a plurality of polymorphisms. By referencing to a look-up table that gives an indication of a correlation between a marker and the disease, a risk for the disease or trait or a susceptibility to the disease or trait can be identified in the individual from whom the sample is derived. In some embodiments, the correlation is reported as a statistical measure. The statistical measure can be reported as a risk measure, such as a relative risk (RR), an absolute risk (AR), or an odds ratio (OR).

The markers described herein can be useful for risk assessment and diagnostic purposes, either alone or in combination. The results of the risk of suffering adverse anesthetic effects based on the markers described herein can also be combined with data for other genetic markers or risk factors for adverse anesthetic effects to establish an overall risk. Thus, even in cases where the increase in risk by individual markers is relatively modest, e.g. on the order of 10-30%, the association can have significant implications. Thus, relatively common variants can have significant contribution to the overall risk (population attributable risk is high), or combinations of markers can be used to define groups of individuals who, based on the combined risk of the markers, are at significant combined risk of developing complications due to adverse anesthetic effects.

Thus, in some embodiments, a plurality of variants (genetic markers, biomarkers, and/or haplotypes) is used for overall risk assessment. In some embodiments, these variants can be selected from the variants as disclosed herein. In some embodiments, the use of the variants as disclosed herein in combination with other variants known to be useful for diagnosing a susceptibility to adverse anesthetic effects is used. In such embodiments, the genotype status of a plurality of markers and/or haplotypes is determined in an individual, and the status of the individual is compared with the population frequency of the associated variants or the frequency of the variants in clinically healthy subjects, such as age-matched and sex-matched subjects. Methods known in the art, such as multivariate analyses or joint risk analyses or other methods known to the skilled person, can subsequently be used to determine the overall risk conferred based on the genotype status at the multiple loci. Assessment of risk based on such analysis can subsequently be used in the methods, uses, and kits of the invention, as described herein.

Individuals who are homozygous for at-risk variants for suffering adverse anesthetic effects can be at particularly high risk of developing such effects. This is due to the dose-dependent effect of at-risk alleles, such that the risk for homozygous carriers is generally estimated as the risk for each allelic copy squared.

For the SNP markers described herein, the opposite allele to the allele found to be in excess in patients (at-risk allele) is found in decreased frequency in situations where adverse effects from anesthetic and analgesic agents are observed. These markers and haplotypes in LD and/or comprising such markers along with other factors, including age, race, weight (or body mass index, BMI), are thus protective for adverse anesthetic and analgesic effects, i.e. they confer a decreased risk or susceptibility of individuals carrying these markers and/or haplotypes developing pain and/or adverse effects from anesthetics and analgesics.

In some embodiments, variants as disclosed herein, including certain haplotypes, can comprise a combination of various genetic markers, e.g. SNPs and microsatellites. Detecting haplotypes can be accomplished by methods known in the art and/or described herein for detecting sequences at polymorphic sites. Furthermore, correlation between certain haplotypes or sets of markers and disease phenotypes can be verified using standard techniques. A representative example of a simple test for correlation would be a Fisher-exact test on a two by two table.

Predictive Models

A decision tree is a standard machine learning technique for multivariate data analysis and classification that can be used to derive easily interpretable and intuitive rules for decision support systems. Decision tress can be viewed as a recursive partitioning approach, in which data is hierarchically divided into strata by simple logical rules. The advantage of decision trees is their simplicity, ability to handle categorical and numerical variables, as well as missing values, robustness to outliers and scaling, and the ability to combine feature selection with stratification and classification. Decision trees can also be used to derive easy to interpret and intuitive rules for decision support systems.

Decision trees are used to select and combine the most predictive SNPs with demographic, clinical, and other input features into simple logical rules that can be used to classify patients and predict adverse effects, thereby enabling robust and accurate point-of-care prediction of inadequate pain relief and opioid-related adverse effects. Such knowledge allows for individualized treatment.

The observed distinct strata and complex interaction patterns have resulted in the systematic determination of whether interactions of specific polymorphisms of genes, such as those involved in opioid transport, sensing, and metabolism, significantly influence morphine's adverse effects in children. Due to the limitations of current approaches, there is a need for tailored solutions and extensions that can provide more robust and accurate decision rules for personalized interventions.

Distinct strata associated with specific patterns of gene-gene interactions in the context of adverse effects, pain sensitivity, and other clinical phenotypes were identified and analyzed first using standard recursive partitioning (or decision tree-based) approaches, such as CART. Genotyping, demographic, and relevant clinical data were then combined to derive logical rules for the prediction of patients with high vs. low risk of adverse effects, including opioid-induced respiratory depression outcomes. The predictive power of such models is limited by inherent biological noise, limited sample sizes, and complex pattern of interactions representing multiple mechanisms that can lead to variation in molecular and eventually clinical outcomes. Weaker associations that can manifest themselves only in the context of specific strata can be present as well but are more difficult to detect.

Decision trees and associated logical rules were enhanced by incorporating allelic (additive), dominant, and recessive models, as well as ternary trees wherein each genotype value decoupled were also implemented to facilitate identification and analysis of distinct strata. In addition, haplotype reconstruction for each gene (strong patterns of LD are observed for several genes included here) was incorporated, using Phase and similar population-based models, allowing for the simplification of decision rules and accounting for many implicit interactions observed in the data. Classical decision trees, support vector machines (SVMs), and hierarchical mixtures of experts (HME) models were integrated.

The HME approach can be viewed as a probabilistic decision tree (see Hasti et al., chapter 9 and references therein). In an exemplary HME decision tree, the terminal nodes are called "experts" (or expert networks) that provide individual (and context-dependent) prediction of the response (e.g., adverse effects). These individual predictions are combined by the decision models ("gating networks") of the non-terminal nodes. Typically, a linear or logistic regression model is fit in each terminal node, using a linear combination of inputs, as for example in the following model for objective postoperative pain score (P) as a function of genes and other predictors:

$$E(P|X) = \beta 0 + \beta 1 Age + \beta 2 Sex + \beta 3 Race + \beta 4 GCH1 + \beta 5 COMT + \beta 6 ABCB1 + \text{Other Factors}$$

In the above equation, E(Y|X) denotes the expected value of Y given a vector of predictor variables (features) X. Expert models can be generalized using other suitable classification (or regression) approaches, such as by using robust linear SVM predictors. In this approach, terminal SVM models can be regarded as an ensemble of expert classifiers that are optimized in a context-dependent manner (including one-class SVMs when applicable).

This can be compared with developing an ensemble of classifiers optimized on different subsets of the data (such as in the context of cross-validation), which are combined to provide more robust results and associated confidence levels (which are defined in terms of consistency within the ensemble). Here, such subsets were defined by robust distinct strata obtained using standard decision trees (possibly with re-sampling and boosting as well). Thus, the tree topology of such an extended HME model would be expected to represent stable strata identified in the original decision tree analysis, addressing one of the limitations of the HME approach, namely the lack of methods for finding a good tree topology. Therefore, the resulting tree preserves the ease of interpretation of the decision rules, while improving accuracy.

Other standard statistical and machine learning methods, including neural networks, prototype, and kernel-based approaches, were also applied to further dissect patterns of gene-gene interactions and to assess their predictive power (and to evaluate relative merits of the new approach). Cross-validation, in which the overall training cohort is repeatedly (and randomly) divided into training and validation subsets, was used to evaluate the accuracy and to assess the stability of the resulting decision rules and observed strata. Standard measures of accuracy, including overall classification accuracy, precision, recall, and area under ROC curve, were used to evaluate the accuracy of the decision rules based on the proposed mixed recursive partitioning models.

Addressable Populations

In a general sense, the methods and kits of the invention can be utilized from samples containing nucleic acid material (DNA or RNA) from any source and from any individual or from genotype data derived from such samples. In some embodiments, the individual is a human individual. The individual can be an adult, child, or fetus. The nucleic acid source can be any sample comprising nucleic acid material, including biological samples, or a sample comprising nucleic acid material derived therefrom. Embodiments of the invention also provide for assessing markers and/or haplotypes in individuals who are members of a target population. Such a target population is in one embodiment a population or group of individuals at risk of developing adverse anesthetic effects, based on other parameters such as, for example, genetic factors, biomarkers, biophysical parameters, history of anesthesia-related complications, allergic reactions to anesthesia, family history of anesthesia-related complications, and the like.

In some embodiments, the target population includes individuals from specific age subgroups, such as those under the age of 18, under the age of 16, or under the age of 12 or 10. The individuals can be of either sex, males or females.

It is believed that the markers found to be associated with adverse analgesia, and/or opioid effects as disclosed herein can show similar association in other human populations outside of the population employed in the current study. In some embodiments, the human subjects are from one or more human populations or ethnic groups, including, but not limited to, Caucasian populations, European populations, American populations, Eurasian populations, Asian populations, Central/South Asian populations, East Asian populations, Middle Eastern populations, African populations, Hispanic populations, and Oceanian populations.

The racial contribution in individual subjects can also be determined by genetic analysis. Genetic analysis of ancestry can be carried out using unlinked microsatellite markers such as those set out in Smith et al. (*Am J Hum Genet* 74, 1001-13 (2004)).

Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3$^{rd}$ ed., Cold Spring Harbor Laboratory Press (Cold Spring Harbor, N.Y. 2001) provide one skilled in the art with a general guide to many of the terms used in the present application.

One skilled in the art will recognize many methods and materials similar or equivalent to those described herein, which can be used in the practice of the present invention. Indeed, the present invention is in no way limited to the methods and materials described.

Diagnostic Methods

In embodiments of the invention, methods of evaluating, or aiding in the evaluation of, a patient at risk for suffering adverse effects from administered anesthetic, analgesia, and/or opioid, are provided, the methods comprising detecting particular alleles at genetic markers that are correlated with such effects. In some embodiments, methods to determine susceptibility to developing adverse effects to administered anesthetic, analgesia, and/or opioid are provided, the methods comprising detecting at least one allele of at least one polymorphic marker (e.g. the markers described herein). As disclosed herein, particular alleles of particular markers or haplotypes are indicative of a susceptibility to suffering adverse effects from administered analgesia. Prognostic or predictive assays for evaluating a patient's risk or susceptibility to such effects can also be used to develop a customized anesthetic protocol for a subject prior to and during procedures that involve administration of anesthetic, analgesic, and/or opioid.

In some embodiments, methods of identifying a patient at risk for suffering adverse effects from administered anesthetic, analgesia, and/or opioid are carried out by analyzing samples for the presence of absence of at least one polymorphism associated with pain perception, persistent post-operative/chronic pain, and/or anesthetic-, analgesic-, and/or opioid-related adverse effects using microarray or gene chip technology, wherein the microarray or gene chip comprises the at least one polymorphism.

In some embodiments, the gene chip comprises a low density array.

In some embodiments, the methods include evaluation of additional clinical information to tailor pain therapy and anesthesia and minimize anesthetic and analgesic medication-related adverse effects. In some embodiments, the methods include evaluation of additional clinical information to tailor pain therapy and opioids and minimize opioid and analgesic medication-related adverse effects. Additional clinical information for use in such methods include, but are not limited to, patient age, race, weight (or BMI), sleep disordered breathing, gender, allergies, sensitivities, or medical conditions that affect administrative routes for delivered anesthetic, analgesia, and/or opioid. Other factors, such as, for example, ethnicity, medical history, drug interactions, psychological anxiety, stress level, and lifestyle can also be evaluated as part of the methods.

Embodiments of the invention are also directed to using recursive partitioning and decision trees to analyze genotype-phenotype associates and to identify putative strata with distinct patterns of interactions between genes and other non-genetic variables.

In embodiments of the invention, the methods comprise obtaining a sample containing genomic DNA from an individual for analysis. The sample can be, for example, a buccal swab, a saliva sample, a blood sample, or other suitable samples containing genomic DNA, as disclosed herein, and the like. The genomic DNA can be analyzed using any common technique available to the skilled person, such as, for example, high-throughput or low density array technologies, and the like. Results from such genotyping can subsequently be analyzed for the presence of certain variants known to be susceptibility variants for a particular condition, such as the genetic variants disclosed herein. Calculating risk conferred by a particular genotype for the individual can be based on comparing the genotype of the individual to previously determined risk (expressed as a relative risk (RR) or an odds ratio (OR), for example) for the genotype, for example for a heterozygous carrier of an at-risk variant for a particular condition or trait (such as for adverse effects from administered anesthesia). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. In some embodiments, using the population average can be more convenient, since it provides a measure which is easy to interpret for the user, i.e. a measure that gives the risk for the individual, based on his/her genotype, compared with the average in the population.

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

The detection of the particular genetic marker alleles that make up particular haplotypes in the sample can be performed by a variety of methods as described herein and/or known in the art. For example, genetic markers can be detected at the nucleic acid level (e.g. by direct nucleotide sequencing or by other genotyping means known to the skilled in the art) or at the amino acid level if the genetic marker affects the coding sequence of a protein (e.g. by protein sequencing or by immunoassays using antibodies that recognize such a protein). The marker alleles or haplotypes disclosed herein correspond to fragments of genomic segments (e.g. genes) associated with development of adverse effects of administered anesthetic, analgesia, and/or opioid. Such fragments encompass the DNA sequence of the polymorphic marker or haplotype in question but can also include DNA segments in strong LD (linkage disequilibrium) with the marker or haplotype. In some embodiments, such segments comprise segments in LD with the marker or haplotype as determined by a value of $r2$ greater than 0.2 and/or |D'|>0.8).

In some embodiments, determination of susceptibility of developing adverse effects of administered anesthesia can be carried out using hybridization methods. (See *Current Protocols in Molecular Biology*, Ausubel, F. et al., eds., John Wiley & Sons, including all supplements). The presence of a specific marker allele can be indicated by sequence-specific hybridization of a nucleic acid probe specific for the particular allele. The presence of more than one specific marker allele or a specific haplotype can be indicated by using several sequence-specific nucleic acid probes, each being specific for a particular allele. A sequence-specific probe can be directed to hybridize to genomic DNA, RNA, or cDNA. A "nucleic acid probe" can be a DNA probe or an RNA probe that hybridizes to a complementary sequence. One of skill in the art would know how to design such a probe such that sequence specific hybridization will occur only if a particular allele is present in a genomic sequence from a test sample. The invention can also be reduced to practice using any convenient genotyping method, including commercially available technologies and methods for genotyping particular polymorphic markers.

A hybridization sample can be formed by contacting the test sample containing an anesthesia adverse effect-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule or a portion thereof, such as an oligonucleotide of at least 15, 30, 50, 100, 250, or 500 nucleotides in length that is sufficient to specifically hybridize under stringent conditions to appropriate mRNA or genomic DNA. Hybridization can be performed by methods well-known to the person skilled in the art (see, e.g., *Current Protocols in Molecular Biology*, Ausubel, F. et al., eds., John Wiley & Sons, including all supplements). In some embodiments, hybridization refers to specific hybridization, i.e. hybridization with no mismatches (exact hybridization). In some embodiments, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers as disclosed herein, or markers that make up a haplotype as disclosed herein, or multiple probes can be used concurrently to detect more than one marker allele at a time. A single probe can also be designed in which the probe contains more than one marker allele of a particular haplotype (e.g. a probe containing alleles complementary to 2, 3, 4, 5, or all of the markers that make up a particular haplotype). Detection of the particular markers of the haplotype in the sample is indicative that the source of the sample has the particular haplotype (e.g. a haplotype) and therefore is susceptible or at risk of suffering adverse effects from administered anesthesia.

The detection probe can be of any suitable size, although preferably the probe is relatively short. In some embodiments, the probe is from 5-100 nucleotides in length. In some embodiments, the probe is from 10-50 nucleotides in length. In some embodiments, the probe is from 12-30 nucleotides in length. Other lengths of the probe are also contemplated and within the scope of the skill of the average person skilled in the art.

In some embodiments, the DNA template containing the SNP polymorphism is amplified by polymerase chain reaction (PCR) prior to detection. In such embodiments, the amplified DNA serves as the template for a detection probe and an enhancer probe.

In some embodiments, the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example, for increasing the melting temperature in regions containing a low percentage of G or C bases, in which modified A with the capability of forming three hydrogen bonds to its complementary T can be used, or for decreasing the melting temperature in regions containing a high percentage of G or C bases, for example, by using modified G bases that form only two hydrogen bonds to their complementary C base in a double-stranded DNA molecule. In some embodiments, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In some embodiments, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T, or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are correlated with adverse effects of administered anesthesia. Hybridization of the PNA probe is thus diagnostic for susceptibility to such effects.

Embodiments of the invention are also directed to detecting SNPs within a set of genes, methods of detection include but are not limited to, for example, use of SNP microarrays, gene chips, dynamic allele-specific hybridization, molecular beacons, restriction fragment length polymorphism (RFLP)-based methods, PCR-based methods, flap endonuclease-based methods, primer extension, 5'-nuclease-based methods, oligonucleotide ligase assays, single strand conformation polymorphism methods, temperature gradient gel electrophoresis, denaturing high performance liquid chromatography, high-resolution melting analysis, DNA mismatch-binding methods, capillary electrophoresis, and next-generation sequencing methods, and the like.

In embodiments of the invention, a test sample containing genomic DNA obtained from the subject is collected, and PCR is used to amplify a fragment comprising one or more markers or haplotypes of the present invention. As disclosed herein, identification of a particular marker allele or haplotype can be accomplished using a variety of methods (e.g. sequence analysis, analysis by restriction digestion, specific hybridization, single-stranded conformation polymorphism assays (SSCP), electrophoretic analysis, and the like). In some embodiments, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s). Further, the expression of the variant(s) can be quantified as physically or functionally different.

In some embodiments, the DNA template can be amplified by means of whole genome amplification (WGA) methods prior to assessment for the presence of specific polymorphic markers as described herein. Standard methods well-known to the skilled person for performing WGA can be utilized and are within scope of the invention.

In some embodiments, analysis by restriction digestion can be used to detect a particular allele if the allele results in the creation or elimination of a restriction site relative to a reference sequence. RFLP analysis can be conducted, e.g. as described in Current Protocols in Molecular Biology, supra. The digestion pattern of the relevant DNA fragment indicates the presence or absence of the particular allele in the sample.

Sequence analysis can also be used to detect specific alleles or haplotypes. Accordingly, in some embodiments, determination of the presence or absence of a particular marker allele or haplotype comprises sequence analysis of a test sample of DNA or RNA obtained from a subject or individual. PCR or other appropriate methods can be used to amplify a portion of a nucleic acid that contains a polymorphic marker or haplotype, and the presence of specific alleles can then be detected directly by sequencing the polymorphic site (or multiple polymorphic sites in a haplotype) of the genomic DNA in the sample.

In some embodiments, arrays of oligonucleotide probes that are complementary to target nucleic acid sequence segments from a subject can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light-directed synthesis methods that incorporate a combination of photolithographic methods and solid phase oligonucleotide synthesis methods, or by other methods known to the person skilled in the art (see, e.g., Bier, et al. *Adv Biochem Eng Biotechnol* 109:433-53 (2008); Hoheisel, J. D., *Nat Rev Genet.* 7:200-10 (2006); Fan, et al. *Methods Enzymol* 410:57-73 (2006); Raqoussis, J. and Elvidge, G., *Expert Rev Mol Diagn* 6:145-52 (2006); and Mockler, et al. *Genomics* 85:1-15 (2005), each of which is incorporated herein by reference in its entirety). Many additional descriptions of the preparation and use of oligonucleotide arrays for detection of polymorphisms can be found, for example, in U.S. Pat. Nos. 6,858,394, 6,429,027, 5,445,934, 5,700,637, 5,744,305, 5,945,334, 6,054,270, 6,300,063, 6,733,977, 7,364,858, EP 619 321, and EP 373 203, each of which is incorporated herein by reference in its entirety.

Other methods of nucleic acid analysis that are available to those skilled in the art can be used to detect a particular allele at a polymorphic site. Representative methods include, for example, direct manual sequencing (Church and Gilbert, *Proc. Natl. Acad. Sci. USA,* 81: 1991-1995 (1988); Sanger, et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCPs); clamped denaturing gel electrophoresis (CDGE); denaturing gradient gel electrophoresis (DGGE) (Sheffield, et al., *Proc. Natl. Acad. Sci. USA,* 86:232-236 (1989)), mobility shift analysis (Orita, et al., *Proc. Natl. Acad. Sci. USA,* 86:2766-2770 (1989)), restriction enzyme analysis (Flavell, et al., *Cell,* 15:25-41 (1978); Geever, et al., *Proc. Natl. Acad. Sci. USA,* 78:5081-5085 (1981)); heteroduplex analysis; chemical mismatch cleavage (CMC) (Cotton, et al., *Proc. Natl. Acad. Sci. USA,* 85:4397-4401 (1985)); RNase protection assays (Myers, et al., *Science,* 230:1242-1246 (1985); use of polypeptides that recognize nucleotide mismatches, such as *E. coli* mutS protein; and allele-specific PCR, and the like. One of skill in the art can recognize other techniques that can be used for these purposes.

In embodiments of the invention, a determination of a susceptibility or risk of developing adverse effects to administered anesthesia, analgesic, and/or opioid can be made by examining expression and/or composition of a polypeptide encoded by a nucleic acid associated with adverse effects to administered anesthesia in those instances where the genetic marker(s) or haplotype(s) as disclosed herein result in a change in the composition or expression of the polypeptide. Thus, determination of a susceptibility to developing adverse effects to administered anesthesia, analgesic, and/or opioid can be made by examining expression and/or composition of one of these polypeptides or another polypeptide encoded by a nucleic acid associated with development of adverse effects to administered anesthesia, in those instances where the genetic marker or haplotype of the present invention results in a change in the composition or expression of the polypeptide.

A variety of methods can be used for detecting protein expression levels, including, for example, enzyme linked immunosorbent assays (ELISA), Western blots, immunoprecipitations, and immunofluorescence, and the like. A test sample from a subject can be assessed for the presence of an alteration in the expression and/or an alteration in composition of the polypeptide encoded by a particular nucleic acid. An alteration in the expression of a polypeptide encoded by the nucleic acid can be, for example, an alteration in the quantitative polypeptide expression (i.e. the amount of polypeptide produced). An alteration in the composition of a polypeptide encoded by the nucleic acid is an alteration in the qualitative polypeptide expression (e.g. expression of a mutant polypeptide or of a different splicing variant). In some embodiments, determination of a susceptibility to developing adverse effects to administered anesthesia is carried out by detecting a particular splicing variant encoded by a nucleic acid associated with development of such adverse effects or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g. is from the same type of cells) and is from a subject who is not affected by and/or who does not have a susceptibility to development of adverse effects to administered anesthesia. In some embodiments, the control sample is from a subject that does not possess a marker allele or haplotype associated with development of adverse effects to administered anesthesia, as disclosed herein. Similarly, the presence of one or more different splicing variants in the test sample or the presence of significantly different amounts of different splicing variants in the test sample, as compared with the control sample, can be indicative of a susceptibility to developing adverse effects to administered anesthesia. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g. David et al., U.S. Pat. No. 4,376,110), such as immunoblotting (see, e.g., *Current Protocols in Molecular Biology*, particularly chapter 10, supra).

For example, in some embodiments, an antibody (e.g. an antibody with a detectable label) that is capable of binding to a polypeptide encoded by a nucleic acid associated with development of adverse effects to administered anesthesia can be used. Antibodies can be polyclonal or monoclonal. An intact antibody or a fragment thereof (e.g. Fv, Fab, Fab', $F(ab')_2$) can be used. The term "labeled," with regard to the probe or antibody, encompasses direct labeling of the probe or antibody by coupling (i.e. physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g. a fluorescently-labeled secondary antibody) and end-labeling of a DNA probe with biotin such that it can be detected with fluorescently-labeled streptavidin.

In some embodiments, the level or amount of a polypeptide in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid and is diagnostic for a particular allele or haplotype responsible for causing the difference in expression. Alternatively, the composition of the polypeptide in a test sample is compared with the composition of the polypeptide in a control sample. In some embodiments, both the level or amount and the composition of the polypeptide can be assessed in the test sample and in the control sample.

In some embodiments, determination of a susceptibility to developing adverse effects to administered anesthesia is made by detecting at least one marker or haplotype as disclosed herein, in combination with an additional protein-based, RNA-based, or DNA-based assay. In some embodiments, determination of a susceptibility to inadequate pain relief or sensitivity is made by detecting at least one marker or haplotype as disclosed herein, in combination with an additional protein-based, RNA-based, or DNA-based assay. In some embodiments, determination of a susceptibility to OSA is made by detecting at least one marker or haplotype as disclosed herein, in combination with an additional protein-based, RNA-based, or DNA-based assay. In some embodiments, determination of a susceptibility to developing adverse effects to administered anesthesia, analgesic, and/or opioid is made by determining incidence of OSA made by detecting at least one marker or haplotype as disclosed herein, in combination with an additional protein-based, RNA-based, or DNA-based assay.

In some embodiments, determination of a susceptibility to developing adverse effects to an administered opioid is made by detecting at least one marker or haplotype as disclosed herein, in combination with an additional protein-based, RNA-based, or DNA-based assay. In some embodiments, the administered opioid is morphine. In some embodiments, the administered opioid is codeine. In some embodiments, characterization of the OCT1 genotype is used to determine susceptibility to developing adverse effects to an administered opioid. In some embodiments, the UGT2B7 rs7438135 allele is determined. In some embodiments, the rs622342 allele is characterized.

Kits

Kits useful in the methods of the invention comprise components useful in any of the methods disclosed herein, including, for example, primers for nucleic acid amplification, hybridization probes, restriction enzymes (e.g. for RFLP analysis), allele-specific oligonucleotides, antibodies that bind to an altered polypeptide encoded by a nucleic acid as disclosed herein (e.g. a genomic segment comprising at least one polymorphic marker and/or haplotype of the present invention) or to a non-altered (native) polypeptide encoded by a nucleic acid of the invention as described herein, means for amplification of a nucleic acid associated with the development of adverse effects to administered anesthesia, means for analyzing the nucleic acid sequence of a nucleic acid associated with development of adverse effects to administered anesthesia, means for analyzing the amino acid sequence of a polypeptide encoded by a nucleic acid associated with development of adverse effects to administered anesthesia, and the like. The kits can, for example, include necessary buffers, nucleic acid primers for amplifying nucleic acids of the invention (e.g. a nucleic acid segment comprising one or more of the polymorphic markers as described herein), and reagents for allele-specific detection of the fragments amplified using such primers and necessary enzymes (e.g. DNA polymerase), and the like. Additionally, kits can provide reagents for assays to be used in combination with the methods as disclosed herein, e.g. reagents for use with other diagnostic assays for determining susceptibility to development of adverse effects to administered anesthesia. In some embodiments, reagents for performing WGA are included in the reagent kit.

In some embodiments, a kit for assaying a sample from a subject to detect a risk or susceptibility to developing adverse effects to administered anesthesia, analgesic, and/or opioid in a subject is provided, wherein the kit comprises reagents necessary for selectively detecting at least one allele of at least one polymorphism as disclosed herein in the genome of the individual. In some embodiments, the reagents comprise at least one contiguous oligonucleotide that hybridizes to a fragment of the genome of the individual comprising at least one polymorphism, as disclosed herein. In some embodiments, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with developing adverse effects to administered anesthesia. In some embodiments, reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with developing adverse effects to an administered opioid. In some embodiments, the fragment is at least 20 base pairs in size. Such oligonucleotides or nucleic acids (e.g. oligonucleotide primers) can be designed using portions of the nucleic acid sequence flanking polymorphisms (e.g. SNPs or microsatellites) that are associated with a risk of developing adverse effects to administered anesthesia. In some embodiments, the kit comprises one or more labeled nucleic acids capable of allele-specific detection of one or more specific polymorphic markers or haplotypes, as well as reagents for detection of the label. Suitable labels include, e.g. a radioisotope, a fluorescent label, an enzyme label, an enzyme co-factor label, a magnetic label, a spin label, an epitope label, and the like.

In certain embodiments, the kit further comprises a set of instructions for using the reagents comprising the kit.

Analgesics

Analgesics include paracetamol (also referred to as acetaminophen), the non-steroidal anti-inflammatory drugs (NSAIDs) including, e.g., the salicylates, and opioid drugs such as morphine, fentanyl, hydromorphone, codeine, oxycodone, hydrocodone, tramadol, ondansetron, dexamethasone, methadone, alfentanil, remifentanil, and derivations thereof, and non-opioid analgesics, including acetaminophen, NSAIDs, and combinations and derivations thereof.

Having described the invention in detail, it will be apparent that modifications, variations, and equivalent embodiments are possible without departing from the scope of the invention defined in the appended claims. All examples in the present disclosure are provided as non-limiting examples.

System

Figure 20:
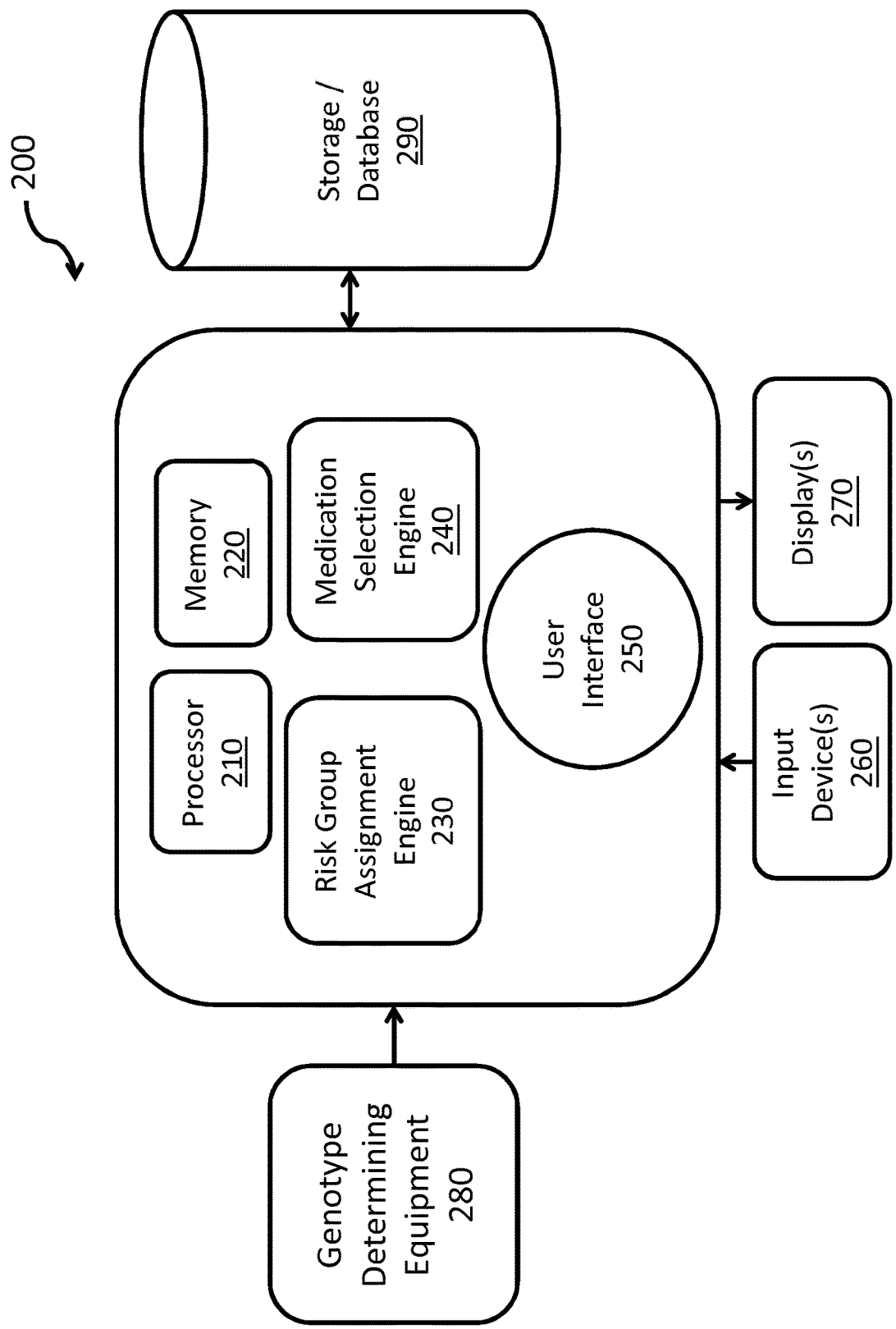
FIG. 20. A schematic of a system described herein

FIG. 20 illustrates an example of a system that can implement one or more features described herein. Here, system 200 includes a processor 210 and a memory 220. System 200 also includes a user interface 250 which permits the system to interact with a user through, for example, one or more input devices 260 and one or more displays 270.

System 200 can also include one or more modules and/or engines that implement one or more features described herein. For example, system 200 can include Risk Group Assignment Engine 230, which can assign a patient into a risk group based upon the patient's genotype for at least one genetic variant. System 200 can also include Medication Selection Engine 240, which can select a medication for the patient based upon the patient's assigned risk group.

In some embodiments, system 200 can be configured to receive a patient's data from a genotype determining equipment 280. In some embodiments, one or more patient data can be stored in a data storage or database 290 which is connected to the system via a data connection.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, modules, model generators, computer instructions, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1

Novel Associations Between FAAH Genetic Variants and Postoperative Central Opioid-Related Adverse Events In this example, the influence of all important genetic variants of fatty acid amide hydrolase (FAAH) from a genome-wide array on perioperative opioid related adverse effects in children was evaluated. This example was later published as Sahasivam et al., *The Pharmacogenomics Journal* (2015) 1-7, the contents of which are hereby incorporated by reference.

Study Design, Participants, and Procedures

This was a prospective, genotype blinded, clinical observational study in a large cohort of children undergoing outpatient adenotonsillectomy with standard perioperative anesthetic, surgical and nursing care. The study is part of a larger ongoing clinical study, entitled Personalizing Perioperative Morphine Analgesia in Children, which is registered with clinicaltrials.gov, NCT01140724. This large prospective clinical trial with standard perioperative care (with the clinical care team blinded to patients' genotypes) evaluated factors contributing to inter-individual variations in analgesic and adverse effect responses to perioperative opioids in children. The study was approved by the institutional review board, and written informed consent was obtained from parents and assent obtained when appropriate from children >7 years of age before enrollment.

Children 6-15 years old undergoing elective outpatient tonsillectomy or adenotonsillectomy were recruited for the study on the day of surgery. Sample inclusion criteria were children designated to have an American Society of Anesthesiologists (ASA) physical status 1 or 2 scheduled for tonsillectomy or adenotonsillectomy because of recurrent tonsillitis, adenotonsillar hypertrophy, or obstructive sleep apnea (OSA). Children with sleep disordered breathing with history of snoring plus sleep pauses lasting more than 10 seconds or daytime drowsiness were considered as clinical symptoms of OSA, as documented in preoperative surgical note, the indication for tonsillectomy in these children was clinical diagnosis of OSA. In addition, the Pediatric Sleep Questionnaire (PSQ) (Chervin R. et al., *Sleep Med,* 1:21-32 (2000); Chervin R. et al., *Arch. Otolaryngol. Head Neck Surg.,* 133:216-22 (2007)), a validated tool was used to assess children for sleep disorders. If the parent of study child reports "yes" to 8 or more of the 22 questions in the PSQ, the child was considered to have OSA.

Children were excluded if they or their parents were non-English speaking. Children allergic to study medications or who had developmental delay, liver or renal diseases, or preoperative pain requiring analgesics (e.g. chronic tonsillitis) were excluded. Due to limited availability of research coordinators for this study, this study was not able to recruit all eligible subjects which resulted in convenient sampling.

All participants received uniform perioperative care, including standardized surgical and anesthetic techniques. Anesthesia was induced using sevoflurane followed by a propofol (2 mg/kg) bolus to facilitate endrotracheal intubation. Anesthesia was maintained with sevoflurane without the use of neuromuscular blockade. Patients received morphine prior to surgical incision. Children with OSA history received 0.1 mg/kg morphine while those without OSA diagnosis received 0.2 mg/kg. If there were any signs suggestive of pain (clinically significant increase in heart rate and blood pressure) following surgical incision and cauterization, the clinical anesthesia team provided additional morphine at 0.05 mg/kg increments intraoperatively as necessary. All children received prophylactic ondansetron (0.1 mg/kg) and dexamethasone (0.1 mg/kg) intraoperatively. Significant postoperative pain measured with facial expression; leg movement; activity; cry; and consolability (FLACC) pain score (Merkel S. et al., *Pediatr. Nurs.,* 23:293-7 (1997)) ≥4/10 was managed in the postoperative anesthesia care unit (PACU) with rescue doses of morphine (0.05 mg/kg increments).

Clinical Outcome Measures

Metrics for analgesic effectiveness and opioid-related adverse effects were recorded for each participant. This study focused on two opioid-related adverse effect outcomes: clinical respiratory depression (RD) and refractory PONV. Total morphine requirement (mg/kg of body weight) was also examined as a measure of analgesic effectiveness. In this study, RD was defined as a persistent (>1 minute) respiratory rate of <10 breaths per minute or oxygen desaturation <92% requiring supplemental oxygen to maintain SpO2 >92% in the absence of clinically obvious upper airway obstruction. PONV was defined as an actual episode of emesis and/or episode of self-reported persistent nausea needing an antiemetic intervention.

Genetic Analysis

Blood was drawn for DNA in the operating room upon intravenous line placement under anesthesia for genotyping of FAAH SNPs. DNA was isolated on the same day and frozen at −20° C. Six previously studied common SNPs were selected to be genotyped using TaqMan allelic discrimination system assays (Life Technologies, Applied Biosystems, Forest City, Calif.). These included rs932816, rs4141964, rs3766246, rs324420, rs324419, and rs2295632. In addition, a genome-wide genotyping was performed using the Illumina Human Omni 5 Genome-Wide Human Array. A total of 3097 SNPs were genotyped, which were used to estimate the genomic inflation factor (λ) from the median $\chi 2$ statistic in PLINK. Out of 3097 SNPs, 66 are in the FAAH gene, including rs3766246 and rs324420. The array also genotyped 244 ancestry informative markers (AIMs), which were used to validate self-reported races and correct population stratification and validation by genetic ancestry markers.

To assess whether self-reported white and black races match well to genetic ancestry, 1397 HapMap subjects were used as reference populations. Out of the 244 AIMs genotyped, 218 were found in the HapMap data. Therefore, principal component analysis was performed with 218 AIMs using SVS 7.7.6 (Golden Helix, Bozeman, Mont.). Up to 10 PCs were also used in statistical modeling to test potential confounding by population stratification.

Statistical Analysis

Statistical analyses were performed using Statistical Analysis Software (SAS), version 9.3, JMP Genomics, version 6.0 (SAS Institute Inc., Cary, N.C.), and R.

Prior to analyses, quality of the data was checked. Characteristics of the patients and properties of the SNPs were examined in African American and Caucasian children respectively. Hardy Weinberg equilibrium (HWE) (Stern C., *Science,* 97:137-8 (1943)) was tested. To analyze the binary outcomes RD and PONV, logistic regressions were performed. To analyze total morphine requirement, linear regression was used. Prior to evaluation of FAAH variants, the effects of covariables were tested. For total morphine dose, age, sex, BMI z scores and OSA were evaluated. For adverse effect outcomes RD and PONV, total morphine was considered as an additional covariable. To select the best fitting model, log likelihood, Akaike and Bayesian Information criterion were compared, and residuals were examined. Covariables which significantly improved model fitting (p<0.05) were retained for subsequent genetic analyses. To assess the single SNP association with the outcomes, additive models were used, in which the genotypes were recoded and tested as continuous variables. Genotypes were recoded to 0, 1, and 2 according to the number of minor alleles of the entire cohort. Statistical modeling was conducted with white and black patients separately.

Results

Demographics.

Participants were primarily white with slightly more females than males. Compared to white children, black children were slightly heavier and had higher OSA frequencies. Self-reported race correlated well with genetic ancestry of origin in 269 African-American and Caucasian children studied.

FAAH SNP Properties.

A total of 70 SNPs in the FAAH gene were genotyped by TaqMan or Omni 5 techniques. SNPs rs3766246 and rs324420 were genotyped by both methods; identical genotypes were observed, suggesting the reliability of the genotype data. Among the 70 SNPs, 39 had minor allele frequency (MAF) >=0.05 in both white and black patients. Tests on Hardy Weinberg equilibrium (HWE) showed that these 39 SNPs were all in HWE at alpha=0.001 level (Bonferroni correction of 39 tests). Therefore, 39 SNPs were included in genetic association analyses.

Self-Reported Race and Genetic Ancestry.

Self-reported white and black races were compared with genetic ancestries estimated from 218 AIMs. In 250 out of the total of 259 patients (>95%), self-reported races clustered well with CEU and African ancestry. Principal component (PC) 1 and 2 successfully separated white and black races. In this study, the analyses were stratified by self-reported races, as it is readily available to clinicians compared to AIMs.

Genetic Associations with Clinical Outcomes.

Single SNP associations were tested with PONV, RD, and total morphine dose in whites and blacks respectively. Black patients required higher total morphine dose (p<0.05, t test) and tended to have lower incidence of PONV (p=0.159, Fisher's exact test), but the incidences of RD were comparable between blacks and whites (p=0.376, Fisher's exact test).

The results of single SNP association tests are summarized in Table 1 and FIG. 1. In white patients, significant association was detected between PONV and three SNPs (rs324420, rs2295632 and kgp12517369), and between total morphine dose and rs647325. In addition, several nominal associations were observed. However, in black patients, only nominal associations were detected for any of the outcomes (Table 1).

TABLE 1

Single SNP associations.

| outcome | SNP | Location | minor allele (%) | P HWE | white P association | OR 95% CI) Beta ± SE | minor allele (%) | P HWE | black P association | OR 95% CI) Beta ± SE | Putative function |
|---|---|---|---|---|---|---|---|---|---|---|---|
|  | rs4141964 | 46865040 | A (0.39) | 0.127 | 0.0014 | 2.41 (1.41, 4.16) |  |  |  |  | intron |
|  | rs3766246 | 46865671 | T (0.39) | 0.127 | 0.0014 | 2.41 (1.41, 4.16) |  |  |  |  | intron |
|  | rs324420 | 46870761 | A (0.23) | 0.008 | 0.0003 | 2.73 (1.58, 4.73) |  |  |  |  | missense |
|  | rs2295633 | 46874383 | A (0.38) | 0.103 | 0.0028 | 2.26 (1.32, 3.85) |  |  |  |  | intron |
| PONV | rs11576941 | 46875067 | A (0.31) | 0.867 | 0.0311 | 0.49 (0.26, 0.94) |  |  |  |  | intron |
|  | rs2295632 | 46879562 | A (0.29) | 0.029 | 0.0005 | 2.61 (1.52, 4.47) |  |  |  |  | downstream |
|  | kgp12517369 | 46882118 | A (0.29) | 0.029 | 0.0005 | 2.61 (1.52, 4.47) |  |  |  |  |  |
|  | rs6687300 | 2.01E+08 | C (0.28) | 0.614 | 0.0339 | 1.86 (1.05, 3.29) |  |  |  |  | intron |
|  | rs1416467 | 80758728 |  |  |  |  | G (0.41) | 0.835 | 0.0309 | 0.07 (0.01, 0.78) | unknown |
|  | rs4141964 | 46865040 | A (0.39) | 0.127 | 0.0402 | 1.57 (1.02, 2.41) |  |  |  |  | intron |
|  | rs3766246 | 4686571 | T (0.39) | 0.127 | 0.0402 | 1.57 (1.02, 2.41) |  |  |  |  | intron |

TABLE 1-continued

Single SNP associations.

| outcome | SNP | Location | minor allele (%) | P HWE | white P association | OR 95% CI) Beta ± SE | minor allele (%) | P HWE | black P association | OR 95% CI) Beta ± SE | Putative function |
|---|---|---|---|---|---|---|---|---|---|---|---|
| | rs324420 | 46870761 | A (0.23) | 0.008 | 0.0473 | 1.61 (1.01, 2.59) | | | | | missense |
| | rs2295632 | 46879562 | A (0.29) | 0.029 | 0.0343 | 1.62 (1.04, 2.54) | | | | | downstream |
| RD | kgp12517369 | 46882118 | A (0.29) | 0.029 | 0.0343 | 1.62 (1.04, 2.54) | | | | | |
| | rs3118378 | 68849687 | G (0.33) | 0.26 | 0.0243 | 1.73 (1.07, 2.79) | G (0.40) | 0.646 | 0.0455 | 0.34 (0.12, 0.98) | unknown |
| | rs4336881 | 1.07E+-8 | A (0.10) | 0.514 | 0.014 | 2.35 (1.19, 4.63) | | | | | unknown |
| | rs4642918 | 2.48E+08 | | | | | C (0.42) | 0.809 | 0.0489 | 0.34 (0.11, 1.00) | unknown |
| Total morphine | rs647325 | 18170886 | G (0.24) | 0.356 | 0.0004 | 0.03 ± 0.01 | | | | | unknown |
| | rs3844253 | 2.42E+08 | A (0.07) | 0.072 | 0.0053 | 0.04 ± 0.01 | | | | | unknown |
| | rs6687300 | 2.01E+-8 | | | | | A (0.30) | 0.96 | 0.0315 | 0.05 ± 0.02 | Intron |
| | rs316873 | 2.42E+08 | | | | | A (0.14) | 0.288 | 0.0092 | −0.08 ± 0.03 | Intron |

On the basis of single SNP association tests, an interesting region was identified ranging from 46865040 bp to 46882118 bp (FIG. 1). Out of 11 SNPs harbored in this region, 7 were associated with PONV and 5 associated with RD in whites. Linkage analysis revealed high D' and R2 and suggested that the 11 SNPs belong to one haplotype block.

Genomic Inflation.

To evaluate the effect of admixture on the significant genetic association with PONV in white children, the genomic inflation factor ($\lambda$) was assessed using 3097 SNPs genomewide. This analysis found that $\lambda$ is 1, suggesting no strong confounding by population stratification exists. When adjusted with up to 10 PCs, the genetic association with PONV in whites remained significant.

Reliability of FAAH Genetic Association with PONV

Because of biological and significant statistical significant associations between FAAH SNP, rs324420 and PONV, to validate associations, we reanalyzed associations with additional 66 white children who had tonsillectomy with similar protocol. The bigger cohort (original cohort of 216 white children plus 66 additional white children) reproduced following consistent and significant associations. The FAAH SNP, rs324420, was significantly associated with PONV (P=0.0053) with addition of one copy of minor allele (A) increasing OR by 2.0-fold; and it was also associated with PONV leading to prolonged PACU stay (P=0.0209) with addition of one copy of minor allele (A) increasing OR by 2.2-fold. Though not statistically significant, the rs324420 AA genotype children overall stayed in PACU longer (97.9 (84.3-113.6) min) than the CC and CA genotype children (83.9 (79.9-88.2 min, P=0.072)), which is clinically and economically relevant following a common outpatient surgery.

Our study showed significant associations between FAAH polymorphisms and refractory PONV following a common outpatient surgery, tonsillectomy. In addition, nominal associations with opioid-induced RD, and prolonged recovery room stays due to PONV with specific FAAH SNPs were identified in a group of white children. Specifically, in white children, addition of one copy of the minor allele of rs4141964, rs3766246, rs324420, rs2295632 and kgp12517369 increased the odds of PONV by 2.42-, 2.42-, 2.73-, 2.61- and 2.61-fold, respectively (P<0.0018, Table 1). These five FAAH SNPs including a missense polymorphism, rs324420, had nominal associations with opioid-related RD and prolonged stays in PACU due to refractory PONV, highlighting possible biological synergistic interactions between opioid and endocannabinoid pathway.

Unknown genetic risk factors (e.g. codeine in ultrarapid metabolizers) even in otherwise healthy patients can increase the risk of respiratory depression, anoxia and death (Kelly L. et al., Pediatrics, 129:e1343-7 (2012); Sadhasivam S. and Myer C., Pain Med., 13:982-3, author reply 4 (2012)). Proactive risk identification, stratification, and preventive measures are important in minimizing the negative impact of opioid related respiratory depression and other adverse effects, such as PONV. PONV remains a big post-anesthesia problem despite prophylactic anti-emetics and is often associated with opioids.

In summary, novel associations were found in children undergoing tonsillectomy between FAAH polymorphisms and postoperative opioid related respiratory depression, PONV, and prolonged stay in PACU. These associations were validated in a different population of older adolescents undergoing major spine fusions. These results demonstrate that specific genetic variants of FAAH are associated consistently with opioid-induced respiratory depression, PONV, and prolonged stay in PACU following surgery in children, which could be extrapolated to adults with similar ethnic and medical backgrounds. When managing children's pain, clinicians need to anticipate potentially higher incidences of opioid-induced respiratory depression and PONV in children with certain FAAH genetic variants.

Example 2

ABCC3 and OCT1 Genotypes Influence Pharmacokinetics of Morphine

We hypothesized that common functionally defective genetic polymorphisms of genes coding for key transporters and enzymes (including OCT1, ABCC3, ABCB1, ABCC2, and UGT2B7) can substantially alter the PK of morphine and its metabolites. The aim of this prospective clinical study was to evaluate the potential impact of selected genetic variants of key transporters and enzymes on intra-venous morphine PK in an extended homogenous cohort of children undergoing tonsillectomy. This example was later published as Venkatasubramanian et al., *Pharmacogenomics* (2014) 15(10): 1297-1309, the contents of which are hereby incorporated by reference.

Study Design, Participants, and Procedures

This study is a part of a larger ongoing observational clinical study titled "Personalizing Perioperative Morphine Analgesia in Children" registered with clinicaltrials.gov (NCT01140724). The current pharmacokinetic-pharmacogenetic study includes an extended cohort of subjects in addition to those previously reported (Fukuda, T. et al., *Pharmacogenomics*, 14:1141-51 (2013), which is incorporated by reference herein in its entirety). The study was designed as a prospective, genotype-blinded study with standard perioperative care in a large cohort of children undergoing outpatient adenotonsillectomy to evaluate factors contributing to inter-individual variations in analgesic and adverse effect responses to perioperative opioids. The study was approved by the institutional review board at Cincinnati Children's Hospital Medical Center, and written informed consent was obtained before enrollment from parents and assent obtained when appropriate from children older than 7 years.

Adolescents and children aged 6-15 years, with an American Society of Anesthesiologists physical status 1 or 2 scheduled for tonsillectomy or adenotonsillectomy because of recurrent tonsillitis, adenotonsil hypertrophy, or OSA were enrolled in this study. Children having morphine allergy, developmental delays after birth, hepatic/renal diseases, chronic analgesic requirement due to preoperative pain and children or parents unable to speak English were excluded from the study (Fukuda, T. et al., *Pharmacogenomics*, 14:1141-51 (2013); Sadhasivam, S., et al., *Pediatrics*, 129:832-8 (2012); Sadhasivam, S., et al., *J. Opioid Manag.*, 8:217-26 (2012)). Children enrolled in the study received standard perioperative care along with intraoperative anesthetic morphine dose of 0.2 mg/kg except children with OSA, who received a dose of 0.1 mg/kg.

Pharmacokinetic Sampling and Analysis

Serial blood samples were obtained from an individual child to quantify morphine, and its active metabolites, M3G and M6G systemic concentration. A pre-dose sample was obtained before IV morphine bolus dose from an IV line. Further samples were obtained using independent venous needle sticks 0-5 min, 10-15 min and 30-45 min after the first bolus morphine intravenous dose. For ethical reasons, blood samples obtained (1-3 no.) post morphine dose were collected before the child fully recovered from anesthesia in the recovery room. Morphine M3G and M6G were quantified in EDTA plasma using an established and validated, semiautomated liquid chromatography-mass spectrometry/mass spectrometry assay. Details of the analytical methods have been described elsewhere (Clavijo, C. et al., *Anal. Bioanal. Chem.*, 400:715-28 (2011)). The reliable limits of quantification were 0.25-1000 ng/ml (r2>0.99) for morphine, and 1-1000 ng/ml (r2>0.99) for both M3G and M6G. Total imprecision was less than 15%. The inter-day accuracy was within 85-115%. There was no carry over, matrix interferences or ion suppression/enhancement interfering with the quantification of the analytes.

Genotyping and Genetic Sampling

Blood samples were collected in the operating room using intra-venous line placed for anesthesia for genotyping relevant polymorphisms. DNA was isolated on the same day, frozen at −20° C. and tested for specific SNPs within the preselected list of functionally important genes (OCT1, ABCC3, ABCB1, and UGT2B7), determined using commercially available TaqMan SNP genotyping assays. Human Omni 5 Genome-Wide Human Array was used to identify additional important SNPs in above selected genes. The participants were genotyped for four non-synonymous SNPs in the OCT1 gene, which cause reduction or loss of OCT1 transporter activity, including Arg61Cys (rs12208357), Gly401Ser (rs34130495), Gly465Arg (rs34059508), and the deletion of Met420 (rs72552763). In addition, rs4793665 (−211C>T), a SNP in the promoter region of ABCC3 that is known to alters mRNA expression affecting the binding of nuclear factors, was genotyped. Also included were the ABCB1 3435T allele, as it has been linked to higher morphine analgesia in cancer-related pain and lower morphine dose requirements in mixed chronic pain population, and UGT2B7 −161 C>T, as genotype CC subjects were associated with increased clearance of lamotrigine.

Morphine PK Model Development and Evaluation

A nonlinear, mixed effect, population pharmacokinetic model was developed for morphine data using NONMEM (version 7.2, ICON Dev. Soln., Md., USA) with PsN-Toolkit (version 3.5.3) as the interface. Data preprocessing, post processing and visualization were performed using the statistical package R (version 2.15). A two-compartment structure was used to describe the morphine concentration-time profile. A delay compartment was incorporated in the model a delay in the transport of morphine to a hypothetical compartment and metabolites formation was modeled to be dependent on morphine concentration in the hypothetical compartment.

The effect of using body weight as a covariate was tested first and included in the pharmacokinetic model with an allometric model. The estimate of individual parameters was modeled to be dependent on the mean population parameter and the underlying inter-individual variability with a log-normal distribution. See Venkatasubramanian et al. *Pharmacogenomics* 2014 15(10):1297-1309 for detail.

The quality of the model was evaluated using a range of criteria including objective function value (OFV), residual diagnostics, and model stability considerations using bootstrap validation techniques. Initial comparison between different models was based on a drop of OFV of 3.84 (p<0.05, DOF=1) between nested models was considered statistically significant. In addition to OFV improvement, models were evaluated using diagnostic goodness-of-fit plots examined to identify possible trends suggestive of model misspecification, η-distribution histograms examined to ensure unimodality. The final model stability was evaluated by refitting the model to 1000 randomly sampled bootstrap datasets.

Pharmacogenomic Analysis

Covariate analysis was also performed to test the significance of the selected genotype as a categorical covariate for individual post-hoc Bayesian estimates of weight-normalized (a) morphine clearance; and (b) M3G/(c) M6G formation clearances. Preliminary pharmacogenetic-pharmacokinetic analysis was carried using Fisher's one-way analysis of variance with p<0.05 considered statistically significant. The significant covariates were then tested out formally in NONMEM by incorporating the genotype as a categorical covariate for morphine clearance and metabolite formation clearances. The significance of a genotype as a covariate in morphine PK was determined by a range of criteria which include (a) a drop of OFV of 3.84 (p<0.05, degree of freedom=1) between nested models, and (b) precision of the additive covariate parameter estimates.

Results

Details of the demographics of the enrolled subjects, the time and concentration profiles for morphine, M3G and M6G collected post morphine dose from the 223 subjects enrolled in the study, and the NONMEM model parameter estimates for the allometrically (body weight)-scaled morphine and metabolite population PK model are described in Venkatasubramanian et al. *Pharmacogenomics* 2014 15(10): 1297-1309. Briefly, of the 220 enrolled subjects, 179 were Caucasian, 38 were African American, while the remaining 6 subjects included 1 child of Asian descent, 1 child of Asian Indian decent and 4 biracial children with one Caucasian and one African American parent. No significant differences were observed in age, weight, or height between Caucasian and African American cohorts.

The distributions of the SNP genotypes are given in the tables below. Subjects were divided into three groups based on OCT1 genotype, as described earlier (Fukuda, T. et al., *Pharmacogenomics*, 14:1141-51 (2013); Fukuda, T. et al., *Clinical Pharmacology & Therapeutics*, 93:S49-S49 (2013); Tzvetkov, M. et al., *Biochemical Pharmacology*, 86:666-678 (2013)). Based on the genotyping results, 58% of children were OCT1 wildtype, 36% were OCT1 heterozygous, and 5.4% were OCT1 homozygous. Of the 12 children with a homozygous genotype, 11 were Caucasian, 1 was Hispanic, and none were of African American descent. Racial heterogeneity was also observed in the ABCB1 C3435T genotype but no racial difference was observed in the polymorphism at the −211C>T position of ABCC3.

TABLE 2

List of OCT1 genotypes and their frequencies across different races observed in the study.

| | rs72552763 | rs12208357 | rs34130495 | rs34059508 | | | | | | | | | |
|---|---|---|---|---|---|---|---|---|---|---|---|---|---|
| | Nucleotide | | | | | | | | | | | | |
| | 1365GAT > del | 286C > T | 1306G > A | 1498G > C | | | | | | | | | |
| | Amino Acid Change | | | | | All Races | | | Caucasians | | | African American | | |
| | deletion of Met420 | Arg61Cys | Gly401Ser | Gly465Arg | N | $N_{tot}$ | Frac | N | $N_{tot}$ | Frac | N | $N_{tot}$ | Frac |
| Wild-Type | GAT | C | G | G | 130 | 130 | 0.58 | 97 | 97 | 0.54 | 31 | 31 | 0.82 |
| Heterozygous | GAT/del | C | G | G | 43 | 81 | 0.36 | 37 | 71 | 0.4 | 4 | 7 | 0.18 |
| | GAT/del | C | G | G/C | 8 | | | 6 | | | 1 | | |
| | GAT | C | G/A | G | 7 | | | 7 | | | 0 | | |
| | GAT | C/T | G | G | 22 | | | 20 | | | 2 | | |
| | GAT | C/T | G/A | G | 1 | | | 1 | | | 0 | | |
| Homozygous | del | C | G | G/C | 1 | 12 | 0.05 | 1 | 11 | 0.06 | 0 | 0 | 0 |
| | del | C | G | G | 2 | | | 2 | | | 0 | | |
| | GAT/del | C | G/A | G | 2 | | | 2 | | | 0 | | |
| | GAT | C | A | G | 1 | | | 1 | | | 0 | | |
| | GAT/del | C/T | G | G | 6 | | | 5 | | | 0 | | |
| | | | | Total | 223 | | | 179 | | | 38 | | |

TABLE 3

Observed frequencies of (A) ABCC3 −211C > T (rs4793665) and (B) ABCB1 C3435T (rs1045642) across different races in the current study.

A. ABCC3 −211C > T (rs4793665)

| | 32rs# rs4793665 Nucleotide −211C > T Amino Acid Change | All Races | | Caucasians | | African-American | |
|---|---|---|---|---|---|---|---|
| | N/A | N | Fraction | N | Fraction | N | Fraction |
| Wild-Type | T | 73 | 0.327 | 61 | 0.341 | 11 | 0.289 |
| Heterozygous | C/T | 112 | 0.502 | 90 | 0.503 | 19 | 0.5 |
| Homozygous | C | 38 | 0.17 | 28 | 0.156 | 8 | 0.211 |
| | | 223 | | 179 | | 38 | |

B. ABCB1 C3435T (rs1045642)

| | rs# rs1045642 Nucleotide C3435T Amino Acid Change | All Races | | Caucasians | | African-American | |
|---|---|---|---|---|---|---|---|
| | Silent | N | Fraction | N | Fraction | N | Fraction |
| Wild-Type | T | 64 | 0.287 | 62 | 0.346 | 2 | 0.053 |
| Heterozygous | C/T | 87 | 0.39 | 72 | 0.402 | 11 | 0.289 |
| Homozygous | C | 72 | 0.323 | 45 | 0.251 | 25 | 0.658 |
| | | 223 | | 179 | | 38 | |

TABLE 4

Results of the pharmacogenetic covariate analysis to study the impact of OCT1, ABCC3, and ABCB1 genotypes on morphine clearance (CLM) and metabolite formation clearance (CLFM3G and CLFM6G) using simple one-way ANOVA and NONMEM covariate analysis. #Mean [Lower 95% CI-Uppper 95% CI]

| Transporter | Analysis Method | Parameter | Morphine | Morphine-3-Glucuronide | Morphine-6-Glucuronide |
|---|---|---|---|---|---|
| 1-Oct | Anova | $\Delta CL^{\#}$ | 0.114 [0.003:0.225] | 0.509 [0.179:0.839] | 0.613 [−0.144:1.37] |
|  | Nonmem | $\Delta CL^{\#}$ | 0.163 [0.046:0.28] | 0.475 [0.3:0.651] | 0.574 [0.476:0.670] |
|  |  | dOFV | −4 | −9.39 | −2.87 |
| ABCC3 | Anova | $\Delta CL^{\#}$ | 0.047 [−0.019:0.114] | 0.301 [0.107:0.501] | 0.283 [0.041:0.526] |
|  | Nonmem | $\Delta CL^{\#}$ | 0.079 [−0.008:0.167] | 0.476 [0.055:0.895] | 0.432 [−0.037:0.90] |
|  |  | dOFV | −1.92 | −9.54 | −5.29 |
| ABCB1 | Anova | $\Delta CL^{\#}$ | −0.018 [−0.074:0.038]] | 0.178 [0.006:0.349] | 0.101 [−0.119:0.321] |
|  | Nonmem | $\Delta CL^{\#}$ | −0.021 [−0.093:0.052] | 0.246 [0.004:0.491] | 0.133 [−0.149:0.416] |
|  |  | dOFV | −0.4 | −4.33 | −0.85 |

The pharmacokinetics of morphine was described using a two compartment model with inter-individual variability on its systemic clearance (CL). The metabolite profiles were captured using a single compartment model with inter-individual variability on the formation clearances. The volume of distribution and clearance for the metabolites were fixed based on prior reports (Bouwmeester, N. et al., *Br. I Anaesth.*, 92:208-17 (2004)), as the profiles only contain information about their formation owing to short sampling duration. The η-shrinkage on morphine clearance and M3G formation clearance was low (16.5% and 20%), while it was high (31.8%) for M6G formation clearance indicating limited information pertaining to M6G formation in this dataset (Savic, R. and Karlsson, M., *AAPS J.*, 11:558-69 (2009)). The formation of metabolite was dependent on the morphine concentrations in a hypothetical compartment, which lagged central compartment, resulting in a delay in metabolite formation. Addition of a delay compartment resulted in the removal of the over-prediction of metabolite levels at earlier times and under predictions at latter times and resulted in a significantly better model (dOFV=−305). Incorporation of allometric scaling to account for the effect of body weight on clearances and volumes with exponents of 0.75 and 1 was found significantly improve model fits (dOFV=−184) (Anderson, B. and Holford, N., *Br. J. Clin. Pharmacol.*, 72:518-20; author reply 521-3 (2011)). Inclusion of race effect on morphine clearance improved the model with African Americans having 8% higher mean clearance than Caucasians (Sadhasivam, S. et al., *J. Opioid Manag.*, 8:217-26 (2012)). Similarly, gender influences morphine pharmacokinetics, with girls having 5% higher clearance than boys.

Preliminary covariate analysis of the contribution of preselected functional genotypes was performed using one way ANOVA on post-hoc Bayesian estimates of weight normalized morphine clearance and formation clearances for both metabolites. These estimates obtained after normalizing the contribution due to body weight represent individual clearance values in the absence of size as a confounding factor. Visual inspection of the individual post hoc Bayesian estimates for morphine clearance (FIG. 2) suggests that homozygous OCT genotype subjects had lower mean CLM than the wild-type and heterozygous group combined in our study cohort. A similar trend was observed for M3G formation clearances, where OCT1 homozygous group had ~50% lower mean values than others. The evidence of a lower M-6G formation clearance in the homozygous group (by ~55%) was substantial though it was not statistically significant (p=0.09). Consistent with the preliminary ANOVA analysis, NONMEM covariate analysis revealed that OCT1 homozygous group was a significant covariate (dOFV>3.84) for CLM and CLFM3G, with homozygotes having 16% and 48% lower clearance than others. M6G concentrations were quantified in only 2 of the 12 homozygous subjects (due to concentration below LOQ and analytical problems), resulting in limited quantitative information about differences in M6G formation across different groups.

Visual inspection of the variation of post-hoc Bayesian estimates for individual clearance with respect to ABCC3 −211C>T genotype (FIG. 2) shows progressively higher metabolite formation clearances and morphine clearances in subjects with increasing number of C alleles. Preliminary one way ANOVA analysis conducted using two alternative groupings i.e. (1) TT+CT vs. CC & (2) TT vs. CT+CC, suggested that the evidence for the former grouping was more statistically significant than the latter across tests for all variables (Mizuno, T. et al., *Clinical Pharmacology & Therapeutics*, 93:S63-S63 (2013)). Evaluation of this ABCC3 genotype as a potential covariate in the NONMEM model revealed that the CC genotype had significantly higher CLFM3G, and its inclusion substantially improved the model fit (dOFV=−9). Similarly, ABCC3 genotype was found to be a significant covariate for CLFM6G based on one-way ANOVA (p=0.03) and covariate inclusion in the NONMEM model (dOFV=−4.86). Based on the NONMEM model estimates, the CC genotype had 46% (95% CI: 4.3%-88%) higher CLFM3G than TT and CT genotypes combined. Estimates for the increase in CLFM6G were similar to CLFM3G, though precision on this parameter was lower. Further evaluation using nonparametric parameter confidence interval estimates based on 1000 bootstrap estimations confirmed that the increase in CLFM6G estimated reasonably well with a median of 47% and 95% CI's of 2%-100%. While the evidence of homozygous CC genotype having higher metabolite formation was strong, its effect on morphine clearance was less pronounced. Inclusion of the ABCC3 genotype as a potential covariate improved the model fit (dOFV=−2), though it did not significantly improve the model with the CC genotypes estimated to have moderately higher (8.1%; 95% CI: −0.7%:16.8%) morphine clearance than others.

Figure 2:
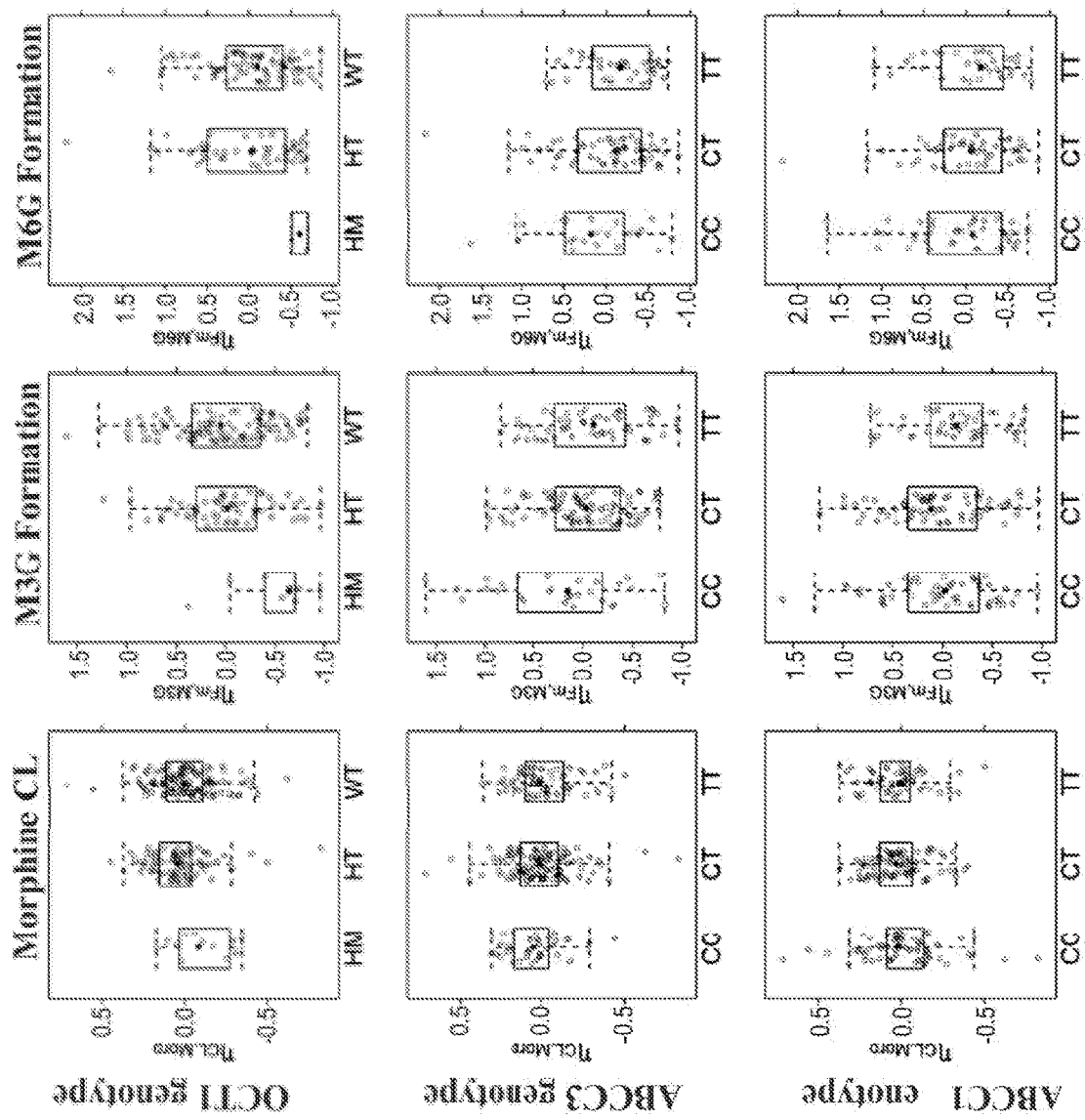
FIG. 2. Variation of morphine clearance and M3G/M-6G formation clearance with OCT1, ABCC3, and ABCB1 genotype observed in the adenotonsillectomy group study.

Variation in post estimates for individual clearances (CLM/CLFM6G) (FIG. 2) shows no discernable influence of ABCB1 C3435T genotype on CLM and CLFM6G. However, subjects with CT and TT genotype combined seemed to have higher CLFM3G than subjects with TT genotype (FIG. 2). These trends were confirmed to be statistically significant based on one-way ANOVA analysis, which revealed that CT+TT genotype had 18.4% higher CLFM3G than TT (p=0.04) while its effect on CLM was minimal (1%). These were consistent with the results from NON- MEM analysis where C3435T genotype was identified as a significant covariate for CLFM3G (dOFV=−4.32) but not for CLM and CLFM6G.

Discussion

Recently, with an increase in opioid prescription, a growing interest has been observed in quantifying the contribution of different pharmacogenetic (PG) factors to variability in opioid response (Branford, R. et al., *Clin. Genet.*, 82:301-10 (2012); Cohen, M. et al., *Curr. Opin. Anaesthesiol.*, 25:419-27 (2012); Sadhasivam, S. and Myer, C., *Pain Med.*, 13:982-3, author reply 984 (2012); Eissing, T. et al., *Mol. Diagn. Ther.*, 16:43-53 (2012)). The focus of this study at present is to capture the role of PG on morphine pharmacokinetics (PK) though part of the contribution of genetic variability to opioid response will be due to pharmacodynamic (PD) factors. We show here the successful development of a NONMEM model to capture the time profiles for morphine and its metabolites. Using a simple one-way ANOVA-based approach with post-hoc individual estimates, pre-selected SNPs were screened for potential impact on CLM, CLFM3G and CLFM6G. NONMEM-based covariate analysis was then used to identify SNPs across 3 different genes (OCT1, ABCC3, and ABCB1) that contribute significantly to morphine PK and/or its metabolites, although no association with either the UGT2B7 or the ABCC2 genotype was found.

The results of this larger cohort study confirmed our earlier results showing that an OCT1 homozygous group had about 17% lower clearance than wild-type and heterozygous combined. (Fukuda, T. et al., *Pharmacogenomics*, 14:1141-51 (2013); Fukuda, T. et al., *Clinical Pharmacology & Therapeutics*, 93:S49-S49 (2013)). Consistent with our results, a separate clinical study demonstrated that subjects with 2 or more functionally defective alleles had significantly lower morphine clearance than others (Tzvetkov, M. et al., *Biochemical Pharmacology*, 86:666-678 (2013)). The results presented here offer further evidence that limited uptake of morphine into hepatocytes with functionally defective OCT1 genotype directly impacted morphine CL. Consistent with the observation of lower CL, this study also demonstrates for the first time that the OCT1 homozygous subjects had lower transformation of both metabolites, M3G and M6G. Limited morphine uptake into hepatocytes in these subjects impacted downstream morphine's metabolic processes resulting in lower morphine glucuronide generation. Correlated observations of lower morphine CL as well as M3G/M6G formation among homozygous subjects provide stronger evidence that OCT1 uptake of morphine into hepatocytes plays a key role in the PK of morphine.

At physiologic pH, morphine is expected to be in an ionized state with the amide group charged (pKa=8.4), making it a suitable substrate of OCT1. In vitro studies have suggested that morphine has low transporter independent permeability and transporter-dependent uptake of morphine into hepatocytes accounting for about 60% of the total uptake. Furthermore, these studies also showed that morphine uptake was concentration dependent in hepatocytes over-expressing wild-type OCT1, though uptake rate was substantially reduced (75-100%) when loss-of-function polymorphisms were present. Based on these results, the impact of the presence of defective alleles was higher in metabolite formation (~45%) than morphine clearance (~16%) and is more consistent with the 37% lower AUC's observed in subjects with 2 or more defective alleles. While morphine being a substrate of OCT1 is well characterized, the role of OCT1 in the uptake of glucuronide metabolites is heretofore not known. These results indicate that the effect of OCT1 on morphine clearance can be much higher than the currently estimated 16%, meaning that the homozygous subjects would experience better analgesia but worse adverse reactions in response to morphine dosing.

In addition, the present study showed that children with the C/C genotype at rs4793665 (ABCC3) had 46% higher M6G formation and 41% higher M3G formation, indicating an increased efflux of M6G into the plasma compared to the C/T and T/T genotypes combined. An earlier study reported that the ratios of M3G to morphine and M6G to morphine were significantly lower in patients with C/T and T/T genotype in a subset of subjects from this study (Mizuno, T. et al., *Clinical Pharmacology & Therapeutics*, 93:S63-S63 (2013)). The current NONMEM based analysis better accounts for variation due to dosing and weight across the study than before (Mizuno, T. et al., *Clinical Pharmacology & Therapeutics*, 93:S63-S63 (2013)), thereby facilitating a more mechanistic interpretation of the results. Though the genotype was observed to clearly alter the metabolite formation, an increased morphine clearance among subjects was also observed. No clear evidence of morphine being a substrate of ABCC3 exists, though the efflux of morphine into the plasma by ABCC3 has been speculated (Tzvetkov, M. et al., *Biochemical Pharmacology*, 86:666-678 (2013)).

The incidence of adverse effects after morphine dosing has been reported to be higher in Caucasian than African-American children and Latino than Non-Latino children (Sadhasivam S. et al., *Pediatrics*, 129:832-8 (2012); Sadhasivam S. et al., *J. Opioid Manag.*, 8:217-26 (2012); Jimenez, N. et al., *J. Health Care Poor Underserved*, 21:229-36 (2010)). We have reported racial differences in morphine requirement observed in the clinic with African-American children requiring more morphine compared to Caucasian children. We found that Caucasians had 8% lower morphine CL than African-Americans, which was further reduced to 7% when OCT1 genotype was included as a covariate along with race. Also, our PK/PG associations were consistently reproduced when tested among majority race (Caucasians: 80%), thereby limiting the influence of population stratification. As we reported earlier, the higher frequencies of the OCT1 homozygous group among Caucasians (about 5%) compared to African-Americans could be one of the reasons behind lower morphine CL in Caucasian children.

In conclusion, this large pediatric pharmacokinetic and pharmacogenetic study demonstrates that in addition to body weight, OCT1 and ABCC3 homozygous genotypes play a significant role in the pharmacokinetics of morphine and its metabolites. Specifically, children with ABCC3 rs4793665 homozygous C/C genotype had about 46% higher M6G formation rate than the wild-type and heterozygous genotypes combined, resulting in increased M6G transport into the plasma; consistently 41% higher M3G formation was also observed in homozygous C/C genotype. OCT1 homozygous genotypes (n=12) were found to have significantly lower morphine clearance (~17%). Higher frequencies of the ABCC3 rs4793665 C/C and OCT1 homozygous genotypes were observed in the Caucasian population. This finding partially explains lower morphine clearance and higher incidences of adverse effects with morphine in Caucasians than African-Americans. A small difference in morphine clearance between girls and boys was also observed.

Example 3

Validation of ABCC3, ABCB1, and FAAH Variants

Further work was conducted to extend and validate the above results for ABCC3. The pharmacokinetic model and analysis were as discussed above. In addition to the tonsillectomy cohort (T&A study) described above, this work also included a different surgical population of adolescents undergoing posterior spine fusion (Spine study). The spine study group included 88 non-obese adolescents with idiopathic scoliosis who underwent posterior spine fusion. All patients received morphine patient controlled analgesia after surgery and were followed for 48 hours. Data regarding morphine consumption, postoperative pain scores, use of diazepam, and other analgesics was recorded. Subjects enrolled were 11 to 19 years old; 59% female, and 85% Caucasian.

The model parameters estimates for the morphine and metabolite population PK model with alometric scaling are shown in the table below.

TABLE 5

Model parameters estimates for the morphine and metabolite population PK model with alometric scaling.

| Parameter | T&A Study Estimate | 95% CI** | Spine Study Estimate | 95% CI†† |
|---|---|---|---|---|
| Population Mean Parameters | | | | |
| CL | 1.25 | [1.08, 1.416] | 1.62 | [1.43, 1.80] |
| $V_1$ | 7.05 | [3.33, 10.77] | 9.823 FIX | — |
| Q | 2.24 | [1.45, 2.63] | 1.33 | [1.01, 1.65] |
| $V_2$ | 30.8 | [21.27, 40.32] | 34.9 | [24.55, 45.29] |
| $FCL_{M3G}$ | 0.89 | [0.52, 1.27] | 1.3 | [1.06, 1.54] |
| $V_{M3G}$# | 23 FIX | — | 23 FIX | — |
| $CL_{M3G}$# | 0.29 FIX | — | 0.29 FIX | — |
| $FCL_{M6G}$ | 0.0751 | [0.04, 0.109] | 0.215 | [0.18, 0.25] |
| $V_{M6G}$# | 30 FIX | — | 30 FIX | — |
| $CL_{M6G}$# | 0.097 FIX | — | 0.097 FIX | — |
| Gamma CLM | 0.72 | [0.56, 0.88] | 0.75 FIX | — |
| Gamma M3G | 1.5 | [1.26, 1.74] | 1.39 | [0.91, 1.868] |
| Gamma M6G | 1.26 | [0.925, 1.595] | 1.39 | [0.99, 1.79] |
| $K_{delay,M3G}$ | 0.043 | [0.015, 0.071] | 0.12 | [0.073, 0.167] |
| $K_{delay,M6G}$ | | | 0.074 | [0.052, 0.095] |
| Inter-individual variability | | | | |
| $\omega^2_{CL,M}$ | 0.053 | [0.03, 0.076] | — | — |
| $\omega^2_{V1,M}$ | — | — | 0.85 | [0.32, 1.4] |
| $\omega^2_{FCL,M3G}$ | 0.22 | [0.15, 0.28] | 0.22 | [0.04, 0.29] |
| $\omega^2_{FCL,M6G}$ | 0.33 | [0.20, 0.46] | 0.09 | [0.042, 0.16] |
| Residual Error | | | | |
| $\varepsilon_M$ | 0.21 | [0.19, 0.23] | 0.52 | [0.43, 0.62] |
| $\varepsilon_{M3G}$ | 0.45 | [0.40, 0.50] | 0.48 | [0.38, 0.58] |
| $\varepsilon_{M6G}$ | 0.50 | [0.43, 0.57] | 0.33 | [0.25, 0.37] |

These parameters were fixed based on prior reports and were not estimated by NONMEM
††The 2.5th and 97.5th percentile of the bootstrap parameter estimates.
**Confidence interval estimated based on standard error estimates
Parameter Notations:-
CL: Clearance;
Q: Inter-compartmental clearance;
V: Volume;
FCL: Formation clearance;
ω2: Between Subject Variance;
ε: Proportional Error coefficient;
Subscripts:-
M: Morphine;
c: Central;
p: Peripheral.

FIG. 3A shows the inter-individual variation in morphine CL and metabolites (M3G/M6G) formation clearances (FCLM3G & FCLM6G) with ABCC3 rs4793665 genotype observed in our studies. Overall, rs4793665 genotypes were found to be a significant covariate for FCLM6G and FCLM3G (dOFV=−8.41 and −7.44 respectively) based on NONMEM covariate analysis with CC genotypes having 38% and 46% higher formation respectively than others. Subjects with CC genotype were also found to have significantly higher M6G formation CL (38% higher; 29% RSE) in the spine study. A similar trend was observed among adenotonsillectomy subjects though it was not significant. Across both studies CC genotypes were significantly associated with higher M3G formation CL with similar estimates from the adenotonsillectomy (46% higher; 46% RSE) and spine (57% higher; 38% RSE) studies.

Figure 3B:
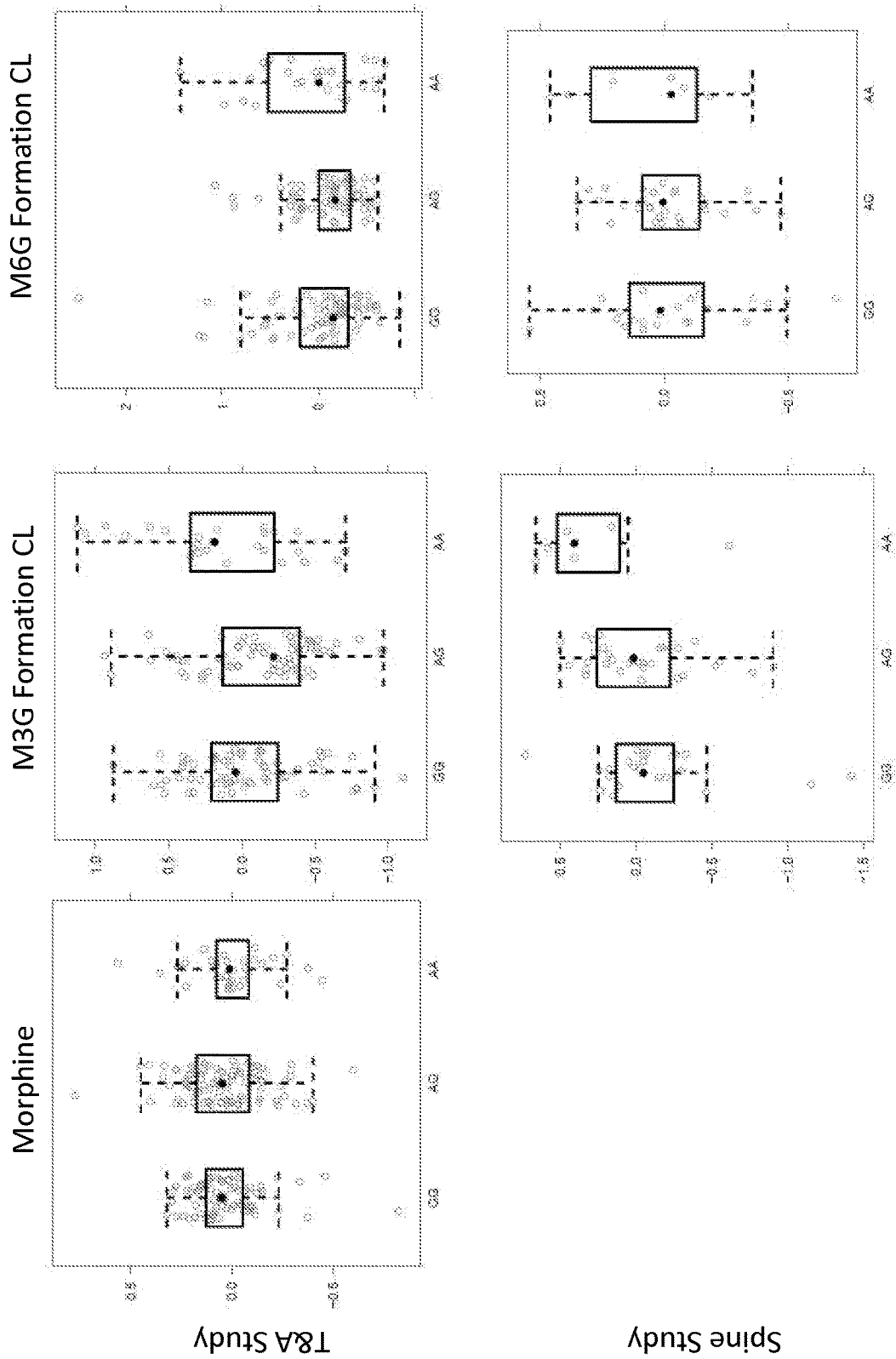
FIG. 3B. Inter-individual variation in morphine CL and metabolites (M3G/M6G) formation clearances (FCLM3G & FCLM6G) with ABCC3 rs4148412 genotype observed in our studies. The top panel summarized results from the study undergoing adenotonsillectomy while bottom panel summarizes results from the spine surgery. ABCC3 rs4148412 genotype is varied across the x-axis. Empirical Bayesian estimates of individual morphine CL (ηMor,CL), M3G formation CL (ηM3G,FCL) and M6G formation CL (ηM6G,FCL) from the Nonmem analysis are plotted on the y-axis for the left, middle and right panels respectively.

FIG. 3B shows the inter-individual variation in morphine CL and metabolites (M3G/M6G) formation clearances (FCLM3G & FCLM6G) with ABCC3 rs4148412 genotype observed in our studies. rs4148412 AA genotypes were found to be a significant covariate for FCLM3G (dOFV=−6.54) based on NONMEM covariate analysis with AA genotypes having 36% (95% CI [−0.002; 0.71]) higher formation. Consistent PK-PG associations were found among the spine subjects with rs4148412 AA genotype showing a strong trend covariate for FCLM3G (dOFV=−3.8) based covariate analysis using NONMEM. Among the spine subjects rs4148412 AA genotypes were estimated to have 48% (95% CI[0.21; 1.06]) higher formation than other genotypes. In summary, subjects with the AA genotype were found to have significantly higher M3G formation CL (36% higher; 51% RSE) in the adenotonsillectomy study. A similar trend tending to significance (p=0.06) was observed in the spine study with AA genotypes having 52% higher (60% RSE) formation. Across both studies AA genotypes showed trends of higher M6G formation.

FIG. 4A shows the inter-individual variation in morphine CL and metabolites (M3G/M6G) formation clearances (FCLM3G & FCLM6G) with ABCC3 rs739923 genotype observed in our studies. rs733392 genotype was a significant covariate for M3G formation among spine subjects with AA subject having 57% lower formation than others. But the rs733392 genotype was not a significant covariate in the larger T&A study. No significant genetic associations were found between ABCC3 rs739923 genotypes and morphine CL and metabolite formation CL's.

Figure 4B:
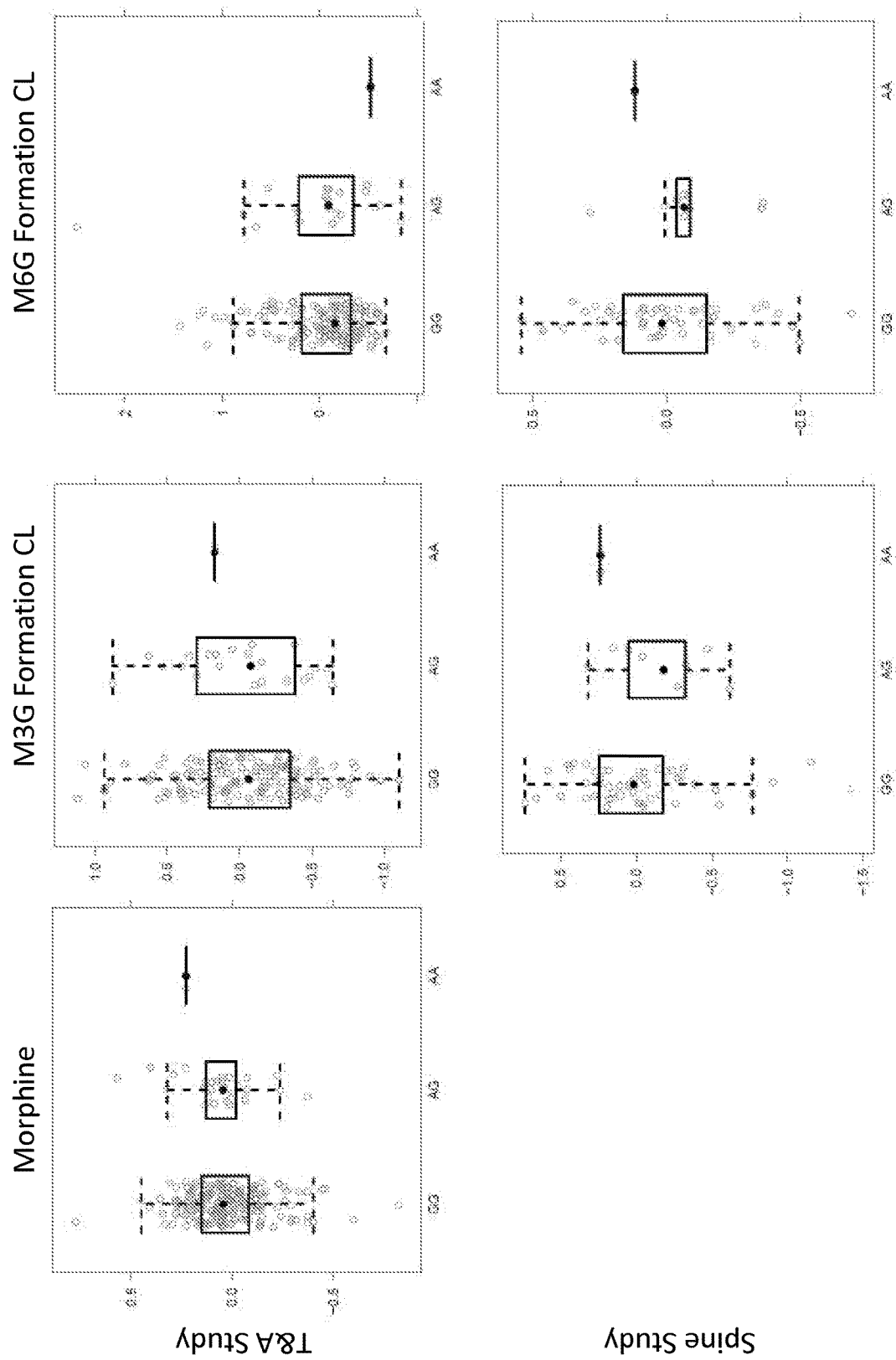
FIG. 4B. Inter-individual variation in morphine CL and metabolites (M3G/M6G) formation clearances (FCLM3G & FCLM6G) with ABCC3 kgp8560677 genotype observed in our studies. The top panel summarized results from the study undergoing adenotonsillectomy while bottom panel summarizes results from the spine surgery. ABCC3 kgp8560677 genotype is varied across the x-axis. Empirical Bayesian estimates of individual morphine CL (ηMor,CL), M3G formation CL (ηM3G,FCL) and M6G formation CL (ηM6G,FCL) from the Nonmem analysis are plotted on the y-axis for the left, middle and right panels respectively.

FIG. 4B shows the inter-individual variation in morphine CL and metabolites (M3G/M6G) formation clearances (FCLM3G & FCLM6G) with ABCC3 kgp8560677 genotype observed in our studies. No significant genetic associations were found between ABCC3 kgp8560677 genotypes and morphine CL and metabolite formation CL's.

These results are summarized in the table below.

TABLE 6

Summary of results from follow-up study with ABCC3 variants

| SNF | Study | Parameter | Morphine | Morphine-3-Glucuronide Formation | Morphine-6-Glucuronide Formation |
|---|---|---|---|---|---|
| rs4793665 | T&A | ΔCL[#] | −0.07 (66%) | 0.463 (46%) | 0.17 (62%) |
| CC vs |  | ΔOFV[1] | −1.86 | −9.54 | −1.33 |
| CT + TT | Spine | ΔCL[#] | — | 0.57 (37.9) | 0.38 |
|  |  | ΔOFV[1] | — | −7.44 | −8.74 |
| rs4148412 | T&A | ΔCL[#] | 0.04 (139%) | −0.36 (51%)* | −0.27 (84%) |
| GG + AG |  | ΔOFV[1] | −0.588 | −6.54 | −2.41 |
| vs. AA | Spine | ΔCL[#] | — | −0.52 (60%) | 0.13 (146%) |
|  |  | ΔOFV[1] | — | −3.74 | −0.62 |
| kgp8560677 | T&A | ΔCL[#] | 0.07 (67%) | 0.05 (202%) | 0.06 (326%) |
| GG + AG |  | ΔOFV[1] | −1.71 | −0.159 | −0.117 |
| vs. AA | Spine | ΔCL[#] | — | 0.136 (144%) | 0.09 (199%) |
|  |  | ΔOFV[1] | — | −0.455 | −0.491 |
| rs739923 | T&A | ΔCL[#] | 0.03 (232%) | 0.16 | −0.26 |
| GG + AG |  | ΔOFV[1] | −0.26 | −2.0 | −1.26 |
| vs. AA | Spine | ΔCL[#] | — | 0.35 | 0.00 |
|  |  | ΔOFV[1] | — | −1.86 | −0.0 |
| rs733392 | T&A | ΔCL[#] | 0.097 (84%) | 0.125 (99%) | −0.417 (82%) |
| GG + AG |  | ΔOFV[1] | −2.1 | −0.86 | −2.38 |
| vs. AA | Spine | ΔCL[#] | — | −0.57 | −0.09 (154%) |
|  |  | ΔOFV[1] | — | −4.49 | −0.09 |

[1]ΔOFV = OFV$_{Cov}$ − OFV$_{NoCov}$
[#]mean (RSE %)
Results highlighted in bold were found to be statistical significant
*p < 0.1

Morphine and metabolite pharmacokinetics from the two studies were well described using the same structural PK model which include a central and peripheral compartment for morphine, one distribution compartment for each metabolite and a compartment to account for the delay in the metabolite formation. Model parameters for the morphine PK model were found to be similar across both studies with the model parameters for the spine subject being higher than the T&A subjects. The difference in the morphine models from the two studies could be attributed to inter-study variances arising due to differences in (a) population, (b) co-medication and (c) pharmacokinetic sampling strategy. The ratio of the formation clearance of M3G relative to M6G morphine clearance estimates were found to be 7.2 in the spine study and 9.6 in the T&A study. This is consistent with other reports that M3G metabolite formation is 7-10 fold M6G formation.

In the earlier study, we showed that children with C/C genotype of rs4793665 (ABCC3) had 46% higher M6G formation and 41% higher M3G formation indicating an increased efflux of metabolites into the plasma than C/T and T/T genotypes combined. In the current analysis we found that ABCC3 rs4148412 AA genotype had higher M3G formation. A mechanistic basis for the impact of genetic variation in rs4148412 on ABCC3 function is not well understood. ABCC3 was found to be expressed in primarily in the basolateral surface of the hepatocytes and has been reported to have high affinities for morphine glucuronides. Though the genotype was observed to clearly alter the metabolite formation, no significant impact morphine clearance was observed.

Figure 6:
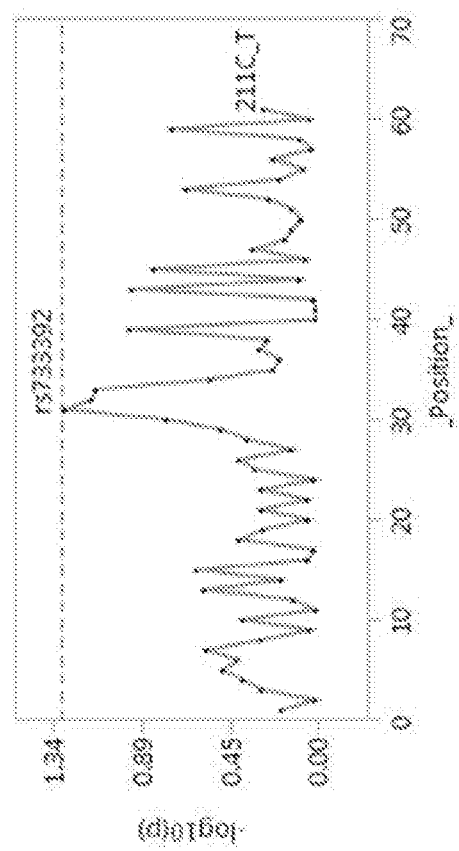
FIG. 6. Validation of Association between ABCC3 rs733392 and Respiratory Depression in Adolescents undergoing Posterior Spine Fusion Surgery. ABCC3 SNP rs733392 was associated with respiratory depression in spine surgery population, consistent with associations found in tonsillectomy population. ABCC3 rs733392 and rs733923 are in linkage disequilibrium; both were associated with respiratory depression in tonsillectomy population.

To further determine the significance of the ABCC3 SNPs, we validated them against clinical outcomes. FIG. 6 shows validation of the association between ABCC3 rs733392 and respiratory depression in adolescents undergoing posterior spine fusion surgery.

The table below shows the validation of the indicated variants of ABCC3 with clinical outcomes. Plink analysis on GWAS ABCC3 data, including a total of 65 SNPs between chr17:48710 kb and chr17:48770 kb passed quality control. Caucasian and African-American populations were combined and adjusted in the model as well as other significant covariates. For these analyses the odds ratio was calculated as homozygous mutant vs. het/het vs. wild-type; PONV=Postoperative nausea and vomiting; and plongRD=Respiratory depression leading to prolonged PACU stay.

TABLE 7

Association of ABCC3 Variants with Clinical Outcomes

| Gene | Clinical outcome | associated SNP | p-value | Odds ratio | Genomic position | No. of subjects |
|---|---|---|---|---|---|---|
| ABCC3 | PONV | kgp8560677 | 0.005114 | one copy of A increase odds by 3.117 | 48755388 | 316 |
| ABCC3 | plongrd | rs739923 | 0.008311 | one copy of A decrease odds by 0.3069 | 48735774 | 316 |
| ABCC3 | plongrd | rs4148412 | 0.008421 | one copy of A increase odds by 2.232 | 48733815 | 313 |

TABLE 7-continued

Association of ABCC3 Variants with Clinical Outcomes

| Gene | Clinical outcome | associated SNP | p-value | Odds ratio | Genomic position | No. of subjects |
|---|---|---|---|---|---|---|
| ABCC3 | total morphine | rs11568607 | 0.023 | one copy of allele A increase total morphine by 0.050 mg/kg | 48745787 | 315 |
| ABCC3 | total morphine | kgp8560677 | 0.047 | one copy of allele A increase total morphine by 0.026 mg/kg | 48755388 | 315 |
| ABCC3 | combineRD | kgp12040773 | 0.04 | one copy of allele C increase odds by 1.665 fold | 48713568 | 313 |
| ABCC3 | combineRD | kgp3814620 | 0.046 | one copy of allele G decrease odds by 0.6417 fold | 48739543 | 313 |
| ABCC3 | PONV | rs872793 | 0.01494 | one copy of G increase odds by 2.606 | 48761880 | 316 |
| ABCC3 | PONV | rs17563146 | 0.019 | one copy of A decrease odds by 0.3234 | 48769329 | 314 |
| ABCC3 | PONV | rs4148416 | 0.02303 | one copy of A increase odds by 2.37 | 48753423 | 316 |
| ABCC3 | PONV | kgp5563788 | 0.03162 | one copy of A increase odds by 0.3578 | 48757911 | 316 |
| ABCC3 | opiintervneed | kgp9196732 | 0.02161 | one copy of A decrease odds by 0.1622 | 48720999 | 316 |
| ABCC3 | plongrd | kgp12280761 | 0.01574 | one copy of A decrease odds by 0.4603 | 48744612 | 315 |
| ABCC3 | plongrd | rs1978153 | 0.01804 | one copy of G decrease odds by 0.449 | 48737861 | 316 |
| ABCC3 | plongrd | rs3785911 | 0.02523 | one copy of C increase odds by 1.939 | 48767431 | 316 |
| ABCC3 | plongrd | kgp3814620 | 0.02815 | one copy of G decrease odds by 0.4396 | 48739543 | 316 |
| ABCC3 | plongrd | rs733392 | 0.0301 | one copy of A decrease odds by 0.4018 | 48736403 | 313 |
| ABCC3 | plongrd | kgp5563788 | 0.04473 | one copy of A decrease odds by 0.2255 | 48757911 | 316 |
| ABCC3 | plongrd | kgp2507665 | 0.04768 | one copy of C decrease odds by 0.4705 | 48740116 | 316 |
| ABCC3 | plongrd | kgp1777110 | 0.04906 | one copy of A decrease odds by 0.4836 | 48748185 | 316 |

Figure 9:
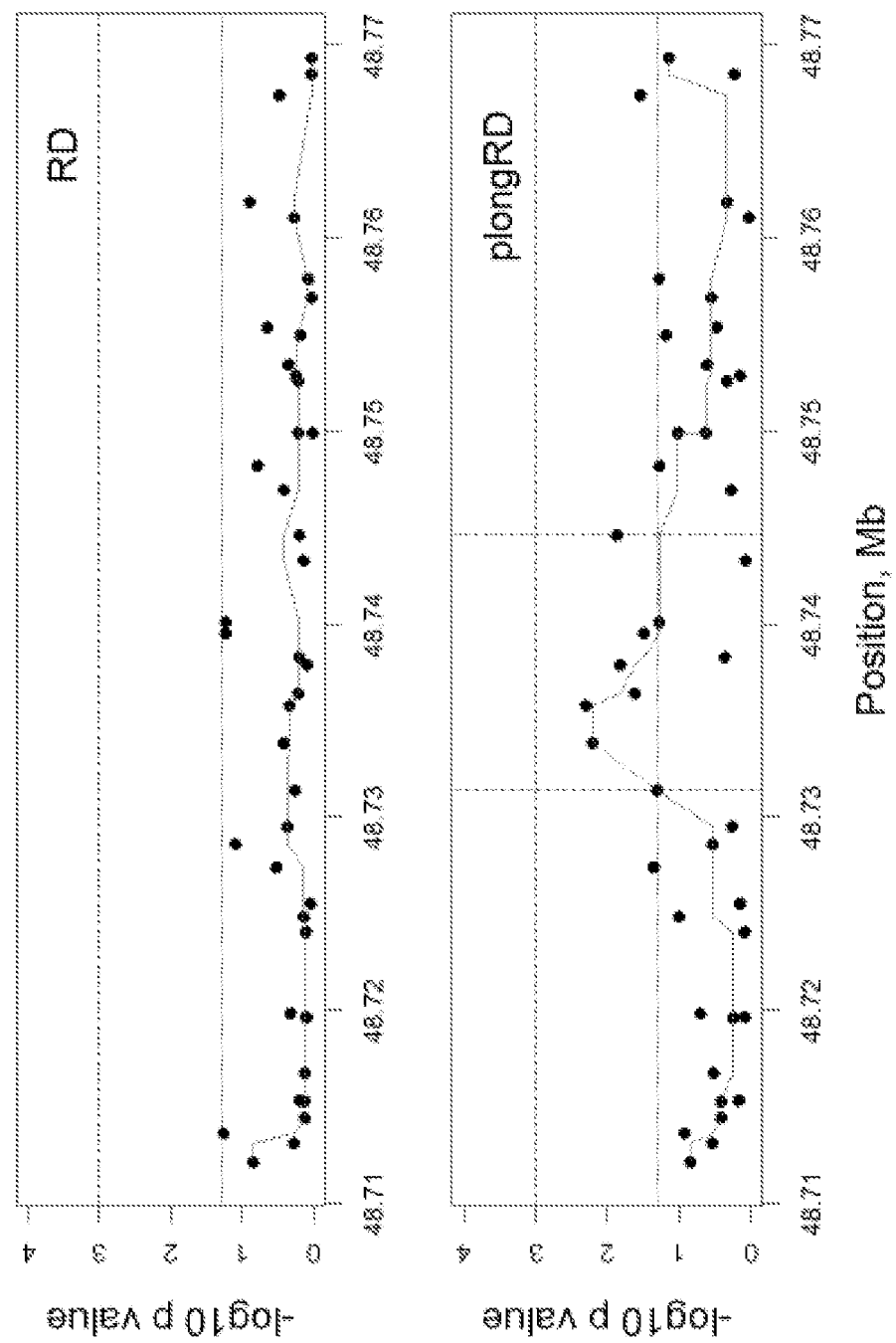
FIG. 9. Associations between postoperative respiratory depression and ABCC3 SNPs from the human Illumina Omni5 GWAS chip.

The following table shows the association of prolonged PACU stay due to respiratory depression for ABCC3 SNPs in the critical region, along with effects depicted as odds ratio (OR) and 95% confidence interval. The odds ratio indicates the ratio when the minor allele (races combined) increased by one copy. FIG. 9 shows the associations between postoperative respiratory depression and ABCC3 SNPs from the human Illumina Omni5 GWAS chip.

TABLE 8

Association of prolonged PACU stay due to RD with ABCC3 SNPs in the critical region

| | SNP | | | minor allele (%) | | | P value | | Putative |
|---|---|---|---|---|---|---|---|---|---|
| outcome | Illumina ID | rs# | location | white | black | all | association | OR (95% CI) | function |
| Prolonged PACU Stay due to RD | kgp9079579 | rs35364174 | 48731392 | G (0.483) | A (0.429) | G (0.497) | 0.0496 | 1.80 (1.00, 3.24) | intron |
| | | rs4148412 | 48733815 | A (0.385) | A (0.367) | A (0.382) | 0.0061 | 2.36 (1.28, 4.37) | intron |
| | | rs739923 | 48735774 | A (0.255) | A (0.225) | A (0.250) | 0.0050 | 0.27 (0.11, 0.68) | intron |
| | | rs733392 | 48736403 | A (0.258) | A (0.174) | A (0.244) | 0.0239 | 0.38 (0.17, 0.88) | intron |
| | | rs1978153 | 48737861 | G (0.388) | G (0.296) | G (0.373) | 0.0152 | 0.44 (0.23, 0.85) | intron |
| | kgp388163 | rs2301837 | 48738266 | A (0.088) | A (0.133) | A (0.095) | 0.4262 | 0.64 (0.22, 1.91) | intron |
| | kgp3814620 | rs7216383 | 48739543 | G (0.238) | A (0.418) | G (0.291) | 0.0316 | 0.45 (0.21, 0.93) | intron |
| | kgp2507665 | rs61479331 | 48740116 | C (0.227) | A (0.490) | C (0.271) | 0.0524 | 0.48 (0.23, 1.01) | intron |

TABLE 8-continued

Association of prolonged PACU stay due to RD with ABCC3 SNPs in the critical region

| outcome | SNP | | | minor allele (%) | | | P value association | OR (95% CI) | Putative function |
|---|---|---|---|---|---|---|---|---|---|
| | Illumina ID | rs# | location | white | black | all | | | |
| | | rs16949202 | 48743275 | G (0.148) | G (0.051) | G (0.133) | 0.8366 | 0.91 (0.38, 2.17) | intron |
| | kgp12280761 | rs886493 | 48744612 | A (0.468) | A (0.449) | A (0.465) | 0.0134 | 0.44 (0.23, 0.85) | intron |

Note:
effects were shown as odds ratio (OR) and 95% CI for prolonged PACU stay due to respiratory depression (RD).
OR indicated the odds ratio when minor allele (races combined) increased by one copy.

In addition, we analyzed the ABCB1, FAAH, and OPRM1 data discussed above with bigger samples. As detailed in the table below, the significance of the association of ABCB1 rs9282564 with respiratory depression leading to prolonged PACU stay (plongRD) and that of FAAH rs324420 with postoperative nausea and vomiting (PONV) was validated with p-values of 0.0002 and 0.0143. The results indicated that patients having the minor allele in each case had a higher risk of these adverse events as indicated by the odds ratio.

TABLE 9

Association of Variants with Clinical Outcomes

| Gene | SNP | outcome | minor allele | Sample (N) | p-value | odds ratio (95% CI) |
|---|---|---|---|---|---|---|
| OPRM1 | rs1799971 (A118G) | RD | G | 339 | 0.1586 | |
| OPRM1 | rs1799971 (A118G) | total morphine | G | 339 | 0.3552 | |
| OPRM1 | | RD | GG + GA | 339 | 0.3159 | |
| OPRM1 | | total morphine | GG + GA | 339 | 0.2264 | |
| ABCB1 | rs9282564 | plongRD | G | 339 | 0.0002 | 4.27 (1.97-9.23) |
| FAAH | rs324420 | PONV | A | 339 | 0.0143 | 1.74 (1.12-2.71) |

Example 4

Association of OPRMI A118G Variant with Risk of Morphine-Induced Respiratory Depression Following Spine Fusion in Adolescents This study was conducted to determine whether the OPRM1 A118G variant can affect susceptibility to morphine-induced respiratory depression (MIRD). This example was later published as Chidambaran et al. *The Pharmacogenomics Journal* (2014) 1-8, the contents of which are hereby incorporated by reference.

Figure 7A:
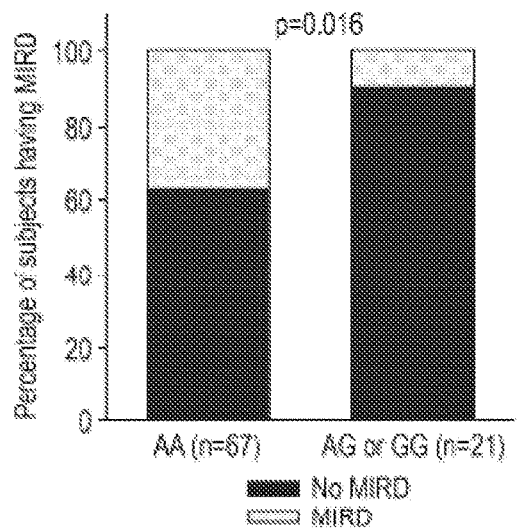
FIG. 7A-7C. The graphs illustrate the influence of OPRM1 rs1799971 variation on morphine-induced respiratory depression (MIRD) and pain outcomes on postoperative days 1 and 2. Incidences of MIRD in different genotypes (A); Risk of MIRD in different genotypes (B); Pain scores and cumulative morphine doses for different genotypes (C).
Figure 7B:
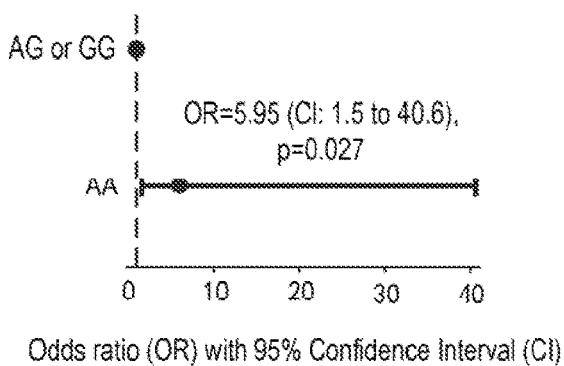
Figure 7C:
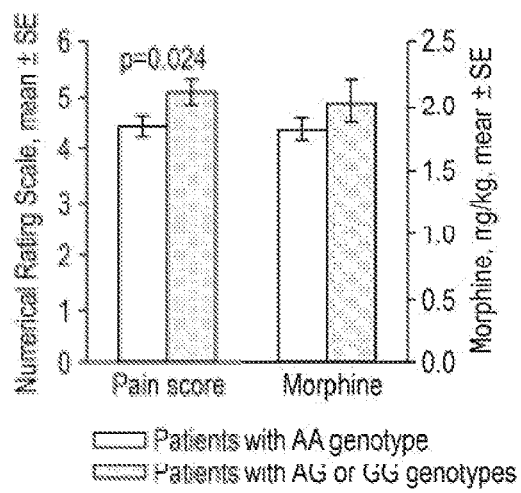

After IRB approval and consent, a prospective genotype blinded study was conducted in 88 non-obese adolescents with idiopathic scoliosis who underwent posterior spine fusion. All patients received morphine patient controlled analgesia after surgery and were followed for 48 hours. MIRD outcome was defined as postoperative occurrence of RR<8/minute for >3 minutes requiring corrective actions. Data regarding morphine consumption, postoperative pain scores, use of diazepam, and other analgesics was recorded. Patients were genotyped for the OPRM1 A118G variant. Regression analysis for factors affecting OIRD included race, sex, morphine requirement, and genotype. Pain scores and related variables in genotype sub-groups were compared. Subjects enrolled were 11-19 years old; 59 female, 85% white. Based on OPRM1 genetic variant, 67 were homozygous for wild-type (AA), 21 heterozygous/homozygous for variant (AG/GG). 37% with AA genotype had MIRD on POD1/2, while only 9% of those with GG/AG genotype had MIRD (FIG. 7A). MIRD in patients with AA genotype were significantly higher (>5 fold) compared to patients caring the G allele (OR 95% CI:1.5-40.6, p=0.027) after adjusting for variables (FIG. 7B). Compared to the AA genotype, children with AG/GG genotypes had significant higher pain scores (p=0.02) and higher morphine requirement on POD1/2 (FIG. 7C).

This is the first prospective clinical trial showing the risk of respiratory depression is higher in the OPRM1 AA genotype despite less morphine requirement than AG/GG genotypes. The presence of the G allele at the A118G variant has a protective effect against MIRD. This genotype-respiratory depression association is an important step in predicting children at higher risk and personalizing the use of morphine in children to maximize pain relief while minimizing the likelihood of serious adverse effects.

Example 5

Genetic Risk Signatures of Opioid-Induced Respiratory Depression Following Pediatric Tonsillectomy In order to translate genetic research finding to clinical practice and better clinical adaptability of important implications of genetic risk factors, easy applicable clinical decision rules based on multivariate predictors must be developed. The aim of this study was to develop reliable and stable models for the prediction of susceptibility for morphine-induced respiratory depression using genetic and non-genetic factors. This example was later published as Biesiada et al., *Pharmacogenomics* (2014) 15(14): 1749-1762, the contents of which are hereby incorporated by reference.

Identifying genetic risk factors for respiratory depression is complicated by gene-gene interactions (associations of individual genes/markers with RD are weak) and by interactions with race and ancestry, various clinical conditions, such as OSA, and even cultural background, which can affect pain tolerance and the resulting dose of opioids used to ameliorate the pain. As a result, strategies to stratify patients into distinct subtypes can help identify stronger (and possibly distinct in each subtype) patterns of associations between SNPs (or other markers) and RD.

In this study, both supervised and unsupervised approaches were used to achieve this goal. Recursive partitioning using decision trees provides inherent stratification of the data and optimizes selection of predictive SNPs (and their combinations) and the overall accuracy. In addition, decision trees provide simple to interpret decision rules that can be used as a basis for clinical decision support. An unsupervised clustering approach can provide an alternative stratification of the cohort into clusters of patients sharing alleles at multiple SNPs as well as other features that may be relevant to capture complex interactions mentioned above. SNPs (and clinical variables such as OSA) that contribute most to defining distinct clusters can be regarded as "SNP signatures" of those clusters (subtypes), in analogy with gene signatures that define molecular subtypes of cancer, for instance.

Using complementary classification (recursive partitioning) and clustering (SNP signature) strategies can also facilitate the validation the results and uncover hidden structure in the data. This study found that results of the two approaches yielded largely consistent results. Several SNPs were found that contribute to both distinct clusters, characterized by significantly different risks of RD. Decision rules that can be used to predict RD with relatively high accuracy within specific strata were also identified. The results are summarized below.

Study Design, Participants, and Procedures

After appropriate IRB approval and consent, a prospective genotype-blinded trial was conducted in 273 children, aged 6-15 years, undergoing tonsillectomy, who received morphine as part of standard perioperative care. All patients were observed in the recovery room for morphine requirements, pain outcomes and occurrence of RD, the primary outcome studied. RD was defined as a respiratory rate <10 breaths per minute or persistent oxygen desaturation <92% requiring supplemental oxygen to maintain SpO2 >92% in the absence of clinically obvious upper airway obstruction. All patients were genotyped for 48 single-nucleotide polymorphisms (SNPs) in 15 genes known to be involved in the morphine pharmacokinetic and respiratory depression pathway using TaqMan assays. Genetic and non-genetic factors (race, sex, OSA) were analyzed for association with risk of RD and a stepwise risk-based algorithm was constructed using simple logical rules and decision tree approach.

Results

This study considered the risk of RD in patients who required an additional post-operative dose of morphine to ameliorate their pain (170 out of 273 patients, of which 45 had RD). Stratifying the analysis in this way allowed the analysis to better take into account interactions between higher pain sensitivity, race, and OSA (due to higher risk of adverse effects, patients with OSA obtain a lower starting dose of morphine as a precaution). Qualitatively similar results were obtained for a subset of patients who received a high dose of morphine (defined as higher than 0.3 mg/kg, as opposed to the baseline of 0.2 for non-OSA and 0.1 for OSA patients), indicating that such identified decision rules can be used to guide clinical decisions regarding additional doses of morphine given the predicted risk of RD.

Figure 8A:
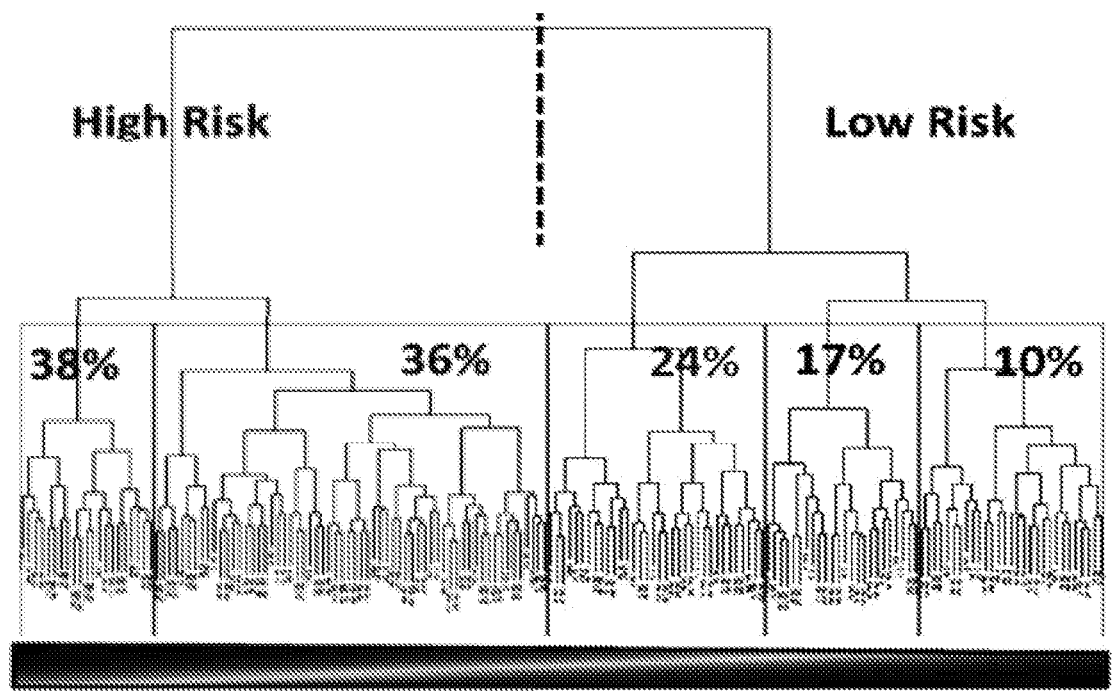
FIG. 8A-8B. The use of SNP signatures to identify high vs. low risk subtypes among patients requiring post-surgical intervention, with 3 SNPs allowing one to capture most of the signal. The percent of RD cases in each cluster (A); Decision tree that classifies patients into low vs. high risk strata, wherein rs2295632_A=No denotes the lack of A allele, i.e. CC, and rs2295632=Yes corresponds to CA and AA genotypes (B).

Using an unsupervised clustering approach and all SNPs included in the analysis (excluding those in high LD with each other), 5 clusters were identified, with the risk of RD increasing gradually from about 10% for the "low risk cluster" to about 40% for the "high risk cluster" (FIG. 8A). It should be noted that several clinical/demographic variables were used at that stage, including race, OSA, and sex. However, while biasing clustering results, these variables did not show an obvious association with the clusters identified. Using centroids of such defined clusters (resembling a "gene signatures"-based approach for cancer subtype classification; here SNP signatures are used to determine risk subtypes), yielded an accuracy of about 82% for high vs. intermediate vs. low risk assignment.

Analysis of such obtained strata reveals that most of the discriminatory signal comes from just a handful of SNPs. This is highlighted by the fact that the combination of three SNPs, namely rs2295632 (FAAH), rs1045642 (ABCB1), and rs1042713 (ADRB2), improves discrimination of RD cases as compared with univariate analyses. Using a simple decision rule derived from the decision tree shown in FIG. 8B yields a p-value of 0.000003 (as opposed to 0.0002 for the top discriminating SNP rs2295632 alone), allowing one to identify low vs. high risk strata, with a balanced accuracy of about 70% on the set of patients who required postoperative intervention:

IF [(rs2295632=CC) OR (rs1045642=CC) OR (rs1042713=AA)] THEN RD=NO (low risk of RD)
ELSE RD=YES (high risk of RD).

Figure 8B:
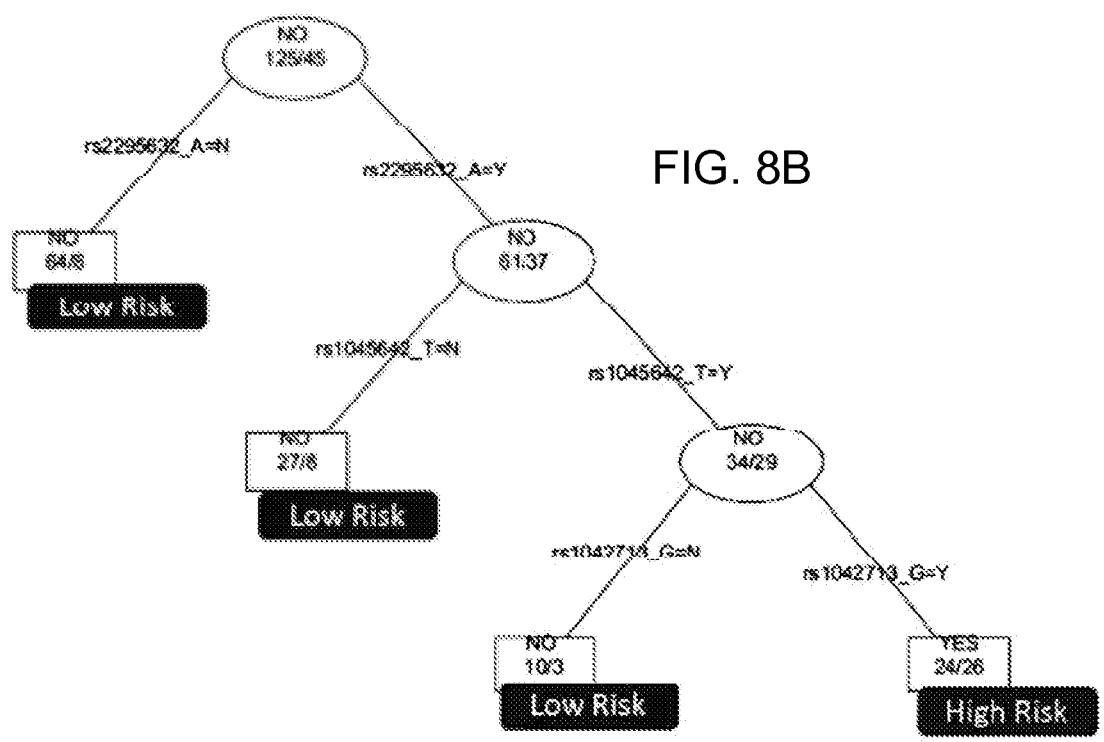

The above decision rule identifies high risk patients as those who have risk alleles at all three loci included (the upmost right leaf of the tree in FIG. 8B, with 26 cases of RD=YES and 24 cases RD=NO). The "SNP signatures" presented herein were derived using an unsupervised approach (and therefore did not require optimization of parameters in the model on the training set), which bodes well for their generalization. The hierarchical clustering of this data is shown in the published version of this work, *Pharmacogenomics*, 15(14):1749-1762 (2014).

These findings were validated by testing for the effect of SNP selection, allele encoding (allelic vs. dominant-recessive based), inclusion of additional stratification criteria (e.g. high dose of morphine vs. intervention needed). PVCLUST was also used to perform bootstrapping to further assess the stability of clustering patterns observed. Support for the main 5 clusters was high, while their overall order was much less stable and had low support, suggesting that further improvements can be achieved.

Figure 10:
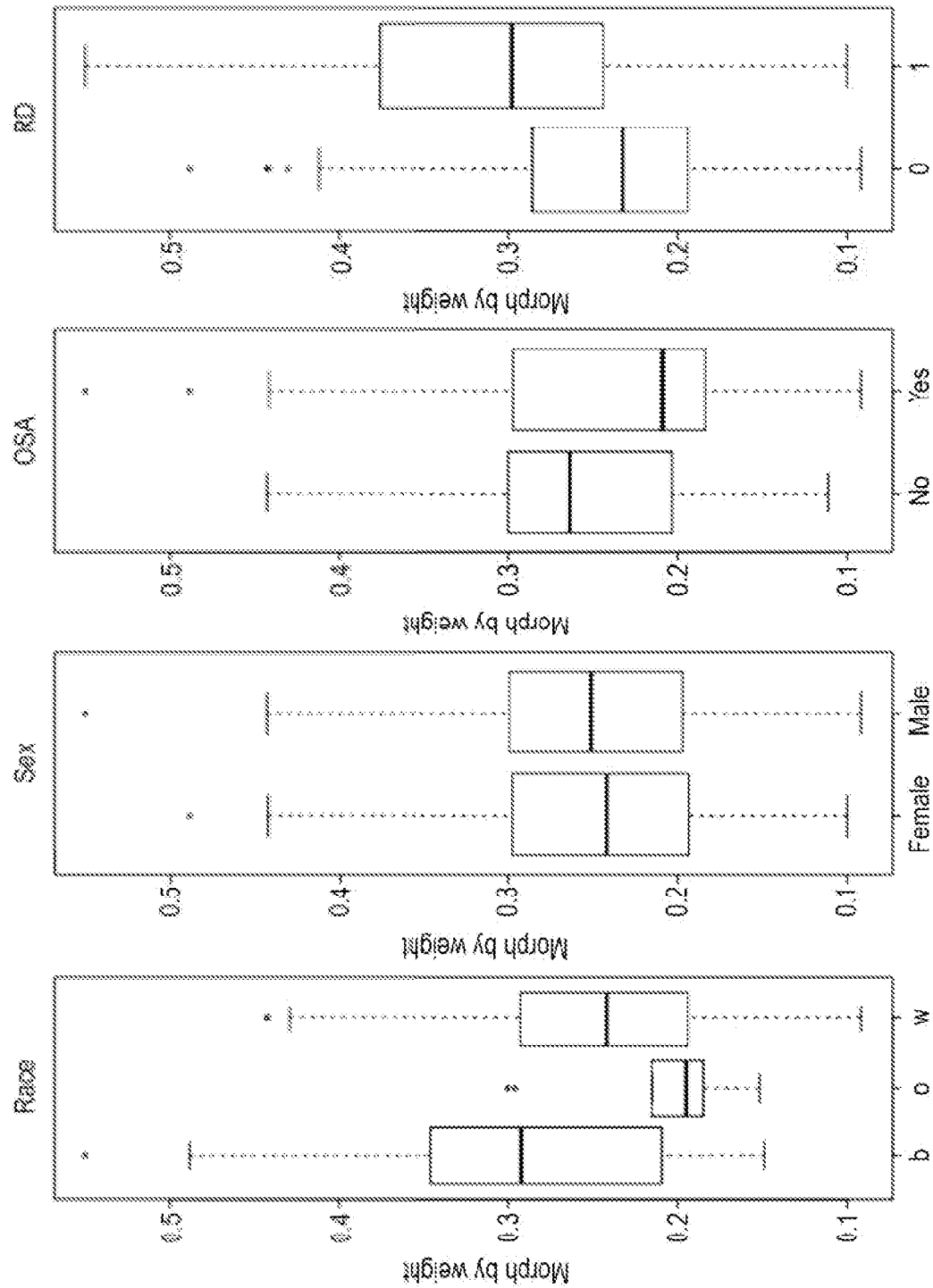
FIG. 10. Correlation of morphine dose with race, sex, OSA (non-OSA: left boxplot; OSA: right boxplot) with RD (no RD: left boxplot; RD: right boxplot). OSA patients had a lower overall dose, and RD risk increased with increasing dose of morphine. These results include the set of 274 patients.

For independent validation, a set of 74 patients for which data has become available since the conclusion of the first phase of the project was used. Clustering these new data points together with the training set of 274 patients reproduced the clustering pattern observed on just the training set of 274. For the new patients from the control set who required intervention, those that were assigned to the low risk cluster had twice fewer RD cases (16%) compared with those assigned to the high risk cluster (30%). In addition, two extreme clusters (with the highest and lowest risk of RD) were in fact somewhat better separated indicating that further improvements can be achieved when even more data becomes available (FIG. 10). After appropriate and independent validations, genotype-based decision algorithms can help to proactively determine underlying risks and tailor perioperative management and form an important foundational step in clinical implementation of personalized analgesia.

Example 6

Opioid-Related Adverse Effects in Children Undergoing Surgery: Unequal Burden on Girls There are no clinical studies in children to study sex-specific responses to opioids in terms of analgesic and adverse effects.

Study of sex differences in morphine effects in the pediatric population is especially important, as the mechanisms underlying them are likely influenced by physiological, developmental and hormonal factors, which may vary between prepubertal children, adolescents and adults. Compared to adults with different comorbid conditions undergoing different surgeries and receiving different perioperative medications, a relatively large number of healthy children undergoing one type of surgery with standardized perioperative management is a better population to study interindividual variations associated with opioids. This study hypothesized that sex of the child affects postoperative analgesic and adverse outcomes with the use of opioids. Therefore, the aim of our study was to determine the role of a child's sex in determining the analgesic property and adverse effects of morphine in children undergoing tonsillectomy. Knowledge about the factors contributing to variable opioid response will help optimize opioid dosing, analgesic outcomes, and inform adverse effect prevention strategies in the future.

Study Design, Participants, and Procedures

Figure 11:
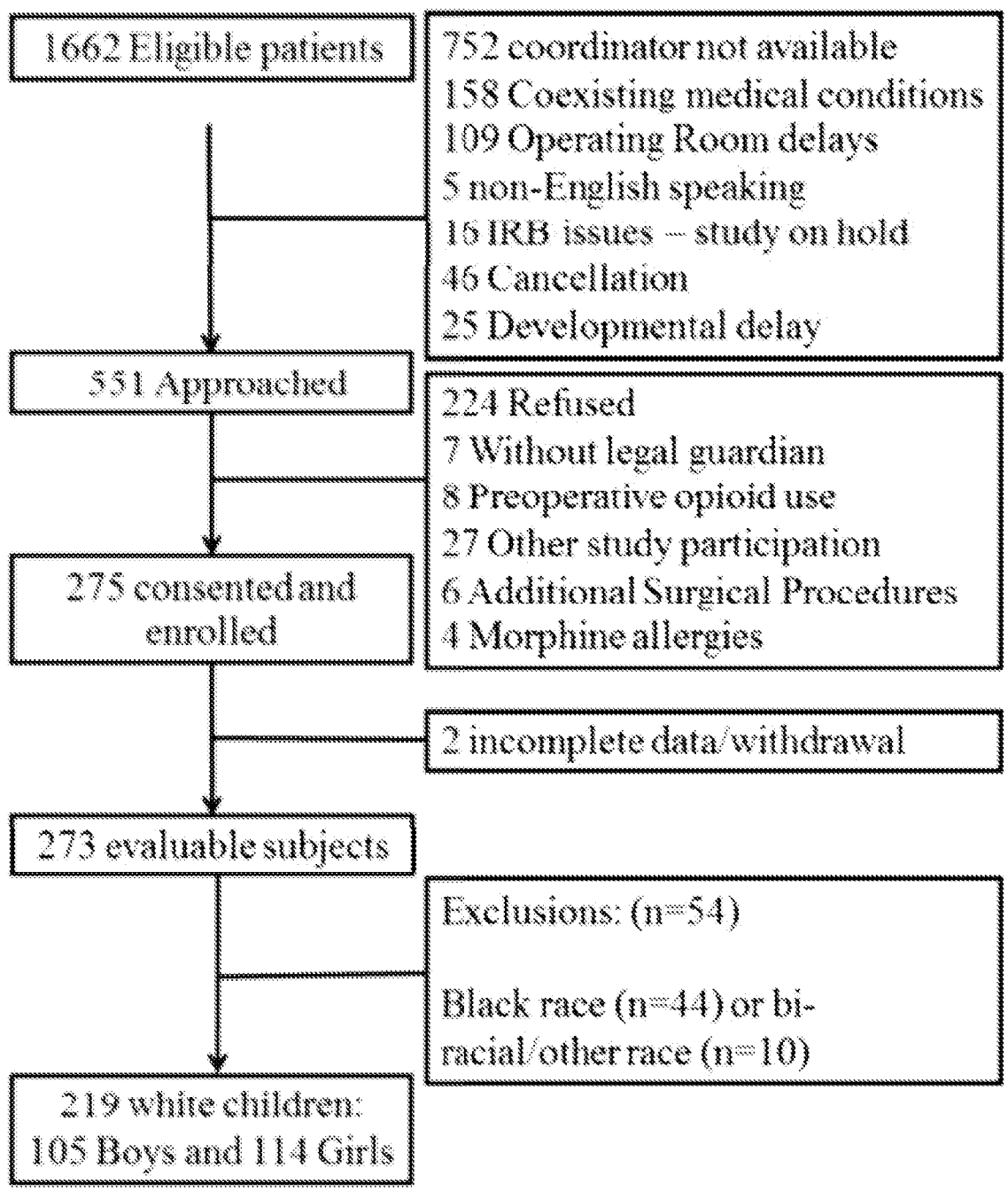
FIG. 11. The consort diagram illustrates the flow of study participants through this clinical trial. Eligible participants, reasons for exclusions, and enrolled patients are reported. IRB=institutional review board.

This was a prospective clinical observational study using a standard perioperative anesthetic and surgical practices and standard postoperative nursing care within the tonsillectomy population. This study was approved by the institutional review board at Cincinnati Children's Hospital Medical Center, Cincinnati, Ohio, USA, and written informed consents and assents, when appropriate, were obtained from all parents and participating children. In this project there was no selection for specific races, however, given the demographics of patients for tonsillectomy or adenotonsillectomy (T/TA) surgery at the hospital, the vast majority of patients were white (FIG. 11). While data for multiple races were available, given the small sample sizes of the non-white boys and girls, this study focused on white children and examined the effect of sex in white children because previous research showed differences in opioid related adverse events in children by race, with white children having relatively more adverse effects than black children (Sadhasivam S. et al., *Pediatrics,* 129:832-8 (2012)).

Children 6-15 years undergoing elective outpatient T/TA who were eligible for the study were approached and recruited on the day of surgery between August 2008 and February 2012. Race was self-reported by either the parent or child; self-report is well accepted for identifying race (Boehmer U. et al., *American Journal of Public Health,* 92:1471-2 (2002); Dahan A. et al., *Anesthesiology,* 88:903-13 (1998)). Sample inclusion criteria were children designated to have an American Society of Anesthesiologists (ASA) physical status 1 or 2 scheduled for T/TA because of recurrent tonsillitis, adenotonsillar hypertrophy or OSA. Clinical criteria for OSA designation included sleep disordered breathing with a history of snoring and either sleep pauses lasting more than 10 seconds or daytime drowsiness. Children were excluded from the study if they or their parents were non-English speaking. Children who were allergic to morphine or who had developmental delay, liver or renal disease, or preoperative pain requiring opioid analgesics (e.g. chronic tonsillitis) were excluded. Due to limited availability of research coordinators for this study, not all eligible subjects were able to be recruited (FIG. 11).

As part of T/TA standard practice at this institution, all children receive prophylactic ondansetron (0.1 mg/kg) and dexamethasone (0.1 mg/kg) intraoperatively. Anesthesia is induced via sevoflurane inhaled induction followed by a propofol (2 mg/kg) bolus to facilitate endotracheal intubation. Anesthesia was maintained with sevoflurane without the use of neuromuscular blockade. Patients receive morphine for pre-emptive analgesia prior to surgical incision. Children with OSA history receive 0.1 mg/kg morphine while those without OSA diagnosis receive 0.2 mg/kg. If there are any signs suggestive of pain (clinically significant increase in heart rate and blood pressure) following surgical incision and cauterization, the clinical anesthesia team provides additional morphine intraoperatively as necessary.

Outcomes

Outcomes for analgesic effectiveness and opioid-related adverse effects were collected. Analgesic effectiveness outcomes included post-operative pain scores, morphine doses (mg/kg), need for intravenous analgesic intervention (yes/no), prolonged PACU stay (>90 minutes) due to pain (yes/no), and the number of total analgesic interventions given. In addition, subjective and objective pain scores were assessed using a 0 to 10 Numerical Rating Scale (NRS) (Voepel-Lewis T. et al., *Anesth. Analg.,* 112:415-21 (2011)) and a 0 to 10 FLACC (facial expression; leg movement; activity; cry; and consolability) scale (Merkel S. et al., *Pediatr. Nurs.,* 23:293-7 (1997)), respectively. Significant postoperative pain (NRS or FLACC ≥4/10) was managed in the PACU with rescue doses of morphine (0.05 mg/kg). The maximum NRS and FLACC scores were examined.

Adverse effects were measured by two sets of binary outcomes: 1) opioid-related side effects including RD, nausea/vomiting (PONV) and pruritus; 2) prolonged PACU stay secondary to respiratory depression or nausea/vomiting. In our study, RD was defined as a persistent respiratory rate <10 breaths per minute or persistent oxygen desaturation <92% requiring supplemental oxygen to maintain SpO2 >92% in the absence of clinically obvious upper airway obstruction and artifacts for one minute or longer.

Duration of PACU stay (time to achieve PACU discharge readiness) was defined as the duration in PACU before achieving the following discharge criteria. Level of consciousness: easily arousable or awake, airway: patent with adequate air exchange, core body temperature: ≥36.3 degrees Celsius, acceptable pain level (pain score <4), hemodynamically stable, no significant opioid related adverse effects, such as PONV and respiratory depression, and surgical site without any bleeding or complications. This discharge readiness time is different from actual PACU discharge time as delays due to social reasons (e.g. waiting for car ride, etc.) were not included.

Statistical Analysis

Prior to analyses, data quality was examined. Since only 44 African-Americans and 10 other races were included, analyses were performed on whites. To assess the sex effect, outcome measurements were first compared between boys and girls with and without OSA stratification. Continuous variables were compared using t-test or Wilcoxon rank-sum test and categorical variables were compared using Fisher's exact test. To analyze morphine effects, intra-operative and total morphine doses (mg/kg) were categorized into low, medium, and high (≤0.1, >0.1-0.2, >0.2 for intra-operative morphine and <0.2, 0.2-0.3, and >0.3 for total morphine).

Spearman correlation coefficients were used to assess the relationship between morphine dose and outcomes by sex.

Multivariate statistical modeling was then performed to formally test the sex effect and the interaction of sex and morphine dose while accounting for covariate effects. For analgesic effectiveness outcomes, intra-operative morphine was used as a covariate; for side effects outcomes, total morphine requirement (calculated as the sum of the intra- and post-operative morphine dose) was used as a covariate. Effects of age, weight, BMI z scores, and OSA were also tested as covariates for all the outcomes. When significant effects were detected (p<0.05), covariates were included in the final models. Binary outcomes were analyzed using logistic regression. Maximum NRS was analyzed using linear regression. Maximum FLACC score was analyzed by using a zero-inflated negative binomial model because of the inflated frequency of score 0. The total number of analgesic interventions followed a Poisson distribution and was analyzed using a generalized linear model. Postoperative morphine dose was analyzed in patients who needed intervention using a linear regression.

To examine whether the relationship between side effects and total morphine dose differs by age, female patients were grouped into three age groups: less than 8 years, 8 to 13 years, and greater than 13 years of age to classify females as pre, peri, and postpubertal in lieu of formal Tanner staging. In this analysis, total morphine requirement was dichotomized into ≥0.3 or <0.3 mg/kg dose ranges because of a potential threshold effect of morphine. The linear trends between total morphine and PONV, RD, prolonged PACU due to PONV and RD were assessed separately in the three age groups. This hypothesis was then formally tested using multivariate logistic models.

Statistical analyses were performed using Statistical Analysis Software, version 9.3 (SAS Institute Inc., Cary, N.C.). Eleven correlated outcomes were examined with a mean Spearman correlation coefficient of 0.26. A correlation-adjusted Bonferroni correction (http<colon slash slash>www<dot>quantitativeskills<dot>com<slash>sisa) yielded a significance threshold of 0.008. Association reaching the threshold of 0.05 was also reported. This may help to identify potential associations for future studies, but caution has to be taken when interpret these results due to the inflated type I error rate.

Results

A consort diagram illustrates eligible, approached and enrolled study subjects (FIG. 11). Due to relatively smaller sample sizes of non-white children (44 African-Americans and 10 other races or biracial), this study focused on 219 white children (114 girls and 105 boys). Though mean age and weight were comparable, girls had a higher incidence of OSA (50% vs. 36%, p=0.04) (Table 10). Age and BMI were comparable between boys and girls.

When all doses of total morphine were grouped together, no significant differences were detected in any of the analgesia and opioid related adverse outcomes in univariate analyses (Table 11) or multivariate modeling (data not shown). Stratifying by OSA did not affect these results.

TABLE 10

Demographic characteristics and perioperative morphine use.

| | Female (N = 114) | Male (N-105) | P Value |
|---|---|---|---|
| Age (year) | 8.4 (7.1, 11.6) | 8.4 (6.9, 10.4) | 0.16 |
| Weight (Kg) | 36.1 (26.0, 48.0) | 33.3 (25.8, 43.6) | 0.25 |
| BM I z score | 0.9 (−0.2, 1.6) | 0.6 (−0.2, 1.6) | 0.93 |
| Intra-op morphine (mg/kg) | 0.19 (0.16, 0.21) | 0.19 (0.18, 0.21) | 0.42 |
| Total morphine (mg/kg) | 0.23 (0.19, 0.29) | 0.25 (0.20, 0.29) | 0.13 |
| Age group | | | |
| >13 year | 15 (13%) | 8 (8%) | 0.39 |
| 8-13 year | 52 (46%) | 49 (47%) | |
| <8 year | 47 (41%) | 48 (46%) | |
| Intra-op morphine group | | | 0.86 |
| 0.1-0.2 mg/kg | 71 (62%) | 68 (65%) | |
| >0.2 mg/kg | 43 (38%) | 37 (35%) | |
| Total morphine group | | | 0.71 |
| <0.2 mg/kg | 41 (36%) | 33 (31%) | |
| 0.2-0.3 mg/kg | 50 (44%) | 47 (45%) | |
| >0.3 mg/kg | 23 (20%) | 25 (24%) | |
| OSA | | | 0.039 |
| No | 57 (50%) | 67 (64%) | |
| Yes | 57 (50%) | 38 (36%) | |

BMI z score was calculated using the CDC growth charts.

Age, weight, BMI z scores, intra-op morphine, and total morphine requirement are shown as median and IQR for the entire study cohort and compared using the Wilcoxon rank sum test. Age group, intra-operative and total morphine groups, and OSA are shown as number and proportions, and compared using Pearson chi-square test.

OSA = Obstructive sleep apnea.

TABLE 11

Sex differences in analgesia and opioid adverse effect outcomes.

| | | No | P value | Yes | P value | All | p value |
|---|---|---|---|---|---|---|---|
| Post-operative morphine (mg/Kg) | F | 0.08 ± 0.04 | 0.31 | 0.09 ± 0.06 | 0.89 | 0.09 ± 0.05 | 0.60 |
| | M | 0.09 ± 0.05 | | 0.09 ± 0.05 | | 0.09 ± 0.05 | |
| Maximum NRS pain Score | F | 6 (3-9) | 0.25 | 5 (2-9) | 0.92 | 6 (2-9) | 0.38 |
| | M | 6 (3-8) | | 5 (2-8) | | 5 (3-8) | |
| Maximum FLACC pain score | F | 2 (0-4) | 0.84 | 2 (0-5) | 0.08 | 2 (0-5) | 0.25 |
| | M | 2 (0-5) | | 4 (1-7) | | 2 (1-5) | |
| Number of analgesic interventions | F | 1 (0-1) | 0.3 | 1 (0-1) | 0.26 | 1 (0-1) | 0.88 |
| | M | 1 (0-1) | | 1 (0-2) | | 1 (0-1) | |
| Prolonged PACU stay due to pain | F | 21 (17%) | 1 | 16 (17%) | 0.82 | 37 (17%) | 0.78 |
| | M | 24 (19%) | | 12 (13%) | | 36 (16%) | |

TABLE 11-continued

Sex differences in analgesia and opioid adverse effect outcomes.

|  |  | No | P value | Yes | P value | All | p value |
|---|---|---|---|---|---|---|---|
| Analgesic Intervention need in PACU | F | 35 (28%) | 0.36 | 32 (34%) | 0.28 | 67 (31%) | 1.00 |
|  | M | 35 (28%) |  | 26 (27%) |  | 61 (28%) |  |
| RD | F | 9 (7%) | 0.81 | 11 (12%) | 0.79 | 20 (9%) | 1.00 |
|  | M | 12 (10%) |  | 6 (6%) |  | 18 (8%) |  |
| PONV | F | 11 (9%) | 0.20 | 11 (12%) | 1.00 | 22 (10%) | 0.28 |
|  | M | 7 (6%) |  | 7 (7%) |  | 14 (6%) |  |
| Pruritus | F | 41 (33%) | 0.54 | 47 (50%) | 0.30 | 88 (41%) | 0.75 |
|  | M | 51 (41%) |  | 28 (30%) |  | 79 (36%) |  |
| Prolonged stay in PACU due to RD | F | 5 (4%) | 0.77 | 6 (6%) | 0.75 | 11 (5%) | 0.53 |
|  | M | 8 (6%) |  | 5 (5%) |  | 13 (6%) |  |
| Prolonged stay in PACU due to PONV | F | 2 (2%) | 0.29 | 8 (8%) | 0.31 | 10 (5%) | 0.81 |
|  | M | 6 (5%) |  | 2 (2%) |  | 8 (4%) |  |

Post-operative morphine was shown as mean + SD and was compared using t-test. It was examined only in patients who needed post-operative morphine.
Number of analgesic interventions, maximum NRS, and FLACC scores were shown as median (IQR), and were compared using Wilcoxon rank sum tests.
Dichotomous variables were shown as number of cases (proportion), and were compared using Fisher's Exact test.
F: female;
M: male,
PACU: post anesthesia recovery unit,
RD: respiratory depression,
PONV: post-operative nausea and vomiting

TABLE 12

Sex-specific association of adverse effects and total morphine doses.
Total Morphine by Weight (mg/kg)

|  |  | <0.2 Number of cases (%) | 0.2-<0.3 Number of cases (%) | ≥0.3 Number of cases (%) | p value |
|---|---|---|---|---|---|
| RD | F | 5 (12) | 3 (6) | 12 (52) | 0.001 |
|  | M | 4 (12) | 6 (13) | 8 (32) | 0.079 |
| PONV | F | 4 (10) | 8 (16) | 10 (43) | 0.003 |
|  | M | 6 (18) | 7 (15) | 1 (4) | 0.172 |
| Pruritus | F | 29 (73) | 42 (84) | 17 (74) | 0.636 |
|  | M | 24 (73) | 35 (76) | 20 (80) | 0.521 |
| Prolonged stay in PACU due to RD | F | 2 (5) | 1 (2) | 8 (35) | 0.002 |
|  | M | 5 (15) | 3 (6) | 5 (20) | 0.841 |
| Prolonged stay in ACU due to PONV | F | 2 (5) | 3 (6) | 5 (22) | 0.068 |
|  | M | 4 (12) | 3 (6) | 1 (4) | 0.295 |

*: exact test on the Spearman correlation coefficient
F: female;
M: male,
PACU: post anesthesia recovery unit,
RD: respiratory depression,
PONV: post-operative nausea and vomiting

TABLE 13

Sex-specific association of analgesia and total morphine doses.

|  |  | Intra-op Morphine by Weight 9 mg/kg) | | |  |
|---|---|---|---|---|---|
|  |  | ≤0.1 Mean ± SD Median (IQR) Number of Cases (%) | >0.1-0.2 Mean ± SD Median (IQR) Number of Cases (%) | >0.2 Mean ± SD Median (IQR) Number of Cases (%) | p value* |
| Post-operative morphine (mg/Kf) | F | 0.07 + 0.03 | 0.09 + 0.05 | 0.10 + 0.05 | 0.90 |
|  | M | 0.07 + 0.04 | 0.10 + 0.05 | 0.09 + 0.05 | 0.83 |
| Maximum NRS pain score | F | 8 (6-10) | 5 (2-8) | 6 (3-9) | 0.75 |
|  | M | 6 (5-9) | 5 (2-8) | 6 (4-7) | 0.95 |
| Maximum FLACC pain score | F | 3 (3-4) | 2 (0-5) | 1 (0-5) | 0.24 |
|  | M | 3 (1-5) | 3 (1-7) | 2 (0-5) | 0.20 |
| Number of analgesic interventions | F | 1 (1-2) | 1 (0-1) | 1 (0-1) | 0.22 |
|  | M | 1 (1-2) | 1 (0-1) | 1 (0-1) | 0.40 |
| Prolonged PACU stay due to pain | F | 3 (60) | 22 (33) | 12 (28) | 0.28 |
|  | M | 2 (33) | 22 (35) | 12 (32) | 0.85 |
| Analgesic | F | 5 (100) | 40 (61) | 22 (51) | 0.10 |

TABLE 13-continued

Sex-specific association of analgesia and total morphine doses.

|  | Intra-op Morphine by Weight 9 mg/kg) | | | |
|---|---|---|---|---|
|  | ≤0.1<br>Mean ± SD<br>Median (IQR)<br>Number of<br>Cases (%) | >0.1-0.2<br>Mean ± SD<br>Median (IQR)<br>Number of<br>Cases (%) | >0.2<br>Mean ± SD<br>Median (IQR)<br>Number of<br>Cases (%) | p value* |
| Intervention need<br>in PACU | M 5 (83) | 36 (58) | 20 (54) | 0.35 |

*exact test on the Spearman correlation coefficient.
Post-operative morphine was shown as mean + SD, and was examined in patients who needed morphine post.
Number of analgesic intervention, maximum NRS and FLACC score was shown as median (IQR)
Dichotomous variables were shown as number of cases (proportion).
F: female;
M: male;
PACU: post anesthesia recovery unit,
NRS = numerical scale.

TABLE 14

Opioid-related adverse effects in younger versus older girls by total morphine group.

|  |  | Total Morphine by Weight (mg/kg) | | |
|---|---|---|---|---|
| Opioid-related adverse effects | Age in years | <0.3<br>Number<br>of cases<br>(%) | >=0.3<br>Number<br>of cases<br>(%) | p value* |
| Respiratory depression (RD) | >13 | 1 (9) | 2 (50) | 0.15 |
|  | 8-13 | 4 (9) | 5 (56) | 0.0045 |
|  | <8 | 3 (8) | 5 (50) | 0.0067 |
| Prolonged stay in PACU due<br>to RD | >13 | 0 (0) | 1 (25) | 0.27 |
|  | 8-13 | 1 (2) | 3 (33) | 0.0138 |
|  | <8 | 2 (5) | 4 (40) | 0.0139 |
| PONV | >13 | 1 (9) | 0 (0) |  |
|  | 8-13 | 2 (5) | 1 (11) |  |
|  | <8 | 7 (19) | 6 (60) | 0.0175 |
| Prolonged stay in PACU due<br>to PONV | >13 | 1 (9) | 0 (0) | 1.00 |
|  | 8-13 | 2 (5) | 1 (11) | 1.00 |
|  | <8 | 2 (5) | 4 (40) | 0.0139 |

PACU: post anesthesia recovery unit,
PONV: post-operative nausea and vomiting.
*exact test on the Spearman correlation coefficient.

Figure 12A:
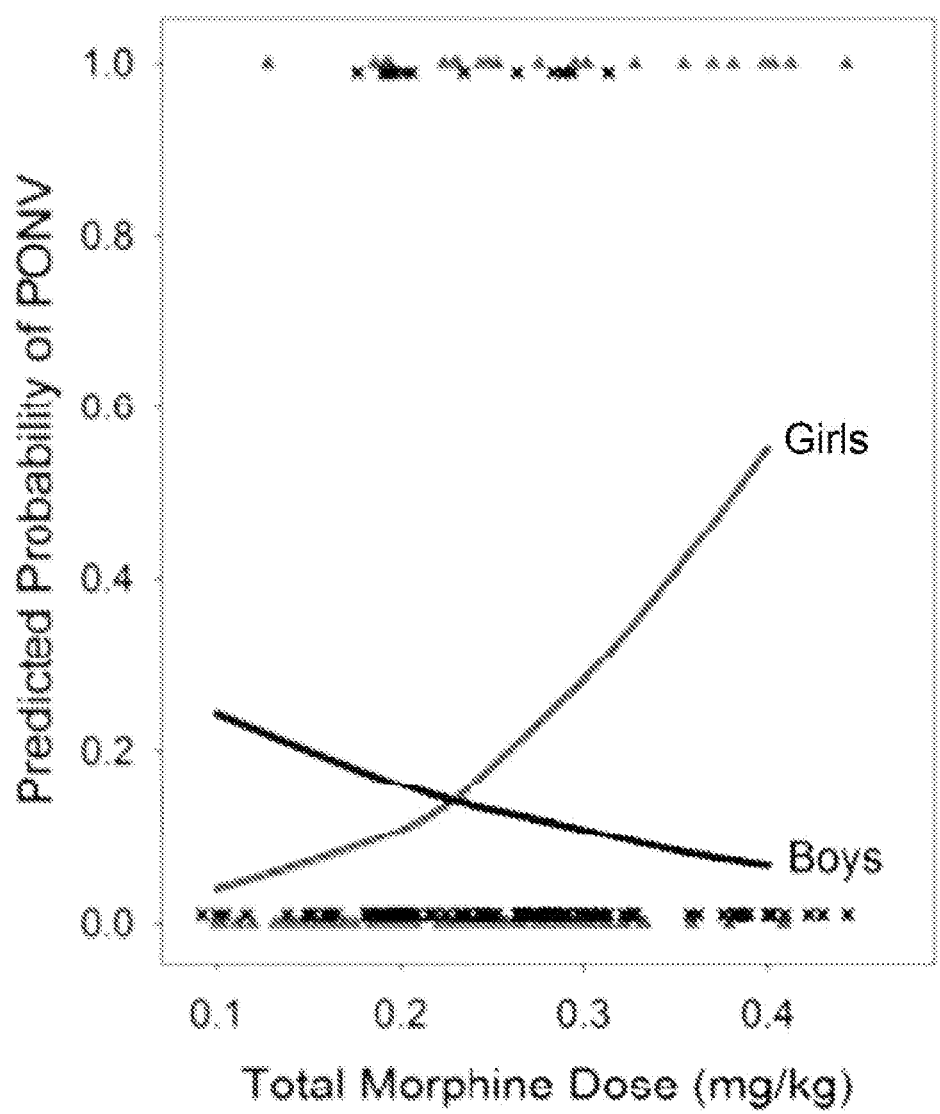
FIG. 12A-12B. Sex-specific differences in morphine-related postoperative nausea and vomiting (PONV) in post-anesthesia recovery unit (PACU). A: Sex-specific differences in morphine-related PONV in PACU. Total morphine dose is plotted in the X-axis, and the probabilities of morphine related PONV are plotted in the Y-axis for boys and girls. Overall incidences of opioid-related PONV in the PACU were relatively higher in girls compared with boys as the total morphine dose increased. B: Sex-specific differences in morphine-related PONV resulting in prolonged stays in PACU. Total morphine dose is plotted in the X-axis, and the probabilities of prolonged PACU stay due to PONV are plotted in the Y-axis for boys and girls. The probability of PONV leading to prolonged PACU stay was relatively higher in girls compared with boys as the total morphine dose increased.
Figure 12B:
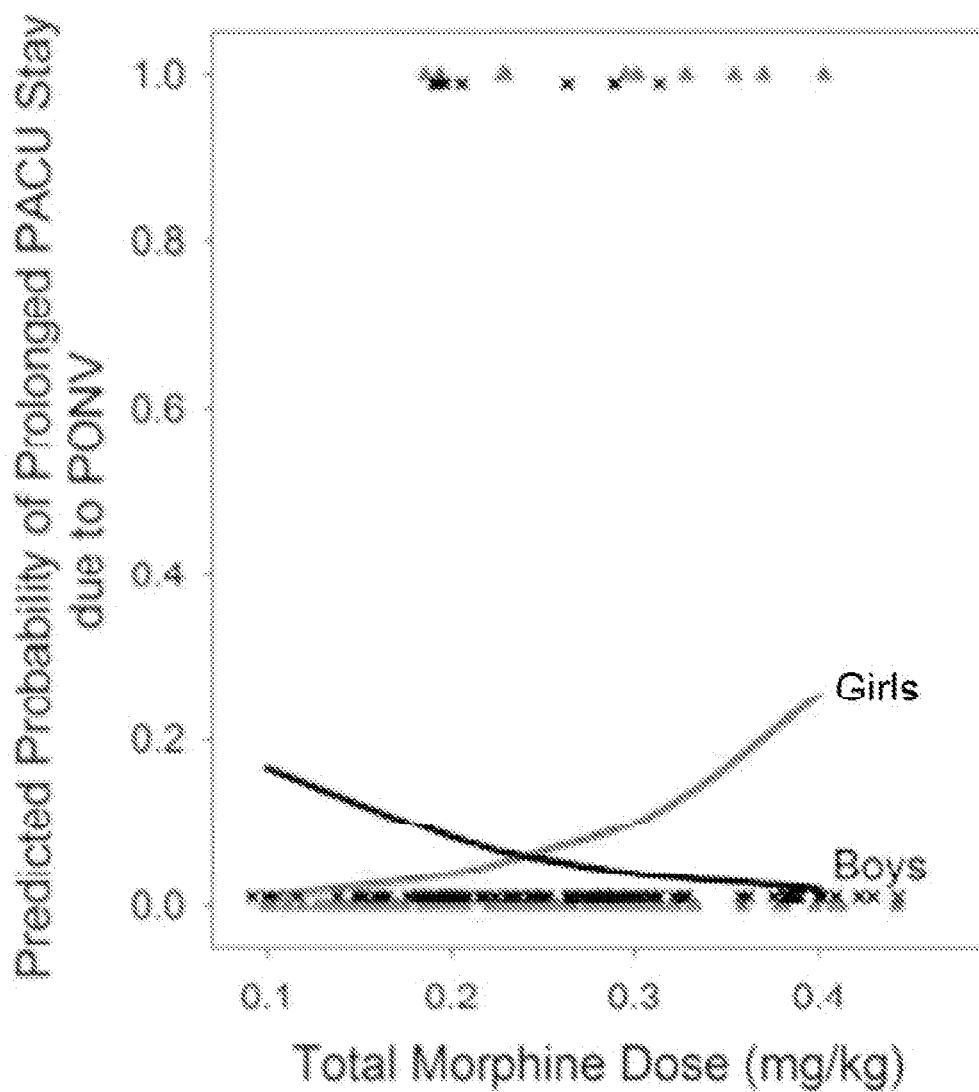

The univariate analyses were supported by multivariate models which formally tested for a morphine effect by sex using total morphine as a continuous variable. Significant sex-specific morphine effect was detected in PONV (p=0.001) and prolonged PACU stay due to PONV (p=0.010). In girls, probabilities of having these adverse effects increased with the total morphine dose, while in males, no significant changes were detected in the probabilities of having adverse effects with the increase of total morphine dose (FIGS. 12A and 12B).

Data shown in Table 12 indicated that in girls, most side effects occurred when total morphine exceeded 0.3 mg/kg. The threshold morphine effect was tested using multivariate models. The probability of side effects did not differ between the two lower morphine groups. However, when morphine exceeded 0.3 mg/kg, the probability of all opioid adverse effects except for pruritus increased significantly (p<0.05).

Figure 13A:
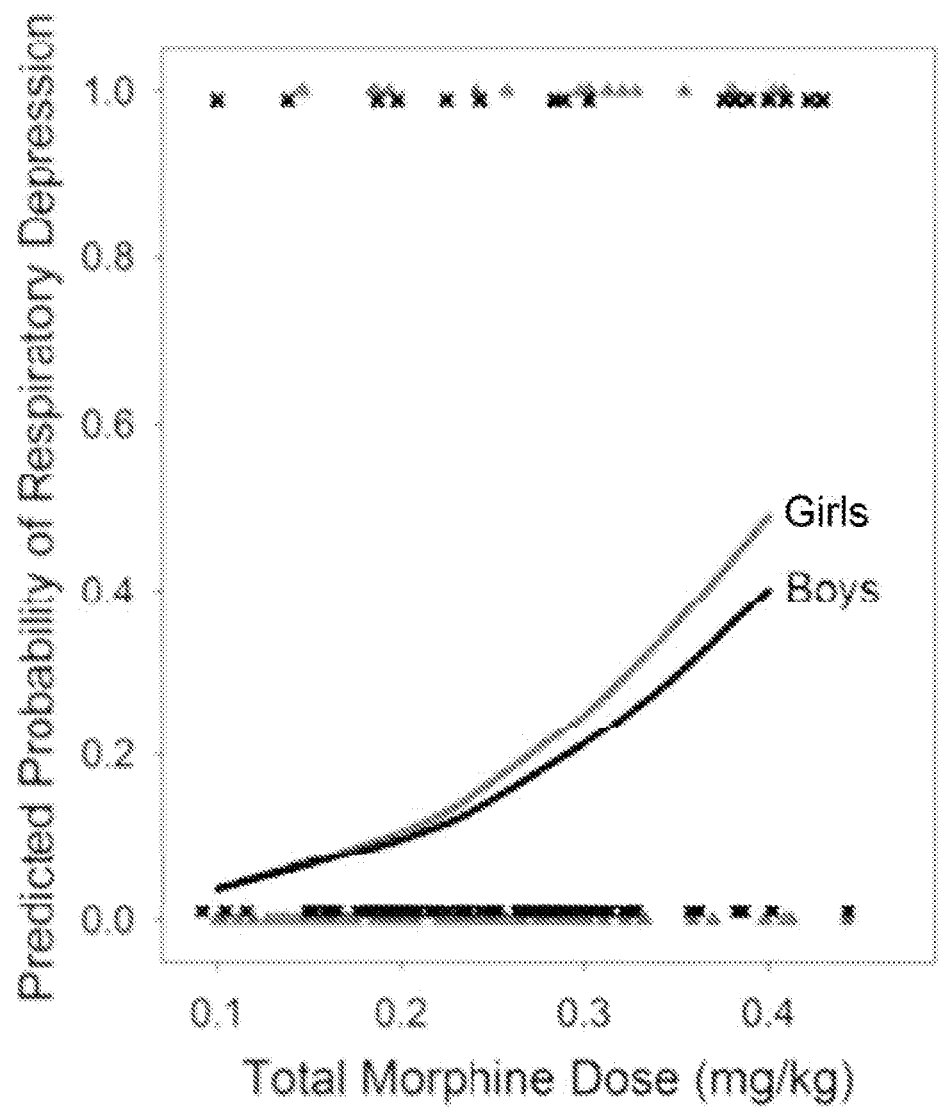
FIG. 13A-13B. Sex-specific differences in morphine-related respiratory depression (RD) in PACU.
A: Sex-specific differences in morphine-related RD in PACU. Total morphine dose is plotted in the X-axis and probability of morphine related Respiratory Depression is plotted in the Y-axis for boys and girls. Overall incidences of opioid-related Respiratory Depression in the PACU were relatively higher in girls compared with boys as the total morphine dose increased. B: Sex-specific differences in morphine-related RD resulting in prolonged stays in PACU. Total morphine dose is plotted in the X-axis and the probabilities of prolonged PACU stay due to RD are plotted in the Y-axis for boys and girls. The probability of PONV leading to prolonged PACU stay was relatively higher in girls compared with boys as the total morphine dose increased.
Figure 13B:
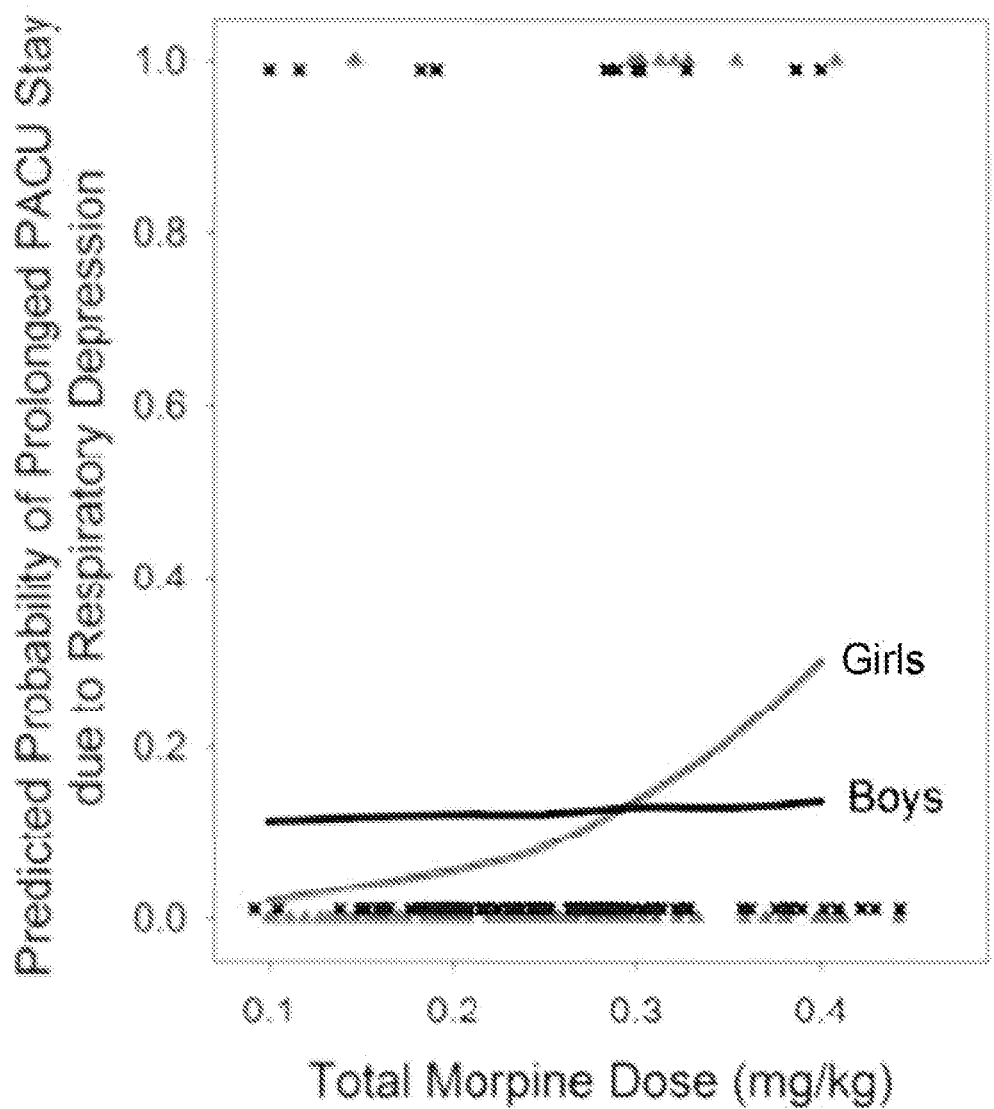

In girls, the probabilities of having respiratory depression increased with increase in total morphine dose (p=0.001) (FIGS. 13A and 13B). In boys, no significant changes were detected in the probabilities of having RD with the increase of total morphine dose (p=0.079, Table 12). In younger girls (<8 years and 8-13 years), a statistically significant association was detected between RD and higher total morphine dose (≥0.3 mg/kg) (Table 13).

Figure 14:
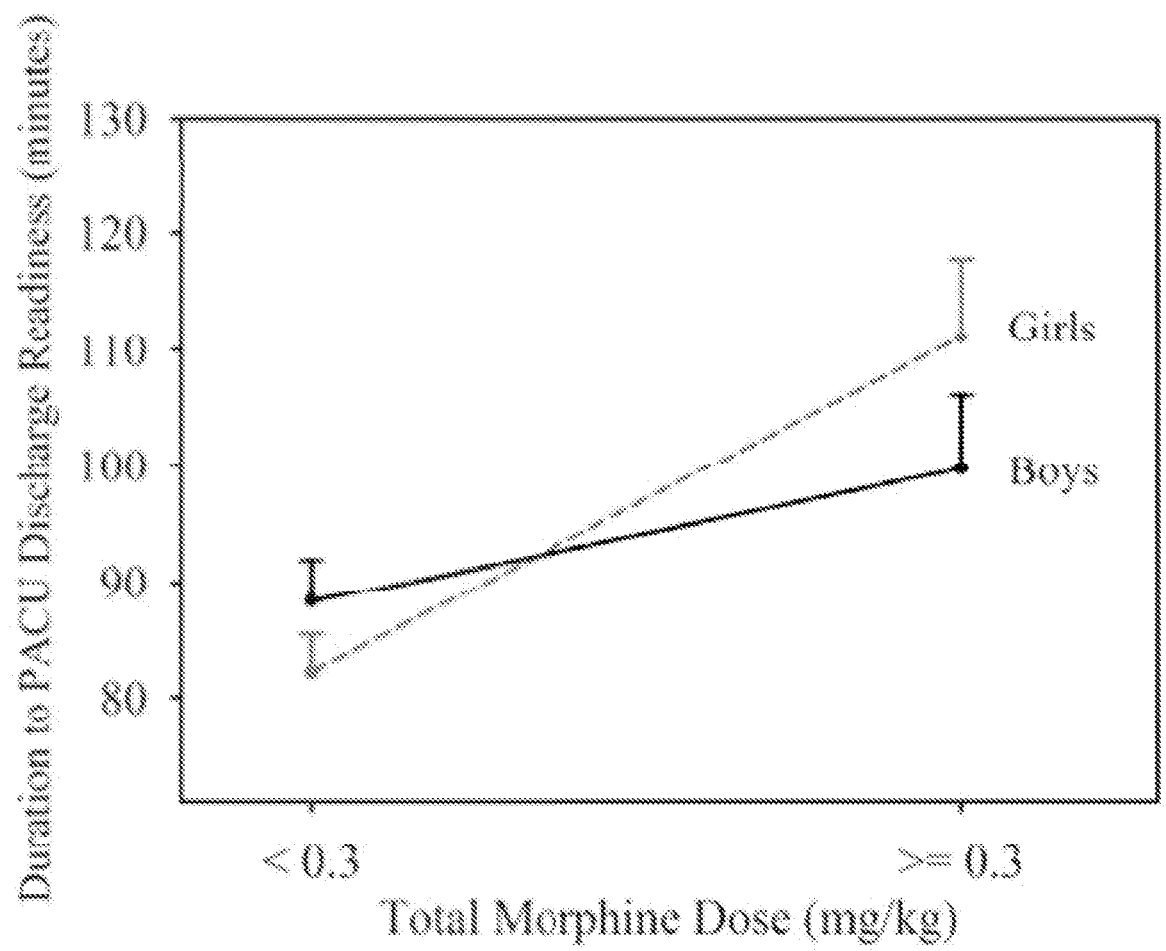
FIG. 14. Sex-specific differences in duration of stays in PACU between low (<0.3 mg/kg) and high (≥0.3 mg/kg) total morphine doses. White girls who received ≥0.3 mg/kg of total morphine stayed longer in PACU/(111.1±6.6 minutes) than that of girls who received <0.3 mg/kg of total morphine (82.2±3.3 minutes). White boys who received ≥0.3 mg·kg−1 of total morphine stayed in PACU for 99.7±6.4 minutes, while boys who received <0.3 mg·kg−1 of morphine stayed in PACU for 88.3±3.6 minutes. Though the differences in durations in PACU stay is clinically significant with about 30 minutes of longer stay in white girls between low and high total morphine doses, it did not reach statistical significance (p=0.09) after adjusting for age, weight, history of OSA. Even though the prolonged PACU stay in girls with high dose does not differ from that in boys with statistical significance (p=0.09), in the analysis stratified by sex, girls with high dose had longer PACU stay than girls with low dose (p=0.0002). But in boys, the difference is not statistically significant (p=0.11).

White girls who received ≥0.3 mg/kg of total morphine stayed longer in the PACU (111±6.6 minutes) than did girls who received <0.3 mg/kg of total morphine (82.2±3.3 minutes) (FIG. 14). White boys who received ≥0.3 mg/kg of total morphine stayed in the PACU for 99.7±6.4 minutes, while boys who received <0.3 mg/kg of morphine stayed in the PACU for 88.3±3.6 minutes (FIG. 13). Though the differences in durations in PACU discharge readiness did not reach statistical significance (p=0.09) after adjusting for age, weight, history of OSA, about 30 minutes of longer stay in white girls who received higher total morphine doses compared to lower doses, is clinically and economically significant following outpatient tonsillectomy. Even though the prolonged PACU stay in girls with high dose does not differ from that in boys with statistical significance (p=0.09), in the analysis stratified by sex, girls with high dose had longer PACU stays than girls with low dose (p=0.0002); in boys, the difference is not statistically significant (p=0.11) (FIG. 14).

There was no evidence of sex-specific morphine effects on analgesic outcomes using either the univariate or multivariate modeling (Table 13). There was no differential response to morphine with respect to analgesic effectiveness by sex.

In summary, in girls, significant association of total morphine dose was detected with PONV, RD, prolonged PACU due to PONV and RD. To test whether this association is influenced by age (i.e. hormonal effect in post-pubertal girls), girls who were less than 8 years, 8 to 13 years, and greater than 13 years were compared (Table 13). Younger girls (<8 years and 8-13 years) showed associations with RD, PONV, and prolonged PACU stays. However, when the age effect alone was tested in multivariate models, there was no statistically significant age differentiation detected possibly due to small sample size (data not shown).

This study demonstrates that while having similar analgesia, white girls were more sensitive to opioid adverse effects than boys as total morphine dose increased. White girls have differential response to higher total morphine doses leading to an unequal burden of higher incidences of opioid-related adverse effects and prolonged hospital stays after outpatient surgery compared to boys. Specifically, increasing doses of morphine in girls was associated with increased RD, PONV and prolonged stay in the recovery room due to opioid-related respiratory depression and PONV compared to boys. When not stratified by total morphine to low, medium and high doses, the safety and analgesic outcomes with the perioperative use of morphine in children did not differ by sex. These findings were not associated with age, BMI and surgical technique. These findings have significant clinical and economic impacts as girls are likely to have more opioid related RD and PONV with higher doses of opioids, leading to longer hospital stays as compared to boys.

Increasing morphine doses were found to result in increased side effects in girls but not boys. Specifically, girls who received the highest morphine dose category (0.3 mg/kg) had significantly more RD, PONV, prolonged PACU stay due to RD, and prolonged PACU stay due to PONV compared to those not in the high category. However, morphine dose was not associated with side effects in boys. Importantly, these effects were not related to OSA despite a relatively higher incidence of OSA in girls in this cohort. In the adult population, the literature supports that compared to men, women experience higher rates of opioid-related adverse effects, including respiratory depression (Fillingim R. et al., *J Pain*, 6:116-24 (2005); Zacny J. *Drug Alcohol Depend.*, 63:23-8 (2001); Zun L. et al., *Am. J. Emerg. Med.*, 20:151-4 (2002); Cepeda M. et al., *Clin. Pharmacol. Ther.*, 74:102-12 (2003); Franconi F. et al., *Pharmacol. Res.*, 55:81-95 (2007)). A few adult studies that looked at sex differences with morphine-induced respiratory depression (Sarton E. et al., *Anesthesiology*, 93:1245-54 (2000); Sarton E. et al., *Anesthesiology*, 90:1329-38 (1999)) showed that as compared to men, women are at higher risk of developing respiratory depression. However, very little data exist examining the effects of sex on opioid-related adverse effects in children.

In the extended post-discharge follow-up of the study cohort, it has been observed that girls with functional CYP2D6 phenotypes had significantly higher incidence of adverse effects at home with oral codeine (morphine prodrug) in the first 2-3 postoperative days similar and consistent to higher intravenous morphine dose related adverse effects among girls in PACU before discharge (Prows C. et al., *The Laryngoscope*, DOI: 10<dot>1002<slash>lary<dot>24454 (2013)). These consistent findings of higher incidences of adverse effects with intravenous morphine and oral codeine among girls in the hospital and home setting besides confirming the findings show the extended and unequal clinical and potentially economic impacts of opioids on girls. Sex-related differences in respiratory depression are shown to be secondary to effects mediated by the peripheral chemoreflex loop as opposed to a centrally-mediated effect (Sarton E. et al., *Anesthesiology*, 93:1245-54 (2000)).

This study did not find any association between sex, morphine dose and analgesia. A differential association of pain by pubertal age categories in girls was also not found. This is in contrast to some human adult studies which suggest that women experience better pain control with opioids (Campesi I. et al., *Handb. Exp. Pharmacol.* 265-78 (2012)). The entire pain experience may have different perception based upon sex (Toomey M. *AANA J.*, 76:355-9 (2008)). In addition, a significant difference in pharmacokinetics (approximately 40%) exists between men and women and it is attributed to a lower total body water as well as higher fat percentage to muscle in women than men (Anderson G. *J. Womens Health (Larchmt)*, 14:19-29 (2005)). Different expression of enzymes necessary for drug metabolism may also be responsible for these differences (Anderson G. *J. Womens Health (Larchmt)*, 14:19-29 (2005); Schwartz J. *Clin. Pharmacol. Ther.*, 82:87-96 (2007); Franconi F. et al., *Curr. Pharm. Des.*, 17:1095-107 (2011)). The pharmacokinetics of morphine including morphine clearance have been reported previously (Sadhasivam S. et al., *J. Opioid Manag.*, 8:217-26 (2012)). Sex was included as a covariate for morphine clearance but was not found to be a major predictor of variability in morphine pharmacokinetics in children (Sadhasivam S. et al., *J. Opioid Manag.*, 8:217-26 (2012)).

In this study, opioid-related adverse effects tended to occur more often in girls when high total morphine dose (>0.3 mg/kg) was administered; while in boys such linear trends in increasing opioid adverse effects with total morphine doses were not observed (Table 12). It was hypothesized that hormonal differences between boys and girls could potentially explain the sex differences in opioid adverse effects. To potentially explain the mechanism behind the sex differences in opioid adverse effects, common pubertal age in girls was used as surrogate for different hormonal levels associated with puberty, and 3 age categories for girls were analyzed: <8 years (pre-puberty), 8-13 years (pubertal age); >13 years (post-puberty). In girls, significant association of total morphine dose was detected with PONV, RD and prolonged PACU due to PONV and RD; younger girls had significantly more RD and PONV with higher doses of morphine (Table 14). Interestingly, age or OSA incidence (higher frequencies in younger girls and boys) were not associated with girls' sensitivity to morphine dose, when the age and OSA effects were tested in multivariate models, probably due to small number of girls in each age and total morphine dose categories. Since high incidences of opioid adverse effects with the high morphine dose (0.3 mg/kg) are apparent across all three age categories (especially in younger girls), these data are not supportive of hormonally-mediated differences in girls. However, as Tanner staging was not performed, it is possible that this age categorization was not a good metric for puberty stage.

It is important to note that these analyses were restricted to a single self-reported white population. As previous studies have demonstrated that there are differences in the risk of side effects by race (Sadhasivam S. et al., *Pediatrics*, 129:832-8 (2012)), it was important to analyze by race. Although race per se was not the focus of the study, there was more than 95% correlation between self-reported race and ancestry informative markers in our study. Self-report of race is easier to use as it is readily available to clinicians than genetic markers of ancestral origin. Due to the relatively small number of minority children available for meaningful analysis, the results were focused on white children. It is unclear whether or not these differences would still be seen in non-white populations. Based on these data, white girls can benefit from more aggressive PONV and RD prevention strategies for white girls.

In conclusion, sex differences for dose-related opioid adverse effect risks exist in white children. White girls have higher risk of having opioid-related respiratory depression and PONV and prolonged stays in PACU due to opioid adverse effects with higher doses of morphine than boys undergoing surgery. This difference was not explained by pubertal age or history suggestive of OSA. When treating children, one should keep in mind that while experiencing similar analgesia to boys, white girls are relatively more sensitive to higher doses of opioids, have higher opioid-related adverse events and stay longer in PACU; this knowledge might help prevent unfavorable clinical and economic perioperative outcomes in children.

Example 7

Opioid-Induced Respiratory Depression: ABCB1 Transporter Pharmacogenomics

Morphine's effects are mediated by mu opioid receptors located in the brainstem, especially the medulla, which contains abundant mu receptors responsible for analgesia as well as the ventilatory responsiveness to hypercapnia (Zhang, Z., et al., *Anesthesiology*, 107:288-297 (2007); Pattinson, K. *Br. J. Anaesth.*, 100:747-758 (2008)). In addition, opioids have profound effects on the cortical centers that control breathing, which potentiates their actions in the brainstem (Pattinson, K. et al., *J. Neurosci.*, 29:8177-8186 (2009)). Thus, variability in morphine transport into the brain may help explain inter-individual response to morphine. The concentration of morphine in brain is influenced by a P-glycoprotein transporter, ABCB1 at the blood brain barrier. A polymorphism of ABCB1, c.3435C>T, has been linked with morphine's blood brain barrier transport activity in adults and the homozygous TT genotype was associated with higher maximum CSF concentrations of morphine than other genotypes (Meineke, I. et al., *British Journal of Clinical Pharmacology*, 54:592-603 (2002)). Previously, the same ABCB1 polymorphism, c.3435C>T has been associated with increased respiratory depression in Korean adults receiving another opioid, fentanyl (Park, H. et al., *Clin. Pharmacol. Ther.*, 81:539-546 (2007)). However, whether ABCB1 variants are associated with morphine-induced respiratory depression in children is not known.

This study hypothesized that genetic variations in ABCB1 significantly influence the safety and clinical efficacy of morphine in children. This study aimed to determine specific associations between common ABCB1 genetic variants and intravenous morphine induced postoperative respiratory depression in a large homogenous population of American children undergoing tonsillectomy, using clinical measures of respiratory depression in addition to post-operative analgesia. This example was later published as Sadhasivam et al., *The Pharmacogenomics Journal* (2014) 1-8, the contents of which are hereby incorporated by reference.

Study Design, Participants, and Procedures

Figure 15:
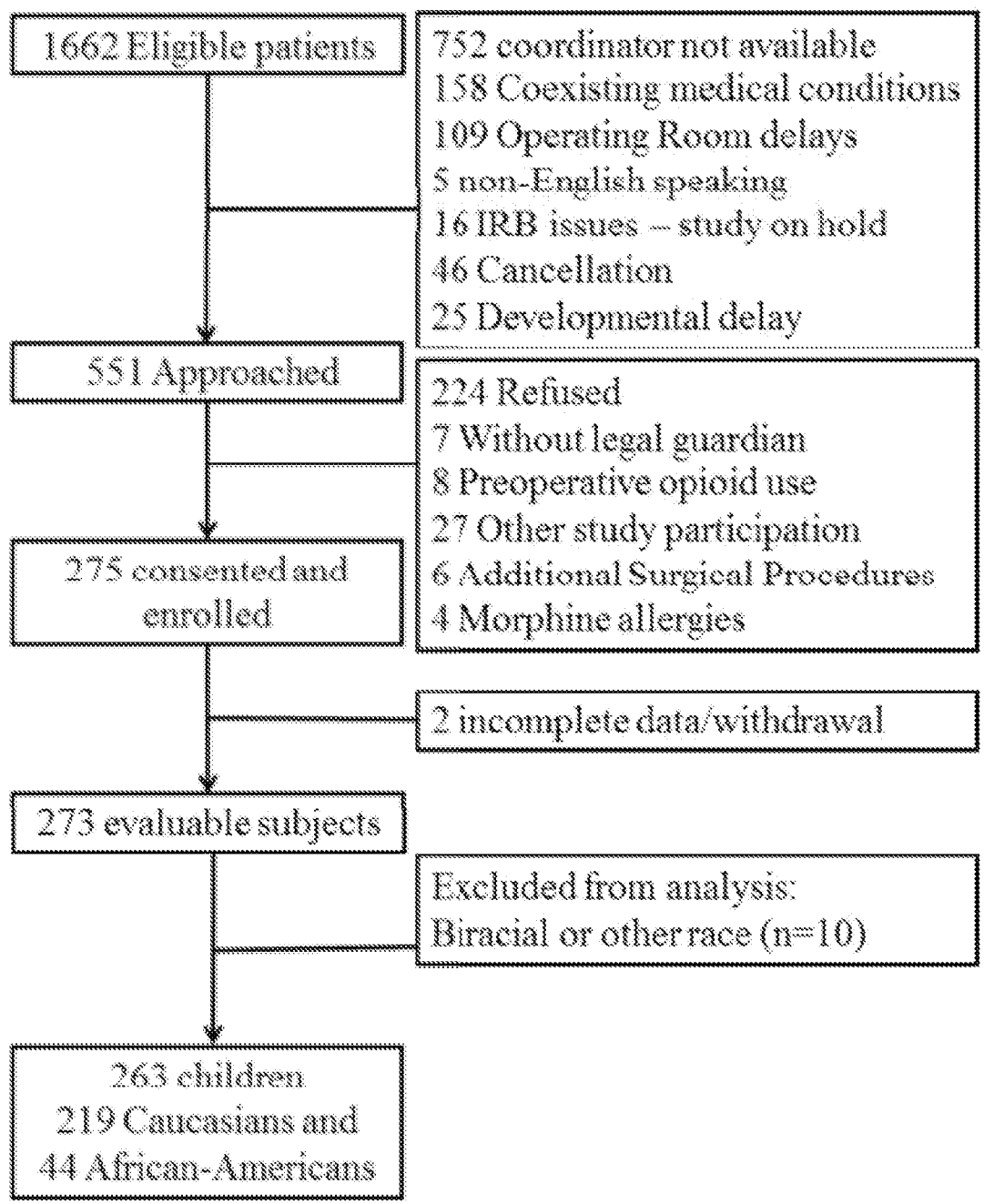
FIG. 15. The consort diagram illustrates the flow of study participants through this clinical trial. Eligible participants, reasons for exclusions, enrolled and analyzed patients are reported. IRB=institutional review board.

A prospective clinical observational study in 273 children undergoing tonsillectomy was conducted with standard perioperative anesthetic and surgical practices as well as standard postoperative nursing care. The study was approved by the institutional review board at Cincinnati Children's Hospital Medical Center and written informed consents and assents (from children >11 years) were obtained from all parents and participating children. Though children of all races were enrolled in this study, given the demographics of patients for tonsillectomy at our hospital, the vast majority of children were white (FIG. 15).

Children 6-15 years undergoing elective outpatient tonsillectomy were eligible for the study and recruited on the day of surgery. Race was self-reported by either the parent or child; self-report is well accepted for identifying race (Boehmer, U. et al., *American Journal of Public Health*, 92:1471-1472 (2002); Lalovic, B. et al., *Drug Metab. Dispos.*, 32:447-454 (2004)). Sample inclusion criteria were children designated to have an American Society of Anesthesiologists (ASA) physical status 1 or 2 scheduled for tonsillectomy because of recurrent tonsillitis, adenotonsillar hypertrophy, or OSA. Clinical criteria for OSA designation included sleep disordered breathing with a history of snoring and either sleep pauses lasting more than 10 seconds or daytime drowsiness. Children were excluded from the study if they or their parents were non-English speaking. Children who were allergic to morphine or who had developmental delay, liver or renal disease, or preoperative pain requiring opioid analgesics (e.g. chronic tonsillitis) were excluded.

All participants received standard perioperative care. Anesthesia was induced using sevoflurane followed by a propofol (2 mg/kg) bolus to facilitate endotracheal intubation. Anesthesia was maintained with sevoflurane without the use of neuromuscular blockade. Patients received morphine prior to surgical incision. Children with OSA history received 0.1 mg/kg morphine while those without OSA diagnosis received 0.2 mg/kg. If there were any signs suggestive of pain (clinically significant increase in heart rate and blood pressure) following surgical incision and cauterization, the clinical anesthesia team provided additional morphine at 0.05 mg/kg increments intraoperatively as necessary. All children receive prophylactic ondansetron (0.1 mg/kg) and dexamethasone (0.1 mg/kg) intraoperatively. Significant postoperative pain measured with FLACC pain score (Merkel, S. et al., *Pediatr. Nurs.*, 23:293-297 (1997)) of ≥4/10 was managed in the PACU with rescue doses of morphine (0.05 mg/kg increments).

Duration of PACU stay (time to achieve PACU discharge readiness) was defined as the duration in PACU before achieving the following discharge criteria. Level of consciousness: easily arousable or awake, airway: patent with adequate air exchange, core body temperature: ≥36.3 degrees Celsius, acceptable pain level (pain score <4), hemodynamically stable, no significant opioid related adverse effects such as PONV and respiratory depression, and surgical site without any bleeding or complications. This is discharge readiness time is different from actual PACU discharge time as delays due to social reasons (e.g. waiting for car rides) were not included.

Out of 273 children recruited, 219 were white and 44 were black children. Because of different allelic frequencies of ABCB1 SNPs, and smaller number children from other races, the analysis was focused on white and black children. Children of other races and biracial children were not analyzed (FIG. 15). Participants were primarily white with slightly more females than males. Compared to white children, black children were slightly heavier and had higher OSA frequencies (Table 14).

TABLE 15

Characteristics of participants.

| | Whites (N-219) | Blacks (N = 44) |
|---|---|---|
| Age (year) (median (IQR)) | 8.4 (7.1-11.0) | 8.8 (7.2-10.8) |
| Weight (kg) (median (IQR)) | 34.2 (25.8-46.5) | 35.6 (27.2-54.0) |
| BMI z scores | 0.8 (−0.2-1.6) | 1.2 (0.1-2.0) |
| Intra-operative morphine requirement (mg/kg) (median (IQR)) | 0.19 (0.17-0.21) | 0.20 (0.16-0.20) |
| Total morphine requirement (mg/kg) (median (IQR)) | 0.24 (0.19-0.29) | 0.29 (0.21-0.35) |
| Sex (N, %) Male | 105 (48%) | 19 (43%) |
| OSA (N, %) Yes | 95 (43%) | 30 (68%) |

Age, weight, BMI z score, intra-operative and total morphine requirements are shown as median and inter-quartile range (IQR), sex and OSA are shown as frequencies and proportions.
BMI z scores were calculated using CDC growth charts.

Outcomes

Metrics for analgesic effectiveness and opioid-related adverse effects were recorded for each participant. For the metrics for opioid-related adverse effects, this study focused on two clinically and economically important outcomes: clinical RD and prolonged PACU stay (>90 minutes) secondary to respiratory depression assessed consistently by the research coordinator. In this study, RD was defined as a respiratory rate <10 breaths per minute and oxygen desaturation <92% persisting for more than 1 minute and requiring supplemental oxygen to maintain SpO2 >92% in the absence of clinically obvious upper airway obstruction.

Metrics for analgesic effectiveness included maximum postoperative pain scores, intravenous analgesic interventions in PACU (yes/no) and post-operative morphine doses (mg/kg) in patients requiring analgesic interventions. The maximum postoperative pain score for each child was generated from postoperative pain scores assessed in PACU at multiple time points using a 0 to 10 FLACC pain scale (Merkel, S. et al., *Pediatr. Nurs.*, 23:293-297 (1997)).

Genotypes

Blood was collected from each participant in the operating room under anesthesia and the DNA was isolated the same day and stored at −20 degree Celsius. Batched genotyping was performed after clinical data was entered on all study participants. The TaqMan allelic discrimination system assays and Genotyper Softerware Version 1.0.1 (Life Technologies, Applied Biosystems, Forest City, Calif.) were used to analyse and report the following ABCB1 polymorphisms: rs1045642, rs2032582, rs1128503, rs2229109, and rs9282564.

Statistical Analysis

Prior to analysis, data qualities were examined. For the ABCB1 variants, allelic and genotype frequencies were assessed in white and black patients separately, and Hardy Weinberg equilibrium (HWE) was tested. To analyze binary outcomes (RD, prolonged PACU secondary to RD and analgesic intervention need), logistic regression was performed. For postoperative morphine dose, linear regression was used because dose was normally distributed. Maximum FLACC scores exhibited a zero-inflated negative binomial distribution with 26% of the patients experiencing no pain. Thus, maximum FLACC scores were analyzed using a zero-inflated negative binomial model to appropriately capture the distribution of this variable. Prior to evaluation of ABCB1 variants, the effects of covariates (age, sex, BMI z scores, OSA, intra-operative morphine (for analgesic outcomes) and total morphine (for adverse effect outcomes)) were evaluated. To select the best fitting model, log likelihood, Akaike and Bayesian Information criterion were compared, and residuals were examined. Covariates that significantly improved model fitting (p<0.05) were retained for subsequent genetic analyses. To assess the single SNP association with the outcomes, additive models were used, in which the genotypes were recoded and tested as continuous variables. For the four bi-allelic SNPs, genotypes were recoded to 0, 1 and 2 according to the number of minor alleles. For rs2032582, GG genotype was recoded as 0; GA and GT genotypes were combined and recoded as 1, and TT and TA genotypes as 2. Statistical modeling was conducted with white and black patients separately and combined. When races were combined, the effects of race and race*SNP interaction were tested.

In this study, the association of 5 SNPs of ABCB1 with two primary side effect outcomes and three secondary analgesic outcomes was tested. The mean correlation coefficient among the 5 SNPs was 0.40. The Spearman correlation coefficients between the primary outcomes and among the secondary outcomes were 0.49 and 0.74, respectively. To correct the p value for multiple testing, the correlated nature of the outcomes and the SNPs was accounted for. A correlation-adjusted Bonferroni correction (http<colon slash slash>www<dot>quantitativeskills<dot>com<slash>sisa) yielded a significance threshold of 0.013 for the tests on primary side effect outcomes, and a threshold of 0.014 for the tests on the secondary outcomes. Associations reaching the threshold of 0.05 as nominally associated are also reported. Statistical analyses were performed using Statistical Analysis Software (SAS), version 9.3 and JMP Genomics, version 6.0 (SAS Institute Inc., Cary, N.C.).

Permutation test: In genetic association studies, low allele frequencies (<0.1) can lead to small numbers of individuals driving an association. Thus, for variants identified to be significantly associated with minor allele frequencies less than 0.1, permutation testing was performed using both races combined. Using R programming language, one thousand replicates of data were generated by randomly shuffling the genotypes while keeping the association between covariates and outcomes unchanged. Each replicate was then analyzed using the same methods with the same covariates adjusted as described above.

Correlation between self-identified race and genetic ancestry—Sensitivity analysis: To assess whether self-reported white and black races match well to genetic ancestry, principal component analysis was performed with 218 ancestry informative markers (AIMs) using Golden Helix software. 1397 HapMap subjects were used as reference populations for analysis.

Power analysis: Prior to this study analysis, statistical power to detect a genetic effect was estimated using Quanto. The minor allele frequency (MAF) was varied from 0.03 to 0.5 to capture the variability of our variants and a was held to 0.013 to account for multiple testing. For the primary outcome adverse effect outcome, respiratory depression leading to respiratory depression (frequency 11%), 80% power was used to detect an odds ratio equaling 2 6 (MAF≥0 3), 2 8 (MAF=0 2), 3 6 (MAF=0 10), and 7 3 (MAF=0 03) using our full sample of 263 children. For the primary analgesia outcome, postoperative morphine requirement, only individuals who needed analgesia intervention were included (n=162). An 80% power was used to detect an effect that accounts for as little as 9% of the variation (beta range 0 37-1 09 standard deviation units).

Results

ABCB1 SNPs and Allelic Frequencies.

Among the five SNPs examined, one is tri-allelic (rs2032582); one is of low frequency in both whites and blacks (rs2229109); one (rs1045642) is common with major and minor allele flipped in whites and blacks. All SNPs were in HWE (Stern, C. Science, 97:137-138 (1943)) and showed high linkage disequilibrium (Tables 15 and 16).

TABLE 16

ABCB1 polymorphisms, allele frequency, and HWE test.

| SNP | | | | Whites | | Blacks | |
|---|---|---|---|---|---|---|---|
| Alias | | Function | Allele | Frequency | P (HWE) | Frequency | P (HWE) |
| rs1045642 | 3435C > T | Synonymous variant | T | 0.548 | | 0.227 | |
| | | | C | 0.452 | 0.25 | 0.773 | 0.53 |
| | | | A | 0.018 | | 0.011 | |
| | 2677T > A (S893T), | Non Synonymous variant | | | | | |
| rs2032582 | 2667 > G (S893A) | Synonymous variant | T | 0.441 | 0.26 | 0.091 | 0.9 |
| | | | G | 0.541 | | 0.898 | |
| rs1128503 | 1236T > C (G412G) | Synonymous variant | T | 0.448 | 0.39 | 0.25 | 0.55 |
| | | | C | 0.552 | | 0.75 | |
| | | | A | 0.032 | 0.63 | 0.011 | 0.94 |
| rs2229109 | 1692G > A (S400N) | Non Synomymous Variant | | | | | |
| rs9282564 | 554A > G (N21D) | Non Synonymous Variant | C | 0.968 | | 0.989 | |
| | | | G | 0.114 | 0.57 | 0.034 | 0.81 |
| | | | A | 0.886 | | 0.966 | |

Allele frequency and Hardy-Weinberg equilibrium (HWE) test for five SNPs of ATP-binding cassette B1 (ABCB1).
Analyses were stratified by race (whites and blacks).

TABLE 17

Linkage between ABCB1 SNPs in white and black children (D'/R$^2$).

| | | rs1045642 | rs2032582 | rs1128503 | rs2229109 | rs9282564 |
|---|---|---|---|---|---|---|
| Whites | rs1045642 | | | | | |
| | rs2032582 | 0.935/0.572 | | | | |
| | rs1128503 | 0.832/0.463 | 0.923/0.827 | | | |
| | rs2229109 | 1/0.040 | 1/0.090 | 1/0.027 | | |
| | rs9282564 | 0.8425/0.075 | 0.949/0.147 | 0.9475/0.143 | 1/0.004 | |
| Blacks | rs1045642 | | | | | |
| | rs2032582 | 1/0.340 | | | | |
| | rs1128503 | 0.6338/0.354 | 1/0.300 | | | |
| | rs2229109 | 1/0.003 | 1/0.001 | 1/0.004 | | |
| | rs9282564 | 1/0.12 | 1/0.353 | 1/0.106 | 1/0.000 | |

Linkage between five SNPs of ATP binding cassette B1 (ABCB1).
Analyses were stratified by race (whites and blacks) and presented as D$^1$ and R$^2$

TABLE 18

RD and prolonged PACU stay due to RD by genotypes.

| | | Whites | | | | | Blacks | | | | |
|---|---|---|---|---|---|---|---|---|---|---|---|
| SNP | | N | RD % | P | Prolonged PACU due to RD % | P | N | RD % | P | Prolonged PACU due to RD % | P |
| rs1045642 | TT | 70 | 16 | 0.87 | 10 | 0.12 | 3 | 33 | 0.44 | 33 | 0.25 |
| | TC | 100 | 19 | | 15 | | 14 | 43 | | 21 | |
| | CC | 49 | 16 | | 4 | | 27 | 22 | | 7 | |
| rs2032582 | TT | 46 | 11 | 0.53 | 9 | 0.73 | 0 | — | 0.35 | — | 0.40 |
| | TA | 1 | 0 | | 0 | | 0 | — | | — | |
| | GA | 7 | 29 | | 0 | | 1 | 0 | | 0 | |
| | GT | 100 | 18 | | 14 | | 8 | 50 | | 25 | |
| | GG | 65 | 20 | | 9 | | 35 | 26 | | 11 | |
| rs1128503 | TT | 47 | 11 | 0.24 | 11 | 0.69 | 2 | 50 | 0.30 | 50 | 0.22 |
| | TC | 102 | 17 | | 13 | | 18 | 39 | | 17 | |
| | CC | 70 | 23 | | 9 | | 24 | 21 | | 8 | |
| rs2229109 | CA | 14 | 36 | 0.07 | 14 | 0.66 | 1 | 0 | 1.00 | 0 | 1.00 |
| | CC | 205 | 16 | | 11 | | 43 | 30 | | 14 | |

TABLE 18-continued

RD and prolonged PACU stay due to RD by genotypes.

| SNP | | N | RD % | P | Prolonged PACU due to RD % | P | N | RD % | P | Prolonged PACU due to RD % | P |
|---|---|---|---|---|---|---|---|---|---|---|---|
| | | | | | Whites | | | | | Blacks | |
| rs9282564 | GG | 2 | 100 | 0.04 | 100 | <0.01 | 0 | — | 0.20 | — | 0.04 |
| | GA | 46 | 17 | | 20 | | 3 | 67 | | 67 | |
| | AA | 171 | 16 | | 8 | | 41 | 27 | | 10 | |

Opioid-related RD and prolonged stay in recovery room due to RD. Frequencies and proportions are presented by genotypes and were tested using Fisher's exact tests.

TABLE 19

Postoperative analgesia measurements by ABCB1 genotypes.

| SNP | | Whites | | | | | | | | Blacks | | | | | |
|---|---|---|---|---|---|---|---|---|---|---|---|---|---|---|---|
| | | N | Maximum FLACC | P | Analges. % | P | Post-Operative morphine (mg/kg) | P | N | Maximum FLACC | P | Analges. % | P | Post-operative morphine (mg/kg) | P |
| rs10456542 | TT | 70 | 2 (1-5) | 0.29 | 57 | 0.42 | 0.10 ± 0.05 | 0.61 | 3 | 8 (3-8) | 0.89 | 100 | 1.00 | 0.12 ± 0.11 | 0.99 |
| | TC | 100 | 2 (0-4) | | 52 | | 0.09 ± 0.05 | | 14 | 7 (1-8) | | 86 | | 0.12 ± 0.05 | |
| | CC | 49 | 4 (0-6) | | 63 | | 0.09 ± 0.03 | | 27 | 5 (4-8) | | 89 | | 0.12 ± 0.07 | |
| Rs2032582 | TT | 46 | 1 (1-5) | 0.52 | 52 | 0.87 | 0.09 ± 0.04 | 0.14 | 0 | — | 0.75 | — | 0.32 | — | 0.80 |
| | TA | 1 | 8 (8-8) | | 100 | | 0.21± | | 0 | — | | — | | — | |
| | GA | 7 | 2 (1-5) | | 43 | | 0.09 ± 0.05 | | 1 | 4 (4-4) | | 100 | | 0.08± | |
| | GT | 100 | 2 (0-5) | | 57 | | 0.09 ± 0.05 | | 8 | 8 (2-9) | | 75 | | 0.11 ± 0.04 | |
| | GG | 65 | 4 (0-6) | | 58 | | 0.09 ± 0.04 | | 35 | 5 (3-8) | | 91 | | 0.12 ± 0.07 | |
| Rs1128503 | TT | 47 | 1 (0-5) | 0.40 | 53 | 0.92 | 0.08 ± 0.04 | 0.43 | 2 | 4 (0-8) | 0.81 | 100 | 1.00 | 0.08 ± 0.03 | 0.64 |
| | TC | 102 | 2 (0-5) | | 57 | | 0.10 ± 0.05 | | 18 | 6 (3-9) | | 89 | | 0.13 ± 0.05 | |
| | CC | 70 | 3 (0-5) | | 57 | | 0.09 ± 0.04 | | 24 | 5 (4-8) | | 88 | | 0.12 ± 0.08 | |
| Rs2229109 | CA | 14 | 2 (1-4) | 0.69 | 50 | 0.78 | 0.06 ± 0.02 | 0.06 | 1 | 8 (8-8) | 0.57 | 100 | 1.00 | 0.04± | 0.23 |
| | CC | 205 | 2 (0-5) | | 57 | | 0.09 ± 0.05 | | 43 | 5 (3-8) | | 88 | | 0.12 ± 0.06 | |
| Rs9282564 | GG | 2 | 7 (6-7) | 0.18 | 100 | 0.62 | 0.16 ± 0.07 | 0.13 | 0 | — | 0.05 | — | 1.00 | — | 0.52 |
| | GA | 46 | 2 (0-4) | | 54 | | 0.09 ± .05 | | 3 | 8 (8-10) | | 100 | | 0.10 ± 0.00 | |
| | AA | 171 | 2 (0-5) | | 56 | | 0.09 ± 0.04 | | 41 | 5 (3-8) | | 88 | | 0.12 ± 0.07 | |

Maximum FLACC scores are shown as median (IQR) and tested by exact Wilcoxon rank-sum tests; intervention needs are shown as frequencies and proportions and tested by Fisher's exact tests; post-operative morphine requirements are examined in patients who had at least one post-operative intervention. They are shown as mean ± SD and tested using ANOVA. Analges. % represents analgesic interventions %.

Figure 16A:
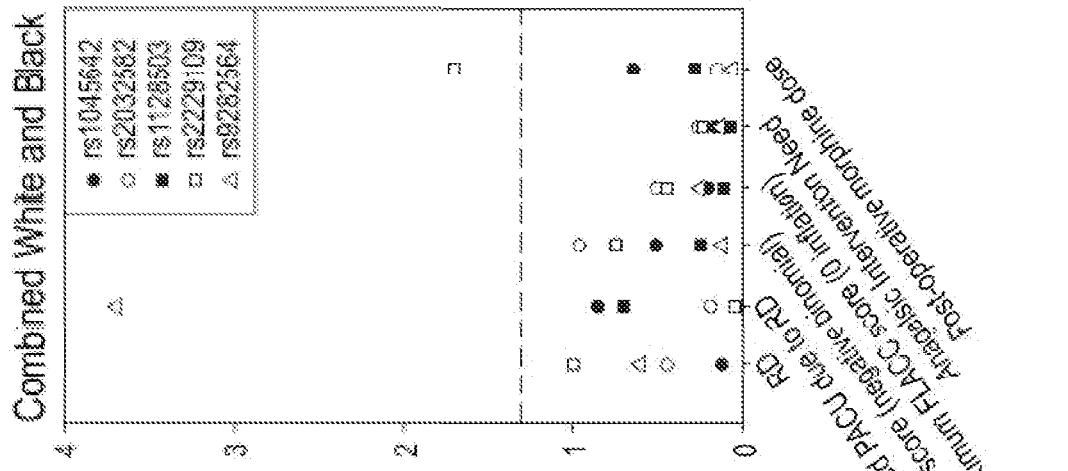
FIG. 16A-16C. Genetic association of five ABCB1 SNPs and clinical outcomes. The –log 10 (p values) of the single SNP association tested in additive models were plotted. The reference line shows the –log 10 (p value of 0.05) level. Tests were performed in whites (A), blacks (B), and with races combined (C). In both races, the ABCB1 SNP, rs9282564 consistently had significant association with prolonged PACU stay due to respiratory depression; and ABCB1 SNP, rs2229109 was associated with postoperative morphine requirement. RD=respiratory depression; PACU=Post-anesthesia care unit; FLACC=Face Leg Activity Cry and Consolability pain scale.
Figure 16B:
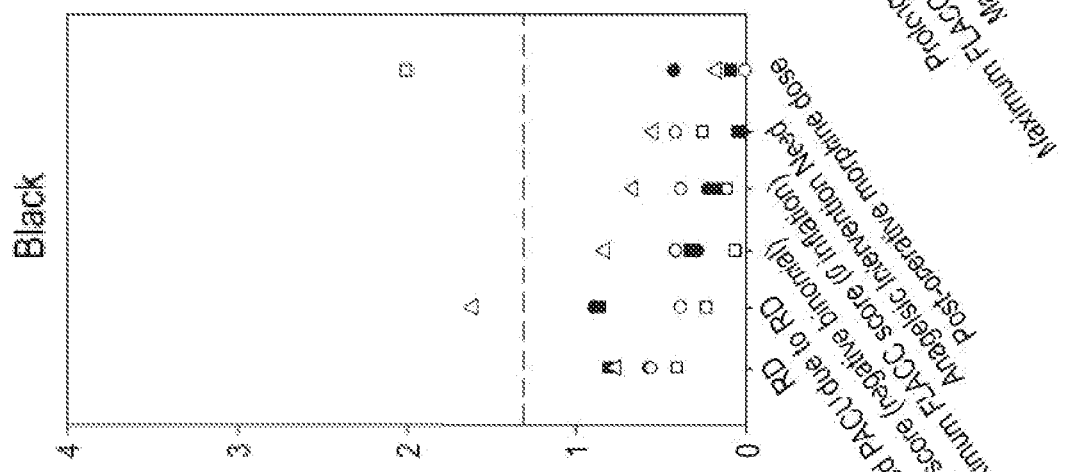
Figure 16C:
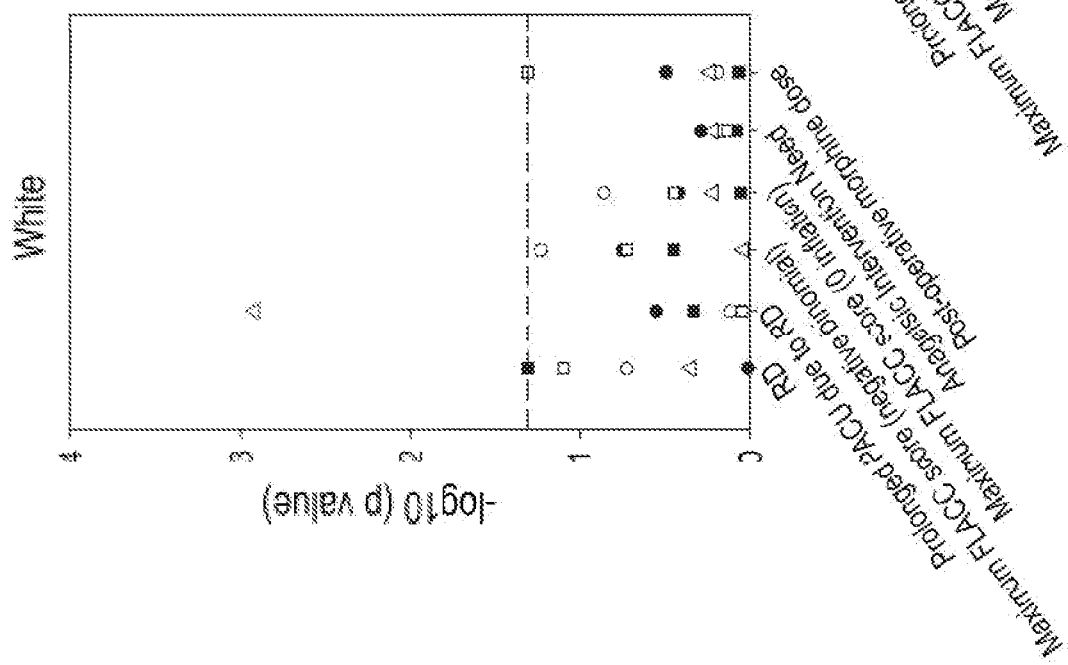
Figure 17:
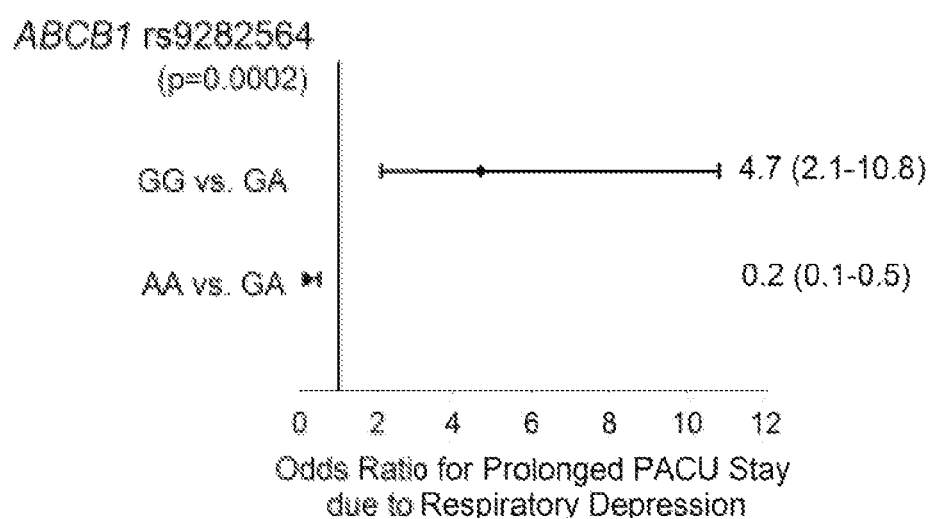
FIG. 17. ABCB1 genotype and risk of respiratory depression. Compared to children with GA genotype, children with GG genotype of rs9282564 had 4.7 fold higher odds of respiratory depression resulting in prolonged stay in PACU ((95% CI: 2.1-10.8, p=0.0002). Compared to children with GA genotype, children with AA genotype of rs9282564 had a lower [0.2 (0.1-0.5)] odds of respiratory depression resulting in prolonged stay in PACU. PACU=Post Anesthesia Care Unit FIG. 18. ABCB1 transporter structure and mapping of non-synonymous polymorphisms. Using sequence alignment, secondary structure and TM helix prediction (http<colon slash slash>sable<dot>cchmc<dot>org) and resolved structure of mouse ortholog, 3 non-synonymous SNPs are mapped to positions 21 (red site within the unresolved N-terminal fragment), 400 (blue side chain model shown in the vicinity of the first ATP binding site), and 893 (magenta site within the cytosolic extension of TM10). For the rest of the structure, yellow is used to indicate hydrophobic residues, whereas red, orange and brown charged and hydrophilic residues, respectively. The membrane is symbolically shown as a blue rectangle. Polyview-3D (http<colon slash slash>polyview<dot>cchmc<dot>org) was used to generate to the figure. Structure-based analysis of the effects of ABCB1 SNPs: Among ABCB1 SNPs analyzed, rs9282564, rs2229109, and rs2032582 are non-synonymous, and result in amino acid sequence changes at positions 21 (N vs. D), 400 (S vs. N), and 893 (S vs. A vs. T), respectively. All 3 affected residues are located within one of the cytosolic "arms" of the transporter, as indicated by red, magenta and blue sites. The first of these sites (residue 21) is located within a flexible N-terminus cytoplasmic segment, directly proceeding transmembrane helix TM1. This N-terminus domain is highly variable and contains multiple positively charged residues. While it could interact with the rest of the cytosolic part of the transporter, or with ABCB1 co-factors, structural data regarding such interactions, together with further sequencing will be necessary to gain insights into the functional role of this site. On the other hand, detailed analysis of structural context of the second variant (blue site) suggests that it could potentially play a direct role in regulation of the ABCB1 function. Position 400, while not conserved evolutionarily itself, is flanked by 2 strongly conserved aromatic residues forming FSY motif. These two residues make contact with another conserved site, involving residues 442-445 (RLYD). Together, these 2 solvent-exposed loops constitute a direct vicinity of (although they are not in direct contact with) the ATP binding site, which includes residues 427-434 (shown as green). As these loops are predicted to undergo conformational changes upon ATP hydrolysis, Asn400 allele could affect how these changes propagate through the overall structure and contribute to opening and closing of the transporter. The remaining 2 SNPs, i.e., rs1128503 and rs1045642, are synonymous. Interestingly, these 2 SNPs are in relatively strong linkage with each other, as well as non-synonymous rs2032582 (but not with the other 2 non-synonymous SNPs, rs9282564 and rs2229109). In the 1000 Genomes CEU cohort, r2 of 0.87 and 0.51 are observed between rs2032582 and these 2 non-synonymous SNPs. All of these SNPs could be effective markers of another polymorphism in linkage disequilibrium, e.g. affecting expression of ABCB1 protein. Further sequencing, structural and biochemical studies will be required to confirm the true functional marker.

ABCB1 and Respiratory Depression. Out of 263 patients, 51 had RD (19%), and 30 had prolonged PACU stay due to RD (11%). To assess the genetic effects of ABCB1 SNPs, the raw outcome measurements were first summarized by genotypes. Several potential associations were observed, especially the associations between prolonged PACU stay due to respiratory depression and rs9282564 in both white and black patients (Tables 17 and 18). To further confirm the genetic effects, statistical modeling was conducted in which covariates that showed significant impact on outcomes were adjusted. Statistically significant effects of rs9282564 was detected on prolonged PACU stay due to respiratory depression in whites (p=0.0012) (FIG. 16A). This finding was replicated in blacks (p=0.0251) (FIG. 16B). When races were combined and adjusted, the ABCB1 SNP, rs9282564 was strongly associated with prolonged PACU stay due to respiratory depression (p=0.0002) (FIG. 16C). Adding one copy of the minor allele (G) of rs9282564 increased the odds of prolonged PACU stay by 4.1 fold (95% CI: 1.7-9.9) and 13.9 fold (95% CI: 1.1-175.8) in whites and blacks, respectively. When races were combined, adding one copy of the minor allele (G) increased the odds of prolonged PACU stay by 4.7 fold (95% CI: 2.1-10.8) (FIG. 17). No race-specific rs9282564 effect on prolonged PACU stay due to respiratory depression was detected. No other variants reached nominal association with RD or prolonged PACU due to RD in race specific or combine analyses. For the association between rs9282564 and prolonged PACU stay due to RD, out of 1000 replicates, only 1 test showed p value less than the observed p value of 0.0002 resulting in an empirical p value of 0.002 and supporting the significance of this finding.

ABCB1 and Analgesia outcomes: Three analgesic outcomes were examined: maximum FLACC scores, intervention need and post-operative morphine dose in patients who needed intervention(s). The median of maximum FLACC scores was 3 with IQR of 0.6. Out of 263 patients, 162 (62%) needed analgesic intervention(s). On average, patients who needed post-operative morphine intervention had 0.10±0.05 mg/kg morphine. Association was detected between rs2229109 and post-operative morphine doses in patients receiving rescue dose of morphine. Though it was nominal in whites (p=0.05), the association was statistically significant in blacks (p=0.01). When races were combined, association of rs2229109 with post-operative morphine was still detected (p=0.02); adding one copy of minor allele (A) decreased post-operative morphine dose by 0.04 mg/kg (95% CI: 0.01-0.07). No race-specific effect was detected. For the association between rs2229109 and post-operative morphine dose, 13 out of 1000 replicates showed p value <0.02 resulting in an empiric p-value of 0.014, thus supporting the significance of this finding.

Figure 19:
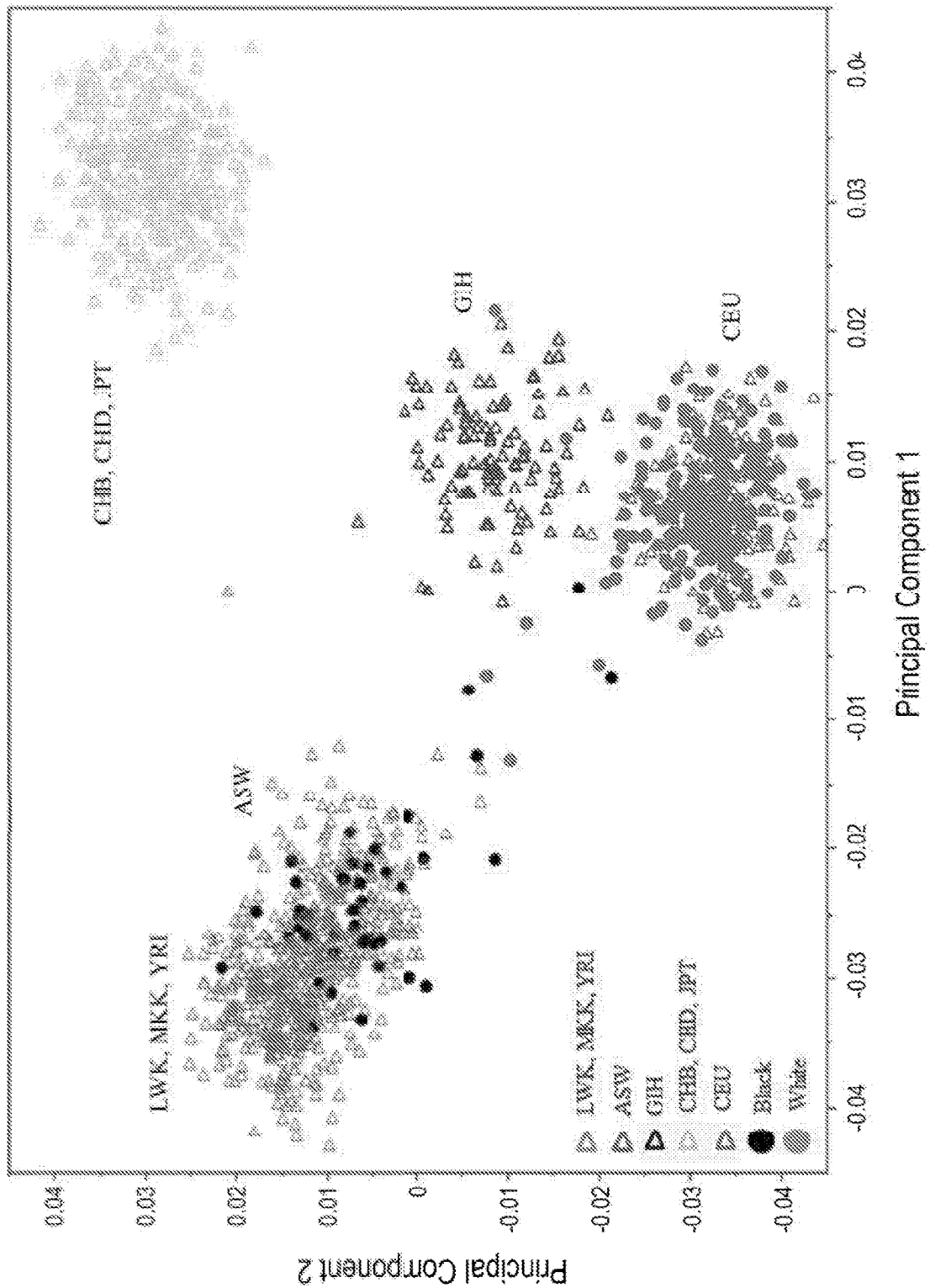
FIG. 19. Scatter plot of principal component one and two. Principal component analysis was performed using Golden Helix Software with 218 ancestry informative markers (AIMs). Self-reported races (white race indicated as red circles and black race as blue circles) of the study cohort were plotted with reference populations (open triangles) from the HapMap projects. Reference populations were indicated by following abbreviations and different colored open triangles as follows: Δ CEU=Utah residents with Northern and Western European ancestry; Δ ASW=African ancestry in Southwest USA; Δ LWK=Luhya in Webuye, Kenya; Δ MKK=Maasai in Kinyawa, Kenya; Δ YRI=Yoruba in Ibadan, Nigeria; Δ CHD=Chinese in Metropolitan Denver, Colo.; Δ CHB=Han Chinese in Beijing, China; Δ JPT=Japanese in Tokyo, Japan; and A GIH=Gujarati Indians in Houston, Tex.

Self-reported Race and Genetic Ancestry: Self-reported white and black races were compared with genetic ancestries estimated from 218 AIMs. As shown in FIG. 19, in 250 (>95%) children, self-reported race clustered well with CEU and African ancestry. Principal component (PC) 1 and 2 successfully separated white and black races (FIG. 19). In this study, self-reported race was used, as it is readily available to clinicians compared to AIMs. However, genetic ancestry was used to confirm the correlations observed with self-reported race and significant clinical outcomes. Using models adjusted for PC1 and 2, the association between respiratory depression leading to prolonged PACU stays and rs9282564 ($p<0.0001$) was further confirmed, in addition to the association between post-operative morphine requirement and rs2229109 ($p=0.03$).

This study showed associations between ABCB1 polymorphisms and clinically relevant opioid-related respiratory repression resulting in prolonged recovery room stays, and postoperative morphine requirements in a homogenous group of 263 American children undergoing a common surgical procedure under general anesthesia. Importantly, this study demonstrated that the ABCB1 SNP, rs9282564, was associated with prolonged PACU stay due to respiratory depression in whites ($p=0.0012$), in blacks ($p=0.0251$) and in both races combined ($p=0.0002$). The effect of carrying each additional copy of the minor allele (G) of the ABCB1 SNP, rs9282564, increased the odds of respiratory depression resulting in prolonged PACU stay by 4.7 fold (95% CI: 2.1-10.8). This is a novel report of association with opioid induced respiratory depression and this effect size is comparable to effect sizes in known genetic variants which have been utilized for pharmacogenetic clinical testing.

Another clinically relevant association observed in this study was between the ABCB1 SNP, rs2229109 and post-operative morphine doses in children who needed rescue dose of morphine in PACU. Each additional copy of the minor allele (A) of the ABCB1 SNP, rs2229109, decreased post-operative morphine dose by 0.04 mg/kg (95% CI: 0.01-0.07) indicating children with AA genotype are sensitive to morphine and need less morphine. The ABCB1 SNP rs2229109 is also a missense polymorphism; allele change of G to A at position 1692 on the nucleic acid causes a change in amino acid residue (Ser to Asn) in the ABCB1 protein. This variant has been recently implicated to affect methadone pharmacokinetics as part of a haplotype in association with the other variants included in this study (Barratt, D. et al., *Pharmacogenomics and Personalized Medicine*, 5:53-62 (2012)).

Figure 18:
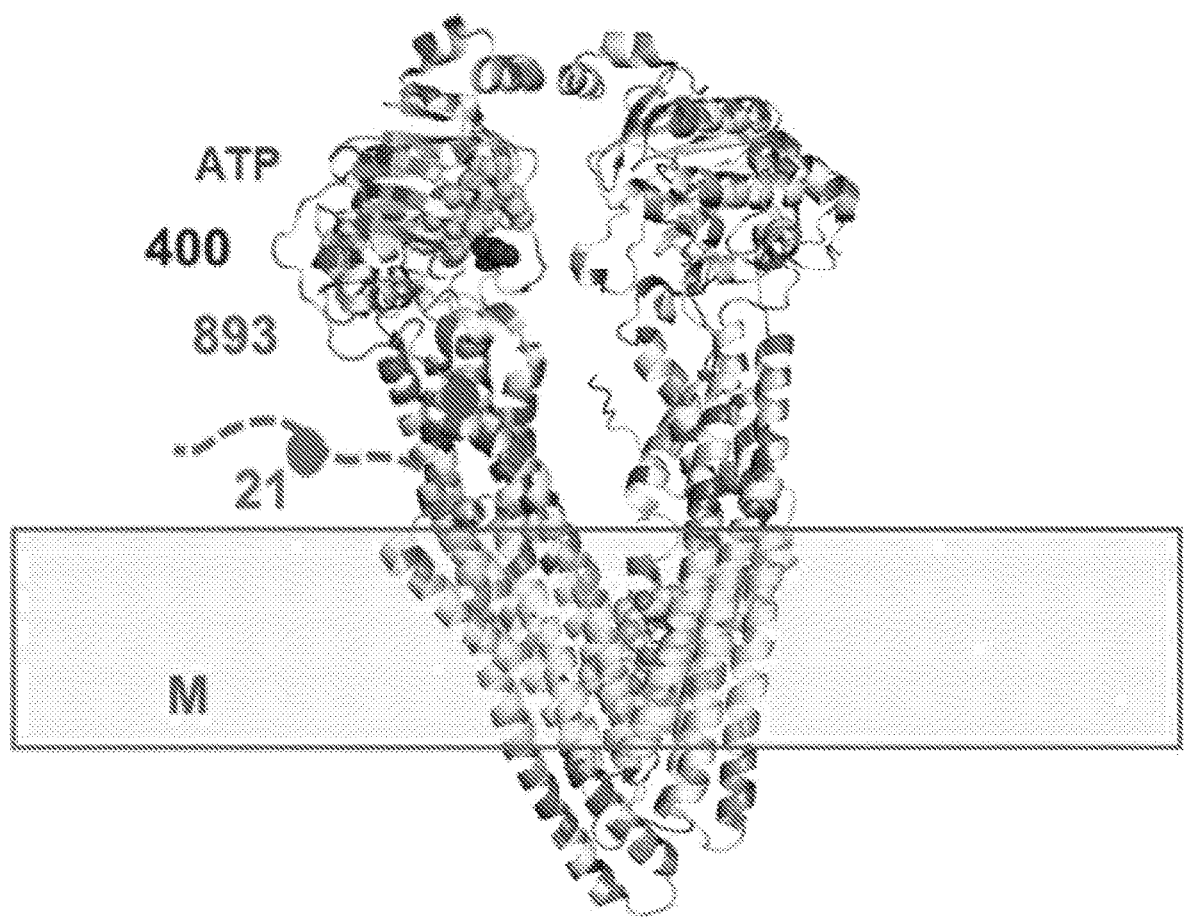

There has previously been no investigation into the effect of polymorphisms of ABCB1 gene on morphine related adverse outcomes in a relatively large and homogenous American population, especially children. This study attempted to build on the previous research while minimizing many of the previous limitations (Leschziner, G. et al., *The Pharmacogenomics Journal*, 7:154-179 (2007)) and included additional non-synonymous SNPs in addition to common ABCB1 SNPs (FIG. 18).

There are some limitations to this study. Due to geographical location of subject recruitment, there were not many non-white children to generalize these findings to other races. Nonetheless, the findings were still replicated in African Americans. For ease of use and its ready availability to clinicians, self-reported race was used. However, a very high correlation (>95%) was observed between self-reported race and genetic ancestry (FIG. 19). A large multicenter trial, including children from different ancestry, would help study the effects of ABCB1 genotypes in different races. Though the ABCB1 SNPs associated with clinical outcomes in this study are non-synonymous and associated with amino acid change, they may not be causal rather they may be in linkage with the causal markers of respiratory depression and post-operative morphine dose (FIG. 18). Sequencing or dense SNP analyses of ABCB1 could help determine if other variants have better discrimination of high versus low risk.

In conclusion, novel associations were found in children undergoing tonsillectomy between ABCB1 polymorphisms and postoperative opioid related respiratory depression and opioid requirement. ABCB1 rs9282564 GG homozygotes had an increased risk of respiratory depression resulting in prolonged hospital stays, and ABCB1 rs2229109 CC homozygotes required more morphine when postoperative analgesic interventions were needed. These findings have important implications for the post-operative management of pain in pediatric surgical patients. Proactive risk identification, stratification and preventive measures are important in minimizing the negative impact of opioid-related respiratory depression. Additional validations and examination of potential gene-gene interactions will be necessary before applying this ABCB1 genetic association data to clinical practice.

The various methods and techniques described above provide a number of ways to carry out the application. It is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features, and steps discussed above, as well as other known equivalents for each such element, feature, or step, can be employed in various combinations by one of ordinary skill in this art to perform methods in accordance with the principles described herein. Among the various elements, features, and steps, some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters are to be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for treating a patient in need of analgesia, the method comprising
   determining the patient's genotype utilizing a method comprising one or more of a polymerase chain reaction (PCR), gel electrophoresis, mass spectrometry, and array hybridization for at least one genetic variant selected from the group consisting of ABCB1 rs9282564, ABCC3 rs4148412, and ABCC3 kgp8560677,
   assigning the patient into one of two risk groups defined as low risk and high risk for a serious opioid-induced adverse event,
   wherein the patient is assigned into either the high risk group or the low risk group based upon the patient's genotype for the at least one genetic variant such that the patient is assigned to the high risk group if the patient has at least one high risk genotype for the at least one genetic variant and the patient is assigned to the low risk group if the patient lacks any high risk genotypes,
   wherein the high risk genotypes are defined as follows:
   ABCB1 rs9282564, a genotype of either GG or AG is high risk for respiratory depression [RD];
   ABCC3 rs4148412, a genotype of either AA or AG is high risk for prolonged stay in recovery due to RD [prolongRD]; and
   ABCC3 kgp8560677, a genotype of either AA or AG is high risk group for post-operative nausea and vomiting [PONV],
   and
   administering to the patient assigned to the high risk group a non-morphine opioid or a non-opioid analgesic; or administering to the patient assigned to the low risk group any one of a non-morphine opioid analgesic, a non-opioid analgesic, an opioid analgesic other than morphine, or morphine.

2. The method of claim 1, wherein the at least one genetic variant further comprises at least one additional variant selected from the group consisting of OPRM1 rs1799971, FAAH rs 324420, and ABCB1 rs1045642.

3. The method of claim 2, wherein the high risk genotypes are defined for each of the at least one additional variants as follows:
   OPRM1 rs1799971, a genotype of either GG or AG is high risk for [RD];
   FAAH rs324420, a genotype of either AA or AC is high risk for [PONV]; and
   ABCB1 rs1045642, a genotype of either TT or TC is high risk for [RD].

4. The method of claim 1, wherein the PONV is refractory.

5. The method of claim 1, wherein the assigning is performed by a computer implemented method.

6. The method of claim 5, wherein the computer implemented method comprises a decision rule.

7. The method of claim 5, wherein the computer implemented method comprises encoding the genotypes such that each genetic variant gives rise to two coupled binary variables.

8. The method of claim 6, wherein the decision rule comprises
   IF [(rs9282564=AA) OR (rs4148412=GG) OR (kgp8560677=GG)] THEN RISK=NO (low)
   ELSE RISK=YES (high).

9. The method of claim 1, wherein at least one additional non-genetic factor is utilized to refine the assignment of the patient into one of the two risk groups or to select a dose of the medication.

10. The method of claim 9, wherein the at least one additional non-genetic factor is selected from gender, race, age, and diagnosis.

11. The method of claim 10, wherein the patient is a female pediatric patient of Caucasian ancestry assigned to the low risk group, and the opioid analgesic is administered such that the total dose does not exceed 0.15 mg/kg, 0.2 mg/kg, or 0.275 mg/kg.

12. The method of claim 1, wherein the patient is a pediatric patient.

13. The method of claim 1, wherein the patient is of Caucasian ancestry.

14. The method of claim 1, wherein the patient's genotype is received directly from equipment used in determining the patient's genotype.

15. The method of claim 1, wherein the patient's genotype is determined by a method comprising obtaining or receiving a biological sample from the patient, extracting DNA from the sample, and analyzing the DNA to determine the patient's genotype at each genetic variant in the panel.

16. The method of claim 15, wherein the DNA is analyzed using a polymerase chain reaction based genotyping platform.

17. The method of claim 16, wherein the genotyping platform utilizes a 5' nuclease assay for amplifying and detecting specific genetic variants.

18. The method of claim 15, wherein the biological sample is selected from a blood sample and a buccal swab.

19. The method of claim 1, wherein the non-opioid analgesic is selected from the group consisting of paracetamol and a non-steroidal anti-inflammatory drug (NSAID).

20. The method of claim 1, wherein the the opioid analgesic other than morphine is selected from the group consisting of fentanyl, hydromorphone, codeine, oxycodone, hydrocodone, tramadol, ondansetron, dexamethasone, methadone, alfentanil, and remifentanil.

21. The method of claim 1, wherein the method comprises administering to the patient assigned to the low risk group either an opioid analgesic other than morphine, or morphine.

22. The method of claim 21, wherein the the opioid analgesic other than morphine is selected from the group consisting of fentanyl, hydromorphone, codeine, oxycodone, hydrocodone, tramadol, ondansetron, dexamethasone, methadone, alfentanil, and remifentanil.

* * * * *